US008846883B2

(12) United States Patent
Brown et al.

(10) Patent No.: US 8,846,883 B2
(45) Date of Patent: Sep. 30, 2014

(54) OLIGONUCLEOTIDE LIGATION

(75) Inventors: Tom Brown, Southampton (GB); Afaf Helmy El-Sagheer, Southampton (GB)

(73) Assignee: University of Southhampton, Southhampton (GB)

(*) Notice: Subject to any disclaimer, the term of this patent is extended or adjusted under 35 U.S.C. 154(b) by 0 days.

(21) Appl. No.: 13/409,927

(22) Filed: Mar. 1, 2012

(65) Prior Publication Data

US 2013/0046084 A1 Feb. 21, 2013

Related U.S. Application Data

(63) Continuation-in-part of application No. 13/210,948, filed on Aug. 16, 2011, now abandoned.

(51) Int. Cl.
| | |
|---|---|
| C07H 21/00 | (2006.01) |
| C07H 21/02 | (2006.01) |
| C07H 21/04 | (2006.01) |
| C12Q 1/68 | (2006.01) |
| C12P 19/34 | (2006.01) |

(52) U.S. Cl.
USPC ......... 536/23.1; 536/25.3; 536/26.6; 435/6.1; 435/91.1; 435/91.2

(58) Field of Classification Search
USPC ............... 435/6.1, 91.1, 91.2; 536/23.1, 25.3, 536/26.6
See application file for complete search history.

(56) References Cited

FOREIGN PATENT DOCUMENTS

WO WO 2008/120016 A1 10/2008

OTHER PUBLICATIONS

Nuzzi et al. QSAR & Combinatorial Science, 2007, 26(11-12), 1191-1199. (abstract only).*
El-Sagheer et al., "Biocompatible artificial DNA linker that is read through by DNA polymerases and is functional in *Escherichia coli*," PNAS, vol. 108, No. 28, pp. 11338-11343 (Jul. 12, 2011).
El-Sagheer et al., "New strategy for the synthesis of chemically modified RNA constructs exemplified by hairpin and hammerhead ribozymes," PNAS, vol. 107, No. 35, pp. 15329-15334 (Aug. 31, 2010).
El-Sagheer et al., "Synthesis and Polymerase Chain Reaction Amplification of DNA Strands Containing an Unnatural Triazole Linkage," J. Am. Chem. Soc., vol. 131, No. 11, pp. 3958-3964 (Mar. 26, 2009).
Kocalka et al., "Rapid and Efficient DNA Strand Cross-Linking by Click Chemistry," ChemBioChem, vol. 9, pp. 1280-1285 (2009).
Kumar et al., "Template-Directed Oligonucleotide Strand Ligation, Covalent Intramolecular DNA Circularization and Catenation Using Click Chemistry," J. Am. Chem. Soc., vol. 129, pp. 6859-6864 (2007).

* cited by examiner

*Primary Examiner* — Jezia Riley
(74) *Attorney, Agent, or Firm* — Patterson Thuente Pedersen P.A.

(57) ABSTRACT

Oligonucleotide chemistry is central to the advancement of core technologies such as DNA sequencing, forensic and genetic analysis and has impacted greatly on the discipline of molecular biology. Oligonucleotides and their analogues are essential tools in these areas. They are often produced by automated solid-phase phosphoramidite synthesis but it is difficult to synthesize long DNA and RNA sequences by this method. Methods are proposed for ligating oligonucleotides together, in particular the use of an azide-alkyne coupling reaction to ligate the backbones of oligonucleotides together to form longer oligonucleotides that can be synthesized using current phosphoramidite synthesis methods.

27 Claims, 21 Drawing Sheets

```
CLUSTAL 2.0.12 multiple sequence alignment

Click           ------------------------------------------------------------
Template        ATGAGTATTCAACATTTCCGTGTCGCCCTTATTCCCTTTTTTGCGGCATTTTGCCTTCCT   60

Click           ------------------------------------------------------------
Template        GTTTTTGCTCACCCAGAAACGCTGGTGAAAGTAAAAGATGCTGAAGATCAGTTGGGTGCA  120

Click           ------------------------------------------------------------
Template        CGAGTGGGTTACATCGAACTGGATCTCAACAGCGGTAAGATCCTTGAGAGTTTTCGCCCC  180

Click                                         --AAAGTTCTGCTATGTGGCGCGGTATTATCC   30
Template        GAAGAACGTTTTCCAATGATGAGCACTTTTAAAGTTCTGCTATGTGGCGCGGTATTATCC  240
                                                  ******************************

Click           CGTATTGACGCCGGGCAAGAGCAACTCGGTCGCCGCATACACTATTCTCAGAATGACTTG   90
Template        CGTATTGACGCCGGGCAAGAGCAACTCGGTCGCCGCATACACTATTCTCAGAATGACTTG  300
                ************************************************************
                       ScaI
Click           GTTGAGTACTCACCAGTCACACAAAAGCATCTTACGGATGGCATGACAGTAAGAGAATTA  150
Template        GTTGAGTACTCACCAGTCACAGAAAAGCATCTTACGGATGGCATGACAGTAAGAGAATTA  360
                ********************* **************************************
                                                                        PvuI
Click           TGCAGTGCTGCCATAACCATGAGTGATAACACTGCGGCCAACTTACTTCTGACAACGATC  210
Template        TGCAGTGCTGCCATAACCATGAGTGATAACACTGCGGCCAACTTACTTCTGACAACGATC  420
                ************************************************************

Click           GGAGGACCGAAGGAGCTAACCGCTTTTTTGCACAACATGGGGGATCATGTAACTCGCCTT  270
Template        GGAGGACCGAAGGAGCTAACCGCTTTTTTGCACAACATGGGGGATCATGTAACTCGCCTT  480
                ************************************************************

Click           GATCGTTGGGAACCGGAGCTGAATGAAGCCATACCAAACGACGAGCGTGACACCACGATG  330
Template        GATCGTTGGGAACCGGAGCTGAATGAAGCCATACCAAACGACGAGCGTGACACCACGATG  540
                ************************************************************

Click           CCTGTAGCAATGGCAACAACGTTGCGCAAACTATTAACTGGCGAACTACTTACTCTAGCT  390
Template        CCTGTAGCAATGGCAACAACGTTGCGCAAACTATTAACTGGCGAACTACTTACTCTAGCT  600
                ************************************************************

Click           TCCCGGCAACAATTAATAGACTGGATGGAGGCGGATAAAGTTGCAGGACCACTTCTGCGC  450
Template        TCCCGGCAACAATTAATAGACTGGATGGAGGCGGATAAAGTTGCAGGACCACTTCTGCGC  660
                ************************************************************

Click           TCGGCCCTTCCGGCTGGCTGGTTTATTGCTGATAAATCTGGAGCCGGTGAGCGTGGGTCT  510
Template        TCGGCCCTTCCGGCTGGCTGGTTTATTGCTGATAAATCTGGAGCCGGTGAGCGTGGGTCT  720
                ************************************************************

Click           CGCGGTATCATTGCAGCACTGGGGCCAGATGGT----------------------------  543
Template        CGCGGTATCATTGCAGCACTGGGGCCAGATGGTAAGCCCTCCCGTATCGTAGTTATCTAC  780
                *********************************

Click           ------------------------------------------------------------
Template        ACGACGGGGAGTCAGGCAACTATGGATGAACGAAATAGACAGATCGCTGAGATAGGTGCC  840

Click           -------------------
Template        TCACTGATTAAGCATTGGTAA  861
```

Figure 23

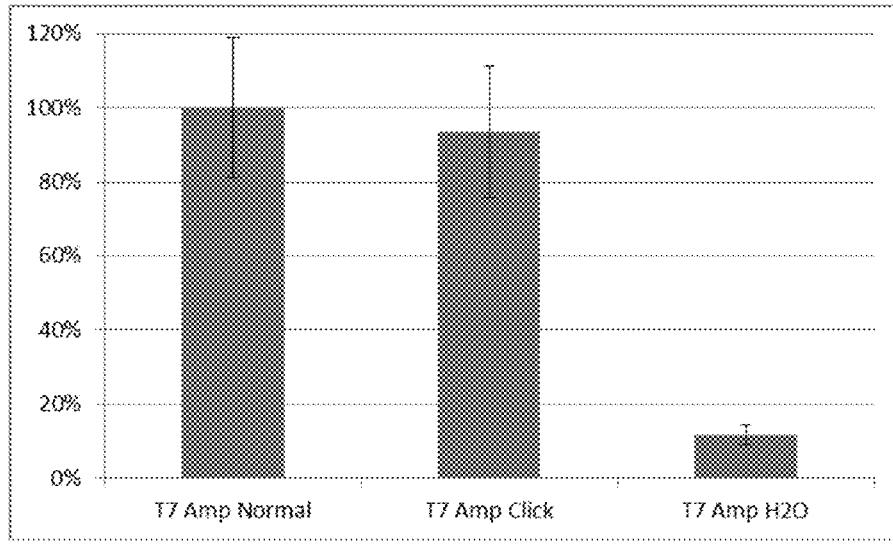

Figure 24

```
                          ScaI
AUvrB normal     ATGACTTGGTTGAGTACTCA  AGTCACAGAAAAGCATCTTACGGATGGCATGACAGTAA
AUvrB click      ATGACTTGGTTGAGTACTCA  AGTCACAGAAAAGCATCTTACGGATGGCATGACAGTAA
Plasmid control  ATGACTTGGTTGAGTACTCA  AGTCACAGAAAAGCATCTTACGGATGGCATGACAGTAA
                 ****************************************************

AUvrB normal     GAGAATTATGCAGTGCTGCCATAACCATGAGTGATAACACTGC  CCAACTTACTTCTGA
AUvrB click      GAGAATTATGCAGTGCTGCCATAACCATGAGTGATAACACTGC  CCAACTTACTTCTGA
Plasmid control  GAGAATTATGCAGTGCTGCCATAACCATGAGTGATAACACTGC  CCAACTTACTTCTGA
                 ****************************************************

PvuI
AUvrB normal     CAACGATCGGAGGACCGAAGGAGCTAACCGCTTTTTTGCACAACATGGGGGATCATGTAA
AUvrB click      CAACGATCGGAGGACCGAAGGAGCTAAC--------------------------------
Plasmid control  CAACGATCGGAGGACCGAAGGAGCTAAC--------------------------------
                 ****************
```

Figure 25

OLIGONUCLEOTIDE LIGATION

RELATED APPLICATIONS

This application is a continuation in part of U.S. patent application Ser. No. 13/210,948, filed Aug. 16, 2011, the disclosure of which is hereby incorporated by reference herein in its entirety.

FIELD OF THE INVENTION

This invention relates to a method for ligating oligonucleotides together, and in particular it relates to use of an azide-alkyne coupling reaction to ligate the backbones of oligonucleotides together. It also relates to oligonucleotides comprising a triazole phosphodiester mimic.

All publications referred to in this application are hereby incorporated by reference in their entirety. A sequence Listing appended to the present specification is herein incorporated by reference in its entirety.

BACKGROUND OF THE INVENTION

Oligonucleotide chemistry is central to the advancement of core technologies such as DNA sequencing, forensic and genetic analysis and has impacted greatly on the discipline of molecular biology. Oligonucleotides and their analogues are essential tools in these areas. They are often produced by automated solid-phase phosphoramidite synthesis. However, this process can only assemble DNA strands up to about 150 bases in length. Synthesis of long RNA strands is more difficult owing to problems caused by the presence of the 2'-hydroxyl group of ribose which requires selective protection during oligonucleotide assembly. This reduces the coupling efficiency of RNA phosphoramidite monomers due to steric hindrance. In addition, side-reactions which occur during the removal (or premature loss) of the 2'-protecting groups cause phosphodiester backbone cleavage and 3' to 2' phosphate migration. Although several ingenious strategies have been developed to minimise these problems and to improve the synthesis of long RNA molecules, the chemical complexity of solid-phase RNA synthesis dictates that constructs longer than 50 nucleotides in length remain difficult to prepare. Most biologically important DNA and RNA molecules for example genes, ribozymes, aptamers and riboswitches are significantly longer than the length that is currently achievable by solid-phase synthesis, so new approaches to the synthesis of long DNA and RNA molecules are urgently required.

Although DNA and RNA synthesis by enzymatic replication or transcription might seem a viable alternative, it does not permit the site-specific incorporation of multiple modifications at sugars, bases, or phosphates and also leads to the loss of epigenetic information such as DNA methylation.

In contrast, automated solid-phase DNA and RNA synthesis is compatible with the introduction of methylated nucleotides, fluorescent tags, isotopic labels (for NMR studies) and other groups to improve biological activity and resistance to enzymatic degradation. The scope and utility of important DNA and RNA constructs can be significantly extended by such chemical modifications.

Another drawback of enzymatic replication or transcription is that the DNA and RNA products can only be cost-effectively produced at a small scale. The scale of chemical synthesis, by contrast, is potentially unlimited.

Previous studies have attempted to chemically ligate synthesized oligonucleotides to form longer DNA molecules as described in WO2008/120016, Kumar et al. 2007, J Am Chem Soc 129, 6859-6864, Kocalka et al. 2008, Chem Bio Chem, 9, 1280-1285, and El-Sagheer et al. 2009, J Am Chem. Soc. 131(11), 3958-3964. The drawback with these molecules was that, because they contained unnatural linkages between the oligonucleotides they were not fully active in a biological system. DNA and RNA polymerases could not read these nucleotide sequences accurately and mis-read or missed out nucleotides when trying to replicate the sequences.

Enzymatic ligation using, for example T4 DNA ligase can be used to join oligonucleotides but the use of ligases has other drawbacks; they are often contaminated with RNase enzymes which can partially degrade the ligation products, and the ligation protocols require subsequent removal of the ligase protein to produce pure DNA or RNA. Moreover, enzymatic ligation methods are not suitable for the large scale synthesis of DNA or RNA, and the yields of enzymatic ligation are sometimes low, particularly when using chemically modified DNA or RNA substrates or mixed DNA/RNA strands.

It would therefore be advantageous to provide a method that can be used on an industrial scale and can synthesize long DNA and RNA molecules that can be read correctly by DNA and RNA polymerases and hence can be used for in vitro and in vivo applications including applications in biology and nanotechnology.

SUMMARY OF THE INVENTION

It is an aim of embodiments of the present invention to provide an efficient method of chemical ligation that can ligate oligonucleotides together by forming a link between the oligonucleotide backbones that is a triazole phosphodiester mimic in RNA as described in El-Sagheer and Brown 2010, PNAS vol. 107 no. 35, 15329-15334 and is also a phosphodiester mimic in DNA that can be read through by DNA and RNA polymerases as described in El-Sagheer et al. 2011, PNAS vol. 108 no. 28. 11338-11343. Both of the above publications are incorporated herein in their entirety.

According to a first aspect of the present invention a method is provided for ligating one or more oligonucleotides together. The method comprises reacting at least one alkyne group with at least one azide group to form at least one triazole phosphodiester mimic. The reaction is selected from the following reaction schemes. The reaction schemes are drawn showing a linkage being formed between deoxyribose groups, for example of a DNA molecule. Equivalent reactions can be carried out between the ribose groups of an RNA molecule or a nucleotide analogue and therefore the RNA equivalents and the equivalents using nucleotide analogues of the below reactions, linking the ribose groups of an RNA molecule or a nucleotide analogue molecule are also contemplated within the scope of the present invention. The reactions are applicable to nucleic acid analogues, for example, nucleotide analogues containing modifications to the sugars, for example 2'-O methyl RNA, 2'-fluoro RNA and/or LNA.

3 4
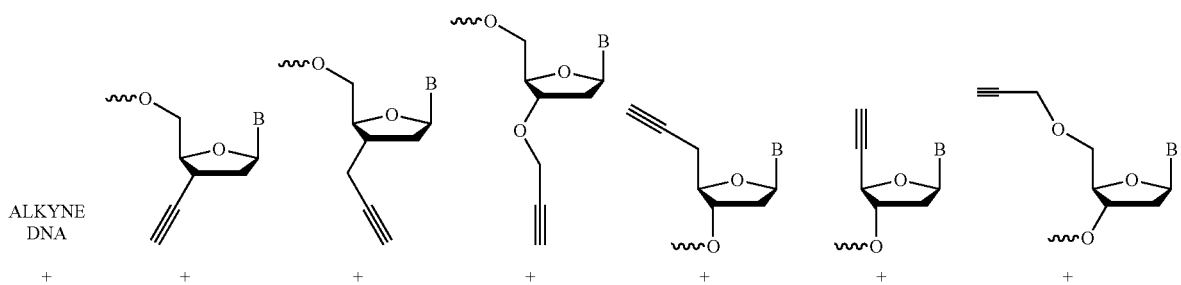
ALKYNE DNA
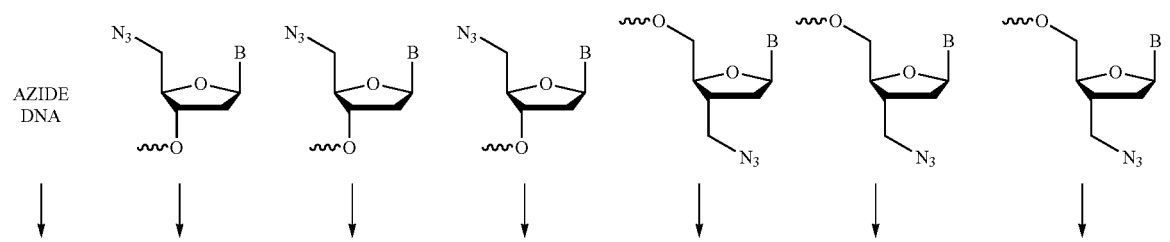
AZIDE DNA
TRIAZOLE PHOSPHO DIESTER MIMIC
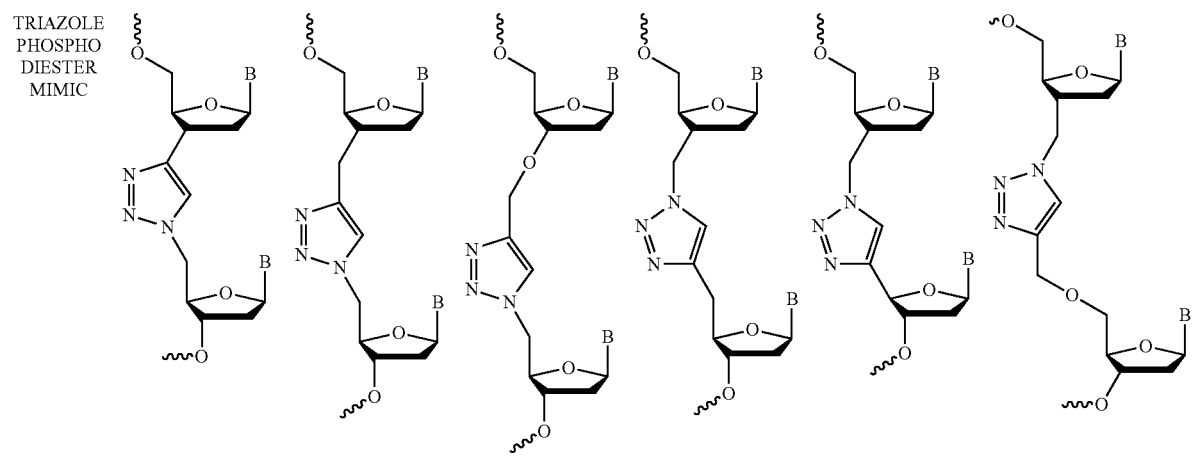
ALKYNE DNA
AZIDE DNA
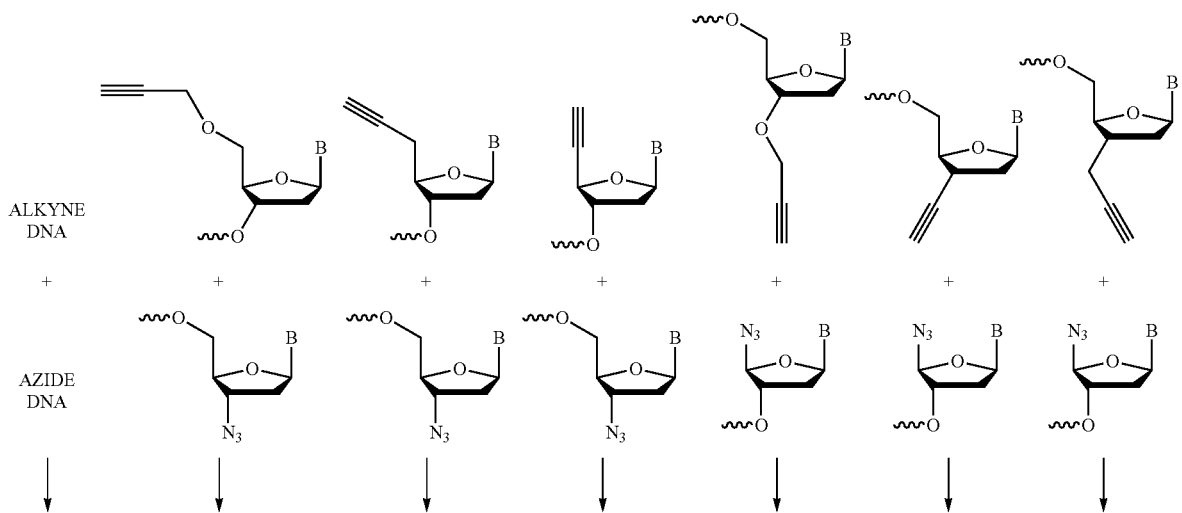

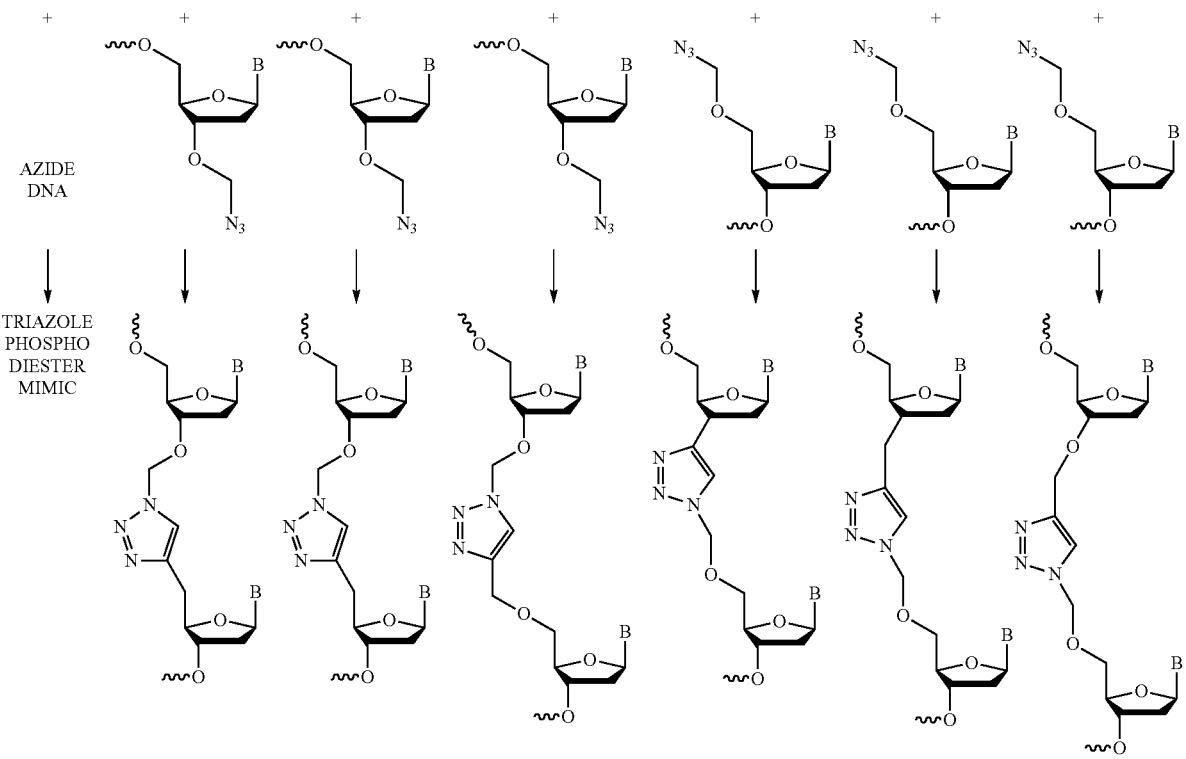

B = T, C, G or A

This method is advantageous because it employs a chemical synthesis reaction that is fast and can be performed on an industrial scale. In one embodiment the method of the present invention can be used to ligate together DNA or RNA molecules that have been produced chemically using phosphoramidite synthesis. In another embodiment the method of the present invention can be used to ligate together natural or enzymatically produced oligonucleotides to which alkynes or azides can be introduced to the 5'-end via 5'-alkyne or azide modified PCR primers and at the 3'-end by DNA polymerase enzymes.

The oligonucleotides ligated by the method of the present invention may be made of DNA or RNA. In one embodiment two DNA oligonucleotides may be ligated together. In another embodiment two RNA oligonucleotides may be ligated together. In a further embodiment a DNA oligonucleotide may be ligated to an RNA oligonucleotide. In another embodiment the oligonucleotides may comprise one or more synthetic nucleotides. In a further embodiment 2, 3, 4, 5, 6, 7, 8, 9, 10 or more than 10 oligonucleotides may be ligated together. In one embodiment this method may be used to ligate together oligonucleotides to form an oligonucleotide comprising more than 20, more than 40, more than 50, more than 80, more than 100, more than 200, more than 500, more than 800, more than 1000, more than 1500 or more than 2000 residues.

The method comprises reacting at least one alkyne group with at least one azide group. A suitable alkyne group may be chemically joined to the 3' end of a DNA or an RNA oligonucleotide to provide an oligonucleotide that is useful in the present invention. A suitable azide group may be chemically joined to the 5' end of a DNA or an RNA oligonucleotide to provide an oligonucleotide that is useful in the method of the present invention. Suitable alkyne and azide groups for use in the present invention are shown above. Alternatively the alkyne can be added to the 5'-end of an oligonucleotide and the azide to the 3'-end of an oligonucleotide. In one embodiment an alkyne group can be added to each end of an oligonucleotide. In another embodiment azide groups can be added to each end of an oligonucleotide. In a further embodiment an alkyne group can be added to one end of an oligonucleotide and an azide group can be added to the other end of the same oligonucleotide.

In one embodiment the reaction between an alkyne group and an azide group is an example of a type of reaction known as "click chemistry". Ligating DNA and/or RNA molecules using a click chemistry reaction is advantageous because click chemistry reactions may be fast, modular, efficient, may not produce toxic waste products, can be done with water as a solvent and/or may be stereospecific.

In one embodiment the present invention uses the CuAAC reaction for DNA and/or RNA ligation this is advantageous because of its very high speed, efficiency, orthogonality with functional groups present in nucleic acids, its compatibility with aqueous media and the ability to switch on the reaction by adding Cu(I) after oligonucleotides have been annealed. In one embodiment, individual DNA or RNA oligonucleotides may be assembled by automated solid phase synthesis, purified by HPLC then chemically ligated by click chemistry using the CuAAC reaction to produce much larger molecules. The CuAAC reaction may be catalysed by Cu (I), which may be produced in the reaction mixture.

A Cu(I)-binding ligand may also be used to prevent Cu(I)-catalysed oligonucleotide degradation.

In one embodiment the click reaction can be carried out on a solid-phase support, for example resin beads or a column comprising a suitable substrate or synthesis resin. The azide oligonucleotide can be left on a synthesis resin on an oligonucleotide synthesis column and the alkyne oligonucleotide can be added to the resin in the presence of aqueous Cu(I) so that the reaction occurs on solid-phase in a non-templated mode. This has the advantage that an excess of the alkyne oligonucleotide can be used to make the reaction very efficient. The excess unreacted alkyne oligonucleotide can be washed away leaving the ligated oligonucleotide (containing the triazole linkage) on the resin. This can then be cleaved from the resin and deprotected using standard procedures.

Alternatively the same procedure can be carried out with the alkyne oligonucleotide bound to the resin and the azide oligonucleotide in solution. An example of the reaction on a solid phase is shown in FIG. 10.

The reaction of at least one alkyne group with at least one azide group in the present invention may form at least one triazole phosphodiester mimic. The triazole phosphodiester mimic joins together two ribose or deoxyribose sugars or modified deoxyribose sugars in the backbone of DNA or RNA in place of a phosphate group. The triazole phosphodiester mimic may be comprised of a triazole ring and two linkers. One linker joins the triazole ring to the ribose or deoxyribose on one side of it and the other linker joins the triazole to the ribose or deoxyribose on the other side of it.

In one embodiment the at least one triazole phosphodiester mimic can be read through accurately by a DNA polymerase and/or an RNA polymerase. This means that a DNA and/or RNA polymerase correctly replicates or transcribes the sequence of the DNA and/or RNA at the site of the triazole phosphodiester mimic. For example, the DNA and/or RNA polymerase does not read the bases next to the triazole phosphodiester mimic incorrectly or skip a base near the site of the triazole phosphodiester mimic. This is advantageous because DNA and/or RNA molecules can be ligated together and the ligation product can be correctly read and/or copied by polymerases in vitro and/or in vivo.

In one embodiment a nucleic acid comprising at least one triazole phosphodiester mimic according to the present invention is active in vivo. For example the DNA or RNA sequence comprising at least one triazole phosphodiester mimic can direct the production of a functional polypeptide in living cells.

In one aspect the present invention relates to an oligonucleotide comprising one or more alkyne and/or azide groups that can be used in the method of the present invention. For example the present invention relates to an oligonucleotide linked to at least one alkyne group comprising a structure selected from the structures shown in FIG. 9. The present invention relates to an oligonucleotide linked to at least one azide group comprising a structure selected from the structures shown in FIG. 9.

In one embodiment the reaction to form a triazole phosphodiester mimic follows the reaction scheme below or an RNA equivalent thereof:

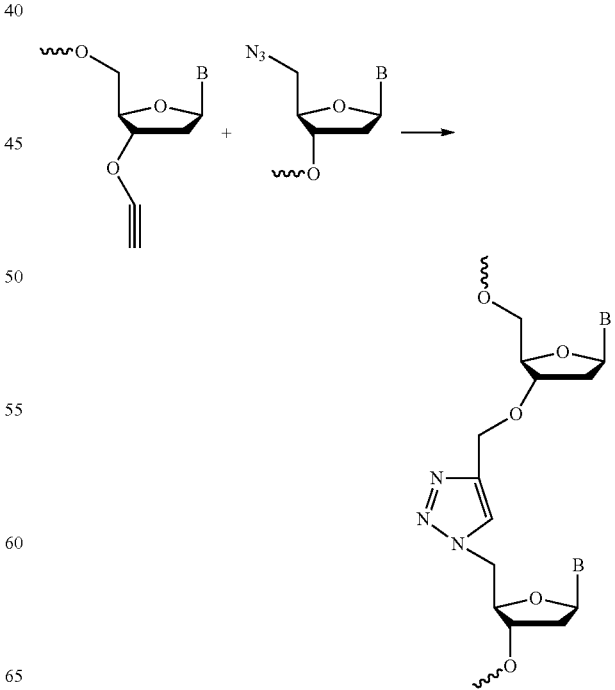

This reaction provides a triazole phosphodiester mimic that has an overall shape similar to that of a phosphodiester group. The similarity of the overall shape of this triazole phosphodiester mimic to a natural phosphodiester group can be seen in FIG. 7, which shows, at "B", the phosphodiester group of canonical DNA and at "C" a superposition of the above triazole phosphodiester mimic with a phosphodiester group of canonical DNA. As can be seen, although the structures of these two linkers are different, the overall shape is similar. In addition, one or more of the nitrogen atoms of the triazole ring can form hydrogen bonds or electrostatic interactions with the polymerase enzyme in the same manner as the oxygen atoms of the natural phosphodiester group. Without being bound by theory, it is suggested that the similarity of shape of the triazole phosphodiester mimic means that the polymerase can pass across the triazole phosphodiester mimic without the normal activity of the polymerase being disrupted. This can be shown in FIG. 7 of the present application. FIG. 7C shows a triazole phosphodiester mimic of the present invention superimposed on a structure of a canonical phosphodiester group. As can be seen the shapes of the two groups are similar.

In one embodiment an alkyne group at the 3' end of one oligonucleotide is reacted with an azide group which is at the 5' end of a second oligonucleotide to form at least one triazole phosphodiester mimic. In one embodiment an alkyne group at the 3' end of one single stranded oligonucleotide is reacted with an azide group which is at the 5' end of a second single stranded oligonucleotide to form at least one triazole phosphodiester mimic in a single stranded oligonucleotide.

In one embodiment a single stranded oligonucleotide may be circularized by reacting an alkyne group at one end of the oligonucleotide with an azide group at the other end of the oligonucleotide to form a single stranded circular oligonucleotide comprising at least one triazole phosphodiester mimic.

In another embodiment double stranded hybridized oligonucleotides may be circularized by reacting an alkyne groups at one end of each strand with azide groups at the other end of each strand to form a circularized double stranded oligonucleotide, for example a catenane, comprising at least one triazole phosphodiester mimic. A catenane can also be formed by cyclizing one oligonucleotide and then using it as a template to cyclize a second oligonucleotide to make the double stranded catenane.

In another embodiment the method of the present invention may be used on oligonucleotides that form mixed single and double stranded nucleic acid structures such as hammerhead ribozymes, hairpin ribozymes or synthetic DNA and/or RNA constructs.

The ability to introduce one or more unnatural nucleotides into synthetically produced oligonucleotides and then to ligate them together using the methods of the present invention allows a wide range of non-natural oligonucleotide constructs to be made. These constructs can be made by the methods of the present invention without the use of enzymes and on a large scale by chemical synthesis.

In one embodiment the reaction of at least one alkyne group with at least one azide group may be carried out under non-templated conditions. This means that alkyne group attached to one oligonucleotide may be reacted with an azide group attached to the same or a different oligonucleotide in the absence of a template or a splint. The reaction proceeds in the presence of Cu(I) even if the two reaction oligonucleotides have no region of complementarity, i.e. a completely non-templated click reaction. In one embodiment an oligonucleotide with an alkyne group at one end and an azide group at the other will cyclize in the presence of Cu(I) even in the absence of a splint. The rate of a non-templated reaction may be increased by increasing the concentration of the oligonucleotides comprising one or more alkyne and/or azide groups.

The oligonucleotide or oligonucleotides comprising one or more alkyne and/or azide groups may self-assemble into the correct orientation for the ligation to take place. For example, one or more ends of the oligonucleotides may be complementary to the end of another oligonucleotide to which it can hybridize to orientate the oligonucleotides before the ligation reaction. These complementary ends may for example be protruding and recessed ends, similar to the protruding and recessed "sticky ends" generated by cleavage of an oligonucleotide with a restriction enzyme.

In one embodiment the reaction of at least one alkyne group with at least one azide group may be carried out under templated conditions. In this embodiment a template oligonucleotide may be provided that will not take part in the ligation reaction or will not be ligated to an oligonucleotide that comprises one or more alkyne and/or an azide group. The oligonucleotide or oligonucleotides comprising one or more alkyne and/or azide groups may hybridize with the template. This is advantageous because it allows a two or more oligonucleotides to be assembled in the desired orientation to each other before ligating them together. In one embodiment the template may be an oligonucleotide for example a single stranded DNA or RNA oligonucleotide. In one embodiment the template may be a linear oligonucleotide, in another embodiment the template may be a circular oligonucleotide. In a further embodiment the template may be made using the method of the present invention and may comprise one or more triazole phosphodiester mimics as described in the present invention. The oligonucleotides comprising alkyne or azide groups can be hybridized to the template under suitable hybridization conditions that do not cause the alkyne and azide groups to react with one another. In one embodiment the reaction between the alkyne and azide groups proceeds very slowly in the absence of Cu(I) and the ligation reaction can be started once the oligonucleotides are annealed to the template in the right order by adding Cu(I) or by production of Cu(I) in the reaction solution at a suitable time.

In one embodiment the template may be a cyclic single-stranded oligonucleotide and a double-stranded helical oligonucleotide catenane is prepared.

In one embodiment the step of reacting at least one alkyne group with at least one azide group to form at least one triazole phosphodiester mimic may be repeated sequentially more than once, for example, more than twice, more than three times, more than four times, more than five times, more than six times or more than seven times, to form an oligonucleotide comprising more than one triazole phosphodiester mimic. The individual click reactions can be carried out sequentially.

In another embodiment several triazole linkages may be formed simultaneously if several alkyne/azide oligonucleotides are allowed to anneal to templates or to each other in the desired orientation and/or order and Cu(I) is added to instigate the reaction. Four examples of schemes for making long oligonucleotides by ligating more than one oligonucleotide using a method of the present invention are shown in FIG. 11. Splints may be oligonucleotides that are complementary to the ends of the oligonucleotides that are to be joined together. The splints may anneal to the join between the oligonucleotides at the site of the alkyne azide reaction to make sure the oligonucleotides are in the correct orientation before they are joined together. After the alkyne azide reaction the splints may be removed. An alternative method of ensuring that the oligonucleotides comprising one or more alkyne and/or azide groups align in the correct orientation and order is to ensure that they are designed with complementary single-stranded ends that can anneal to each other as shown in FIG. 11, numbers 2 and 4.

An oligonucleotide in the present invention may be two or more, preferably 3 or more, preferably 5 or more, preferably 10 or more, preferably 20 or more, preferably 30 or more, preferably 40 or more, preferably 50 or more, preferably 100 or more, DNA nucleotides and/or RNA nucleotides and/or nucleotide analogues and/or labelled nucleotides linked by phosphodiester bonds. DNA and/or RNA analogues may be, for example 2'-O-methyl RNA, 2'-fluoro RNA and/or LNA.

In another embodiment at least one oligonucleotide is DNA and at least one oligonucleotide is RNA to form a DNA-RNA hybrid oligonucleotide.

The following triazole phosphodiester mimic structures are preferred in the present invention.

TRIAZOLE PHOSPHO DIESTER MIMICS

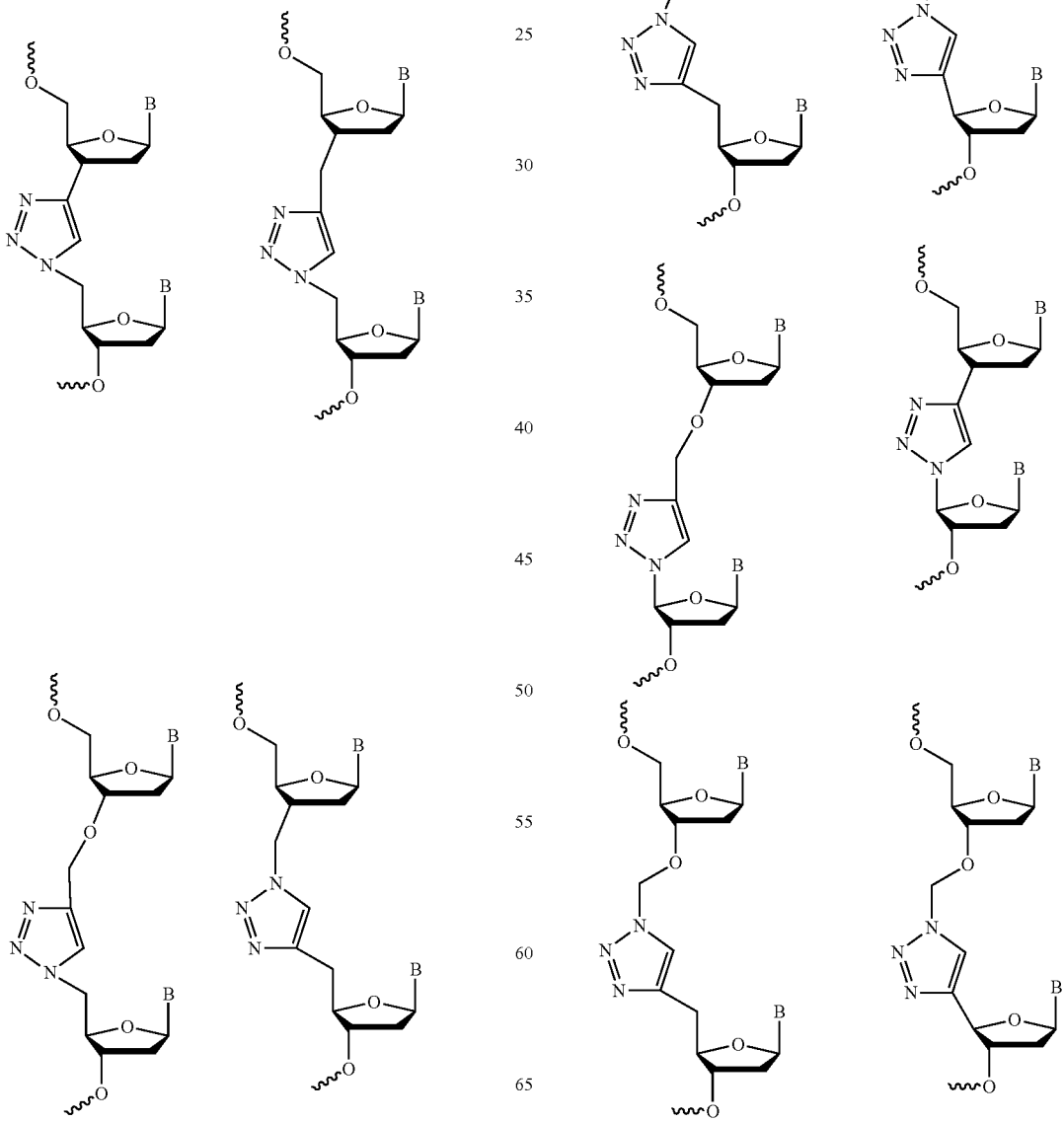

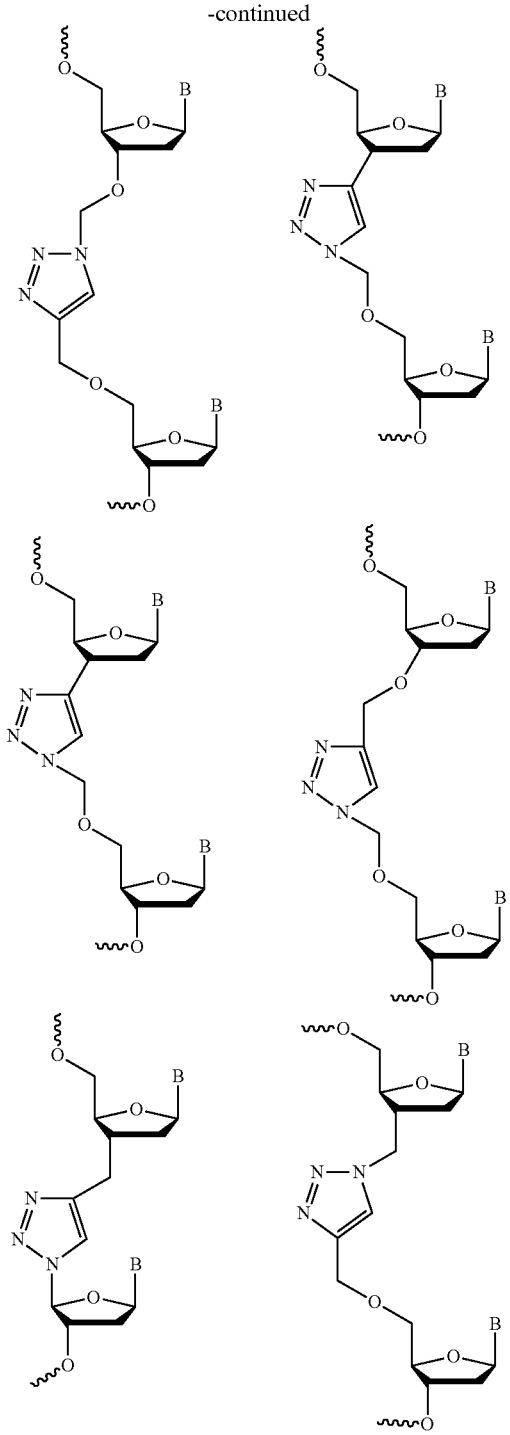

B = T, C, G or A

These structures are advantageous because they can be prepared using the CuAAC reaction by reacting an alkyne group at the end of one oligonucleotide with an azide group is at the end of a second oligonucleotide. This makes it fast and simple to use one of the above triazole phosphodiester mimic structures to link the backbones of two or more oligonucleotides together.

The triazole ring structure of each triazole phosphodiester mimic is linked to the ribose or deoxyribose structures by linkers. The oligonucleotides comprising one or more alkyne and/or azide groups for use in the reaction of the present invention can be designed in order to make any of the linkers shown above. In one embodiment a suitable linker may be chosen to suit the particular position in the oligonucleotide that the triazole phosphodiester mimic will occupy. For example linkers may be chosen to be on each side of the triazole ring in a triazole phosphodiester mimic so that the triazole phosphodiester mimic has the closest shape and/or size and/or charge distribution and/or hydrogen bonding characteristics and/or other physical properties possible to a natural phosphodiester bond. This makes it easier for a polymerase to correctly read through the triazole phosphodiester mimic and correctly replicate or transcribe the DNA. In another embodiment the linkers may be chosen to provide a desired shape to the oligonucleotide that is desirable for the design of an unnatural oligonucleotide construct.

In one embodiment the present invention relates to a method of selecting a triazole phosphodiester mimic comprising the steps of:
a) Designing an oligonucleotide construct;
b) Selecting a triazole phosphodiester mimic from those shown in FIG. 9 that has an appropriate shape and/or size and/or charge distribution and/or hydrogen bonding characteristics and/or other physical properties for the location in the oligonucleotide construct;
c) Designing oligonucleotides comprising alkyne and azide groups that can react to form the selected triazole phosphodiester mimic.

Optionally the method may also comprise the steps of:
d) Making the oligonucleotide construct designed in step a);
e) Testing the oligonucleotide construct to ensure that it contains a triazole phosphodiester mimic that is functional in vitro or in vivo.

The oligonucleotide construct may comprise at least two triazole phosphodiester mimics each having a structure selected from the constructs shown in FIG. 9 or an RNA equivalent thereof.

In one embodiment least one triazole phosphodiester mimic has the following structure or an RNA equivalent thereof:

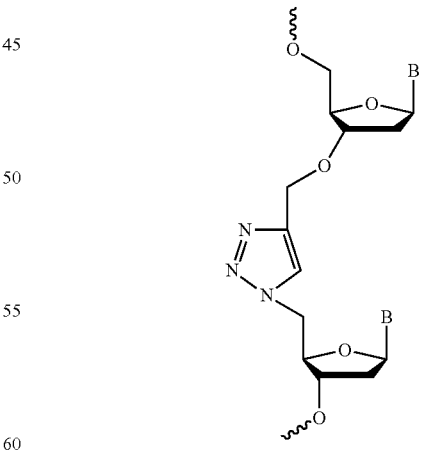

This is advantageous because this structure has a shape that closely resembles that of a canonical phosphodiester group. This triazole phosphodiester mimic is particularly suitable because it can be read through accurately by DNA and RNA polymerases. Oligonucleotides comprising this triazole phosphodiester mimic may be correctly copied by DNA polymerases and accurately transcribed by RNA polymerases in vitro and in vivo, for example they are able to direct the expression of polypeptides and proteins in vivo, for example in bacterial cells, preferably in *E. coli* cells and hammerhead ribozymes have been shown to be active with this triazole phosphodiester mimic at the active site.

The method of the present invention and the triazole phosphodiester mimics of the present invention provide a number of advantages. These include: The triazole phosphodiester mimics can be read through by a DNA and RNA polymerases. Oligonucleotides linked to an alkyne group and or an azide group for use in the method of the present invention may be easy to prepare.

The oligonucleotides comprising one or more azide and/or alkyne groups can be made on a large scale by chemical synthesis of the oligonucleotides and chemically joining an alkyne or an azide group to the oligonucleotide. The oligonucleotides can be synthesized to include unnatural nucleotides. Labels, such as fluorescent labels and epigenetic structures such as methylated or hydroxymethylated cytosine bases because there is no requirement for enzymatic synthesis.

The ligation of oligonucleotides can be done on a large scale, for example at least one gram, preferably at least 10 grams, preferably at least 50 grams, preferably at least 100 grams, preferably at least 500 grams, preferably at least 1 kilogram, preferably at least 2 kilograms of product may be produced in a single reaction.

In one embodiment there is no requirement to purify the ligation products for the purpose of removing ligase enzymes.

The chemical ligation reaction can be initiated at any time by the addition of Cu(I) and will not occur at a measurable rate in the absence of Cu(I). Therefore, the participating oligonucleotides can be allowed to slowly anneal to each other or to a template and produce the correct construct before the reaction is initiated, thus avoiding the formation of incorrect products.

Methods of the present invention may be advantageous for the synthesis of large DNA constructs containing modified bases (e.g. epigenetic modifications) for altered gene expression, mutagenic modifications, degenerate sites to allow the synthesis of altered proteins and also internal fluorescent tags (e.g. on bases) to visualise DNA in cells at the single molecule level.

Methods of the present invention may be useful in attachment & fabrication via solid phases (oligo printing; 3D nanoassemblies); Possibilities in nanotechnology to produce covalently fixed DNA-nanoconstructs that can be purified and used as building blocks in the synthesis of larger nanoconstructs.

Methods and oligonucleotides of the present invention may be used in applications such as FISH (fluorescence in situ hybridization) to produce oligonucleotide probes with long tails with multiple fluorescent groups that will produce unique colors for applications such as chromosome paints, e.g. to analyse for translocations in cancer diagnostics. The long fluorescent tails may be synthesized separately and attached onto specific oligonucleotide probe sequences using the oligonucleotide joining methods of the present invention, so that all the probes for particular regions of a specific chromosome have a unique color and probes for other regions/chromosomes have different unique colors. The fluorescent tags could be used to join to oligonucleotide probes for other applications that require oligonucleotide probes.

Synthesis of oligonucleotide duplexes with ends capped (end-sealed duplexes) Single stranded oligonucleotides with an alkyne at one end and an azide at the other end can be click-ligated to produce end sealed cyclic duplexes with a triazole linker in one strand of the backbone of the duplex. The reaction produces "end sealed" duplexes with triazole linkers at each end of the duplex. Such oligonucleotides will typically have single stranded loops at each end (e.g. TTTT) or artificial loops (e.g. hexaethylene glycol). The sequence of the duplex can be chosen to be a binding site for a transcription factor. Alternatively, modified, mutagenic or epigenetic bases can be incorporated into an end sealed duplex such that it is a substrate for a DNA repair enzyme or another enzyme involved in DNA processing. End sealed duplexes can be used in vivo as decoys for enzymes such as those mentioned above. The advantages of this approach are:

Very short end sealed oligonucleotides (even those with only two base pairs) form stable duplexes under physiological conditions because the process of duplex formation is intramolecular. In contrast, the formation of normal duplexes is an intermolecular process and is therefore dependent on DNA concentration. Consequently end sealed duplexes have much higher thermal stability than normal duplexes and can therefore be shorter without separating into two unpaired strands.

Another consequence of the end sealing is that the two strands of the duplex cannot come apart in vivo as they are chemically linked (unlike normal duplexes).

Short oligonucleotides are more readily taken up into cells than long oligonucleotides. Hence end sealed duplexes are more likely to be delivered into cells as they can be much shorter and still be active as double stranded decoys.

End sealed duplexes have greater in vivo stability than normal duplexes because they do not have free ends that can be digested by DNase enzymes (3'- or 5'-exonuclease enzymes).

Moreover, the click ligation reaction can be performed on a large scale to provide decoys for potential therapeutic use. This would not be possible with enzymatic ligation due to the high cost of ligase enzymes.

BRIEF DESCRIPTION OF THE DRAWINGS

There now follows by way of example only a detailed description of the present invention with reference to the accompanying drawings, in which;

FIG. 23 shows sequence alignment of the click triazole BLA gene with the normal template from the experiments with normal *E. coli*. The restriction sites are shown in yellow, while the position of the click linked nucleotides is shown in red. The two sequences are identical indicating the biocompatibility of the triazole linkers;

FIG. 24 shows growth of colonies in the UvrB deficient strain of *E. coli* JW0762-2. LB agar plates were incubated at 37° C. overnight and colonies were counted using Gel Doc XR+ system and Quantity One Software (both from Bio-Rad Laboratories). Number of colonies from normal backbone=152, triazole backbone=142, negative control (water) =18. Number of plates counted=28;

FIG. 25 shows Sequence alignment of the triazole and normal BLA fragments from the experiments with repair-deficient (ΔUvrB) *E. coli* JW0762-2. The restriction sites are shown in yellow, while the position of the triazole linked nucleotides is shown in red. Representative sequences are shown from 21 colonies transformed with the plasmid containing the click triazole BLA insert and 10 colonies from the same strain transformed with the plasmid containing the normal BLA insert. The T7-luciferase plasmid containing the normal BLA insert was also sequenced (plasmid control). All sequences were identical indicating that DNA repair does not play a role in the observed biocompatibility;

DETAILED DESCRIPTION

Figure 1:
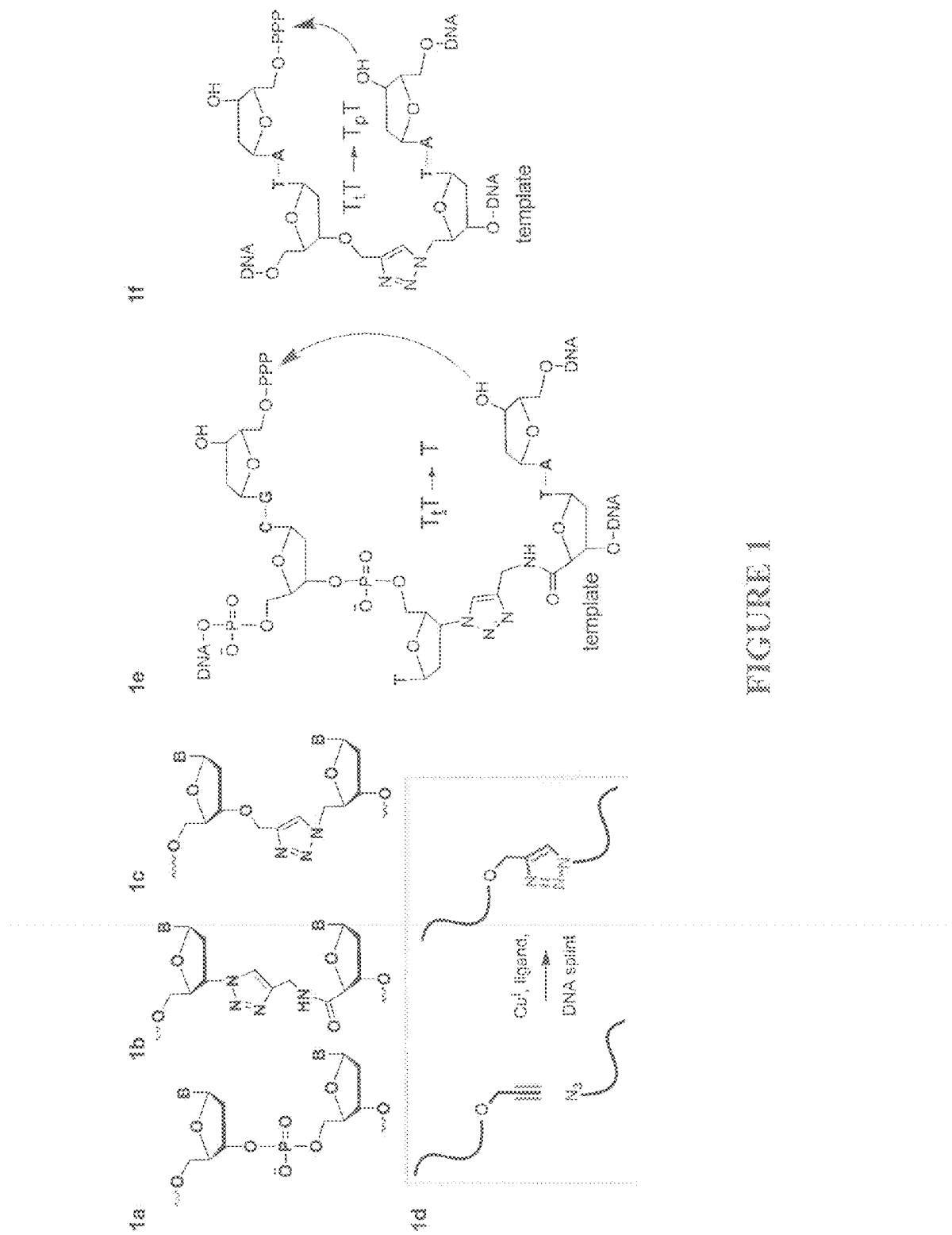
FIG. 1 shows DNA linkage structures: 1*a*. Canonical DNA, 1*b*. Previous triazole DNA analogue described in El-Sagheer et al., (2009), J Am Chem Soc 131, 3958-3964. 1*c*. Biocompatible triazole analogue, 1*d*. Click ligation to produce triazole DNA mimic 1*c*. 1*e*. Polymerases read through 1*b* using only one of the two thymines as a template base, i.e. $T_tT \rightarrow T$. (t=triazole). 1*f*. PCR copies the base sequence around the unnatural linkage 1*c* correctly.

Solid-phase DNA synthesis is an advanced technology that has led to pioneering discoveries in biology and nanotechnology. Although automated solid-phase phosphoramidite synthesis is highly efficient, the accumulation of modifications (mutations) and failure sequences caused by side-reactions and imperfect coupling imposes a practical limit of around 150 bases on the length of oligonucleotides that can be made. Consequently very long synthetic oligonucleotides are not suitable for use in biological applications that require sequence fidelity, so combinations of shorter sequences are normally used in PCR-mediated gene assembly. This enzymatic method of DNA synthesis has the intrinsic limitation that site-specific chemical modifications can only be introduced in the primer regions of the resulting constructs. Certain unnatural analogues can be inserted throughout the PCR amplicon via modified dNTPs, but this process is essentially uncontrolled and does not allow combinations of different modifications to be incorporated at specific loci. Therefore, for biological studies, important epigenetic and mutagenic bases such as 5-methyl dC, 5-hydroxymethyl dC and 8-oxo dG are normally put into short oligonucleotides and subsequently inserted into larger DNA strands by enzymatic ligation. Templated enzymatic ligation of oligonucleotides can be used to produce large DNA fragments, but this is best carried out on a small scale. In addition, some modified bases are not tolerated by ligase enzymes. Enzymatic methods of gene synthesis are extremely important in biology, but a purely chemical method for the assembly of large DNA molecules would be an interesting and valuable addition to current tools, with the advantages of scalability, flexibility and orthogonality.

It has proved challenging to achieve clean and efficient chemical ligation of canonical DNA, although significant progress has been made using cyanogen bromide as a coupling agent. An interesting alternative approach is to design a chemical linkage that mimics the natural phosphodiester group, and which can be formed in high yield in aqueous media from functional groups that are orthogonal to those naturally present in DNA.

Three key requirements of the strategy of the present invention are the use of functional groups that are highly stable in aqueous media, the ability to selectively initiate the ligation reaction only when participating oligonucleotides have been hybridized to complementary splints (to arrange the DNA strands in the desired order by templated pre-assembly), and the creation of a very stable backbone linkage. The present invention relates to a high-yielding DNA ligation method (click ligation) based on the CuAAC reaction. Click chemistry has previously been used in the nucleic acids field but previous DNA triazole linkages were not accurately read through by PCR. Amplification of the resulting modified DNA template caused the loss of one nucleotide at the site of click ligation. The consistently observed deletion mutation in the resulting PCR products indicated that this previous artificial DNA linkage was not an adequate mimic of a phosphodiester group and it does not behave like its natural counterpart. in vivo.

Embodiments of the present invention relates to the synthesis and properties of newly designed triazole phosphodiester mimics using oligonucleotides comprising alkyne or azide groups that can be readily prepared by standard phosphoramidite methods, and that are functional both in vitro, as substrates for DNA and RNA polymerases. It is the first example of a biocompatible artificial DNA linkage that can be formed efficiently by chemical ligation.

Synthesis and Assembly of Azide/Alkyne Oligonucleotides

Figure 2:
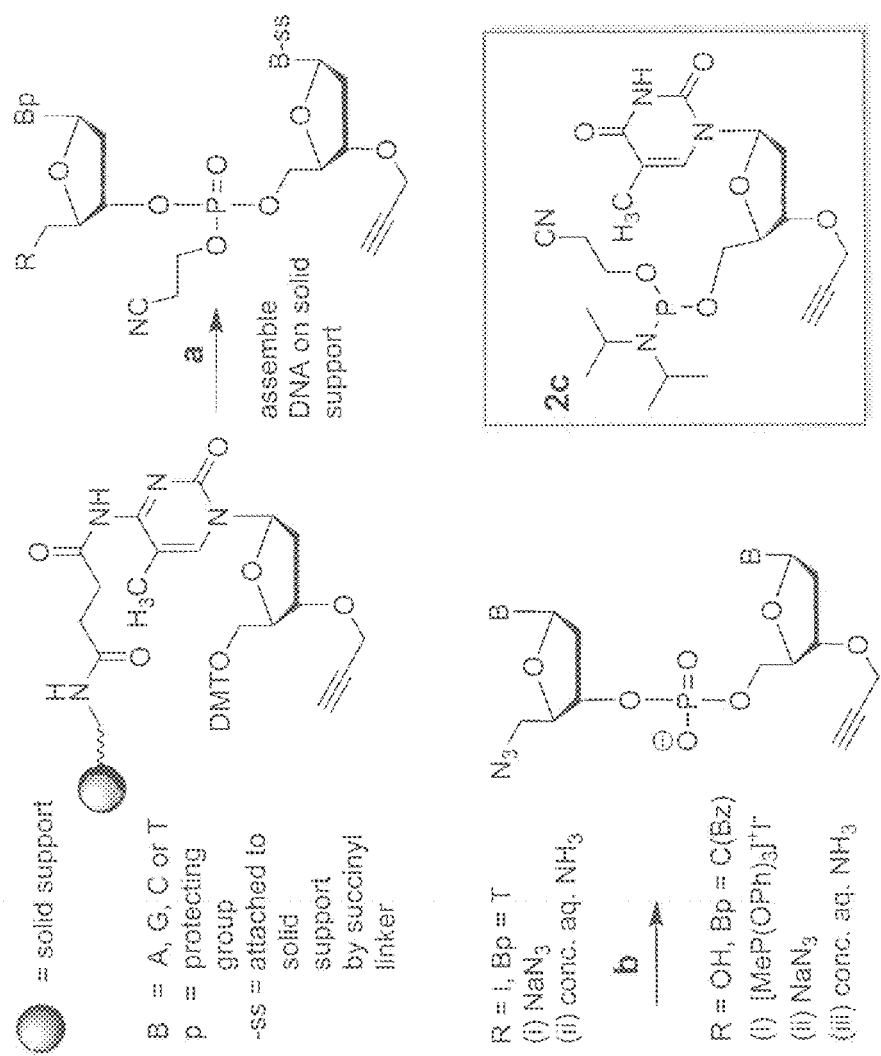
FIG. 2 shows a scheme for the synthesis of alkyne/azide oligonucleotides for use in click ligation and cyclization. 2*a*. Assembly of 3'-alkyne oligonucleotide. 2*b*. Conversion to 5'-azide. Oligonucleotides can be made with 5'-azide, 3'-alkyne or both. A dinucleotide is shown for clarity but the reactions have been carried out on oligonucleotides up to 150-mer in length. 2*c*. 3'-Propargyl dT introduced as final addition in reverse phosphoramidite assembly of DNA.

The triazole phosphodiester mimic of the present invention has the considerable advantage of being constructed from oligonucleotides made entirely by the phosphoramidite method, one bearing a 5'-azide functional group and the other a 3'-alkyne. The functionalised resin required for the solid-phase synthesis of oligonucleotides terminating with 3'-propargyl $^{Me}$dC (cytosine equivalent, (FIG. 2) was prepared from thymidine as previously described in El-Sagheer A H & Brown T (2010) New strategy for the synthesis of chemically modified RNA constructs exemplified by hairpin and hammerhead ribozymes. Proc. Natl. Acad. Sci. U.S.A. 107(35): 15329-15334. A polystyrene support was used to achieve high coupling yields and produce 100-mer oligonucleotides of the purity required for efficient click ligation. DNA strands containing 3'-propargyl dT were made from reverse phosphoramidites which required the synthesis of monomer 2c. The 5'-azide group was introduced in a 2-stage process (FIG. 2); the 5'-OH group of a normal support-bound oligonucleotide was first converted to 5'-iodo by reaction with methyl-triphenoxyphosphonium iodide (for oligonucleotides with 5'-dT this was simplified by direct incorporation of 5'-iodo thymidine phosphoramidite), then the resultant 5'-iodo oligonucleotides were reacted with sodium azide to complete the transformation. Oligonucleotides functionalised with both 3'-alkyne and 5'-azide were made by performing oligonucleotide synthesis on 3'-propargyl $^{Me}$dC resin then converting the 5'-terminus to azide as described above. In this study the bases on either side of the triazole linkage are thymine and cytosine (or 5-methylcytosine). This is an adequate combination for the synthesis of any large DNA strand by click ligation, but it may be possible to use the same methodology for other combinations of nucleosides.

Amplification of Click-DNA by Thermostable Polymerases

To investigate the compatibility of linkage 1c with thermostable polymerases, three 81-mer DNA templates were synthesized, each containing a single triazole linkage. PCR of these constructs produced amplicons that were faithful copies of the original sequence, with the T$_t$T, T$_t$C, $^{Me}$C$_t$T and $^{Me}$C$_t$C linkages being read through accurately ($_t$=triazole 1c). It is possible however, that PCR amplification of the chemically modified DNA might appear to be efficient even if read-through of the artificial linkage is a rare event. The ability of DNA polymerases to replicate through the triazole linkage was therefore evaluated more rigorously by linear copying of an 81-mer (Table 1) using Large Klenow fragment. The reaction was efficient and the full length product was obtained in less than 5 minutes.

Figure 3:
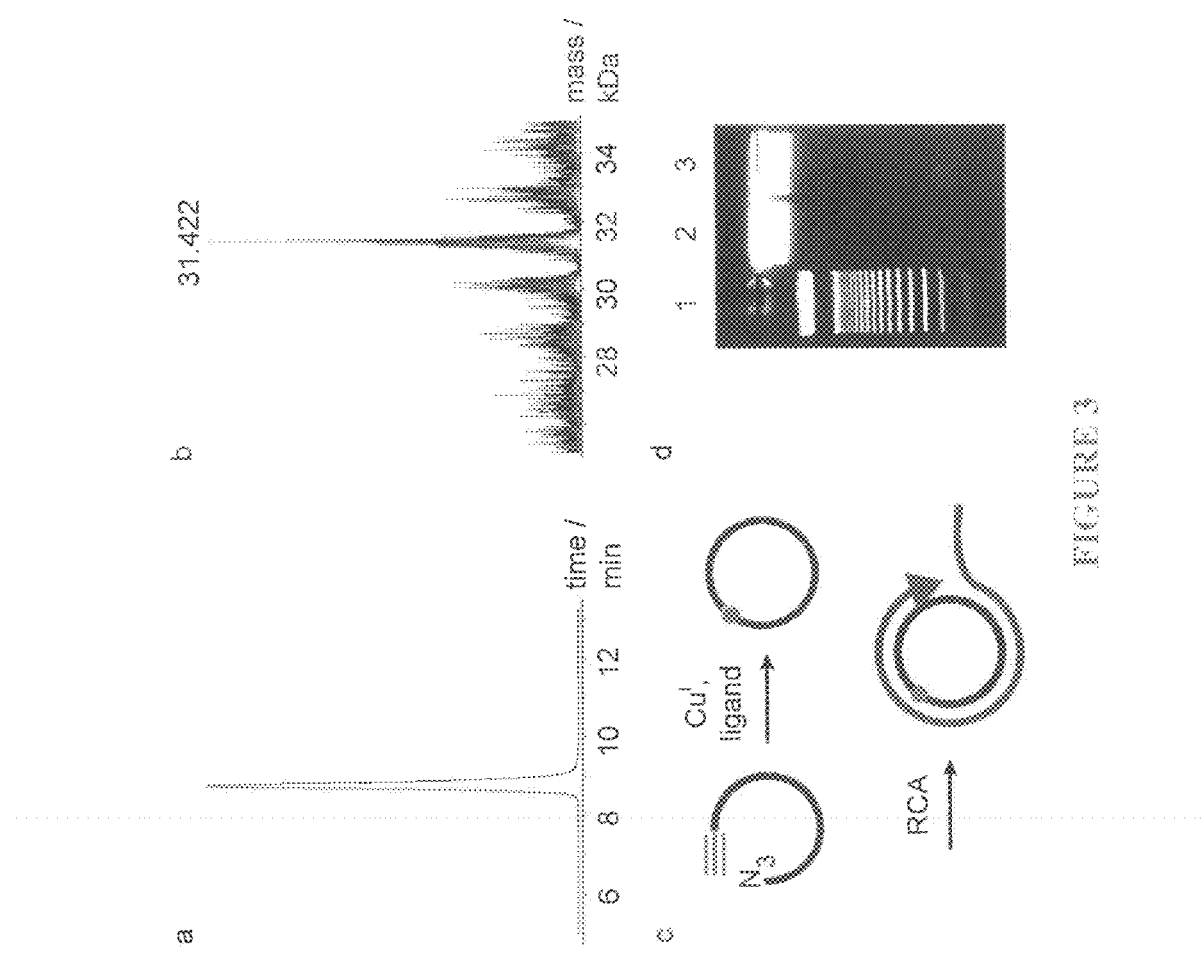
FIG. 3 shows cyclization and RCA of 5'-azide-3'-alkyne 100-mer. 3*a*. Reversed-phase HPLC (UV abs at 260 nm) and 3*b*. mass spectrum (ES$^-$) of cyclic 100-mer ODN-31, required; 31.423 kDa, found 31.422 kDa. 3*c*. Schematic of RCA reaction. 3*d*. RCA product from cyclic 100-mers using phi29 DNA polymerase. Lane 1; 50 bp DNA ladder, lanes 2 and 3; RCA of cyclic triazole ODN-31 and cyclic normal ODN-49 respectively.

Application of click DNA ligation to the synthesis of large linear DNA constructs requires oligonucleotides that are functionalised at both termini. Simultaneous ligation of three 11-mer oligonucleotides in the presence of a complementary 41-mer splint was evaluated. The click ligation reaction was clean and the product was characterised by ES mass spectrometry (calc. 10064, found 10064). The integrity of the terminal alkyne and azide is essential for efficient click ligation, so it was important to show that the large numbers of repeated steps employed in the synthesis of long oligonucleotides do not destroy these functional groups. This was confirmed by successfully cyclizing a 100-mer with 5'-azide and 3'-alkyne functionalities. The reaction proceeded smoothly in the absence of a complementary template oligonucleotide and the product was characterised by gel-electrophoresis and mass spectrometry (FIGS. 3a and b. Under similar conditions enzymatic cyclization failed, whereas in templated mode both the chemical and enzymatic cyclization reactions were successful.

Figure 4:
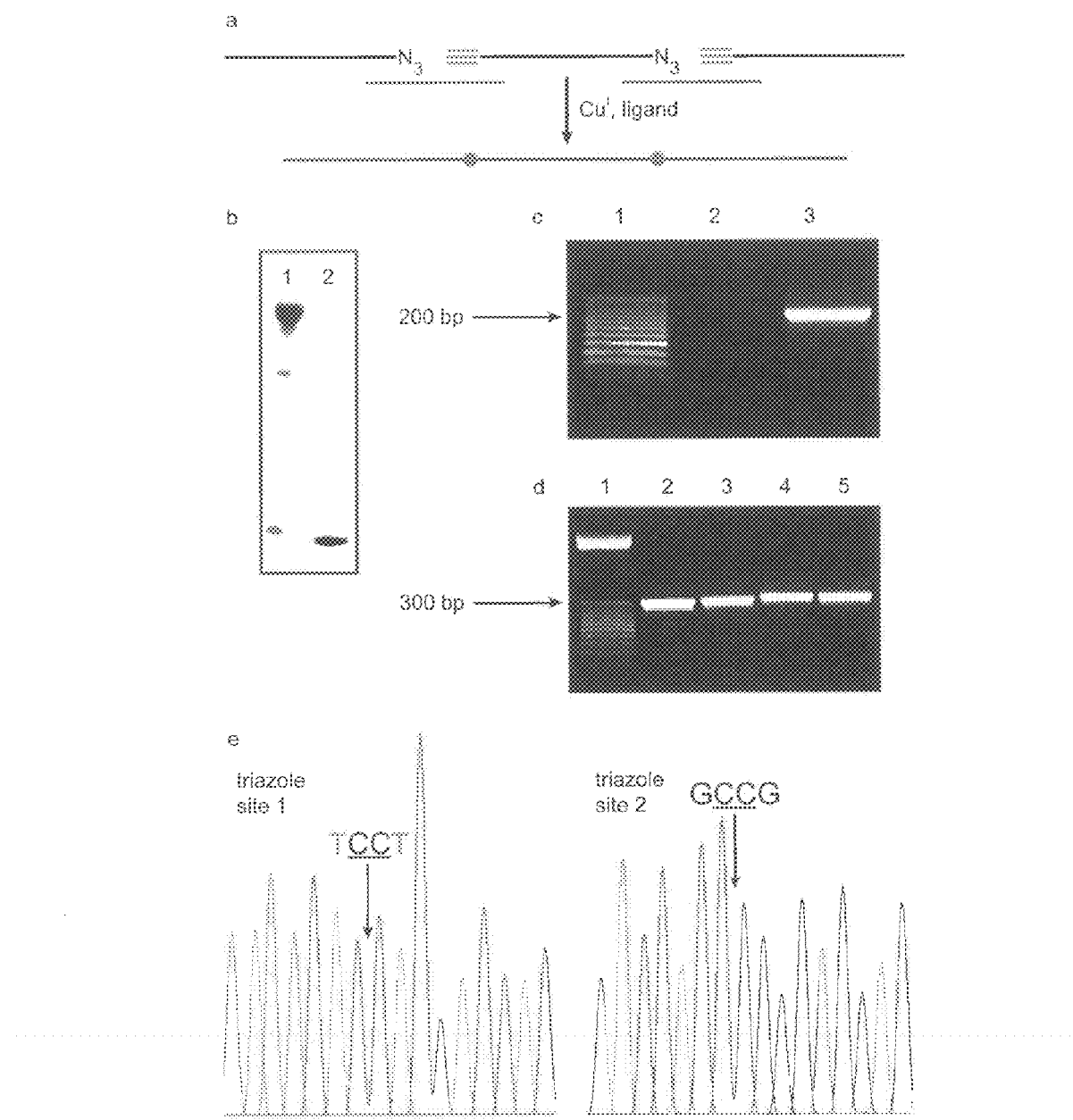
FIG. 4 shows PCR amplification of 210-mer and 300-mer click-ligated triazole DNA templates. 4a. Schematic representation of click ligation of three oligonucleotides. 4b. Click ligation reaction: Lane 1; crude reaction mixture to synthesize 210-mer template from three 70-mers, lane 2; starting oligonucleotide ODN-16 (8% polyacrylamide gel). 4c. PCR using 210-mer triazole template. Lane 1; 25 bp DNA ladder, lane 2; control PCR without click-ligated template, lane 3; PCR using 210-mer triazole template. 4d. PCR using 300-mer triazole template. Lane 1; 25 bp DNA ladder, lanes 2, 3; PCR using short primers ODN-26 and ODN-27, Lanes 4, 5; PCR using long primers ODN-28 and ODN-29. (2% agarose gels with ethidium staining). 4e. Sequencing data from 300-mer triazole amplicon showing that the base sequence of the template was replicated faithfully at the two ligation sites.

To demonstrate the utility of click ligation for the assembly of large DNA molecules, a 210-mer PCR template was assembled from three 70-mers, as well as a 300-mer from three 100-mer oligonucleotides. The oligonucleotides were designed to have an even distribution of A, G, C and T bases and to be devoid of secondary structure. The ligation products were purified by gel-electrophoresis and used as templates in PCR, after which the amplified regions were cloned, sequenced and found to be correct (FIG. 4). Thermostable polymerases with or without proofreading activity (Pfu and GoTaq respectively) read through the sequence around the click linkers to give the expected amplicons. In this study a total of four different base stacking steps ($Y_tY$, all possible combinations of pyrimidines) on either side of the triazole were examined in several different tetramer sequences (Table 1), and in all cases (134 clones) the bases encompassing the triazole linkages were replicated correctly. In addition to PCR, rolling circle amplification (RCA) of a cyclic 100-mer containing a triazole linkage were carried out using the highly processive phi29 polymerase. The cyclic template was produced in an intramolecular click ligation reaction of a 5'-azide-3'-alkyne oligonucleotide (Table 1). An essentially identical profile of phi29 RCA products was obtained from both normal and triazole cyclic templates (FIG. 3d), and long RCA products using GoTaq polymerase under standard PCR cycling conditions, by repeated read-through of the triazole linkage in a short timescale. The amplified RCA product was probed with a fluorescent HyBeacon to confirm that it was a true copy of the original template rather than a non-specific amplification product.

Biocompatibility of the Click Linker in E. coli

Figure 5:
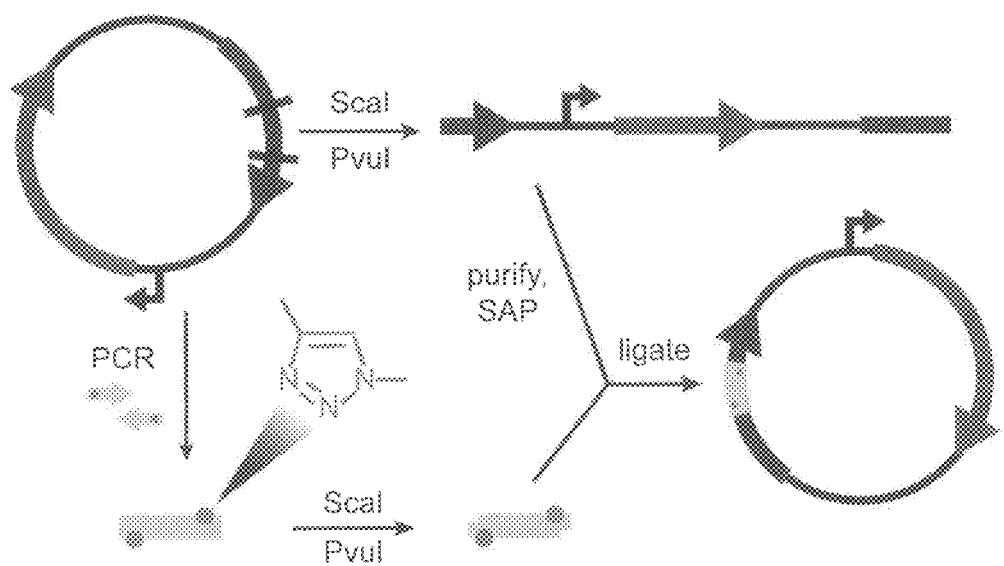
FIG. 5 shows assembly of a T7-Luciferase control plasmid containing click-DNA within its BLA gene. A region corresponding to the central part of BLA was PCR-amplified using oligonucleotide primers (ODN-39, ODN-41) containing triazole linkage 1c. The PCR product was ligated into the digested plasmid to give an intact construct containing triazole linkages on each strand of its BLA gene.
Figure 6:
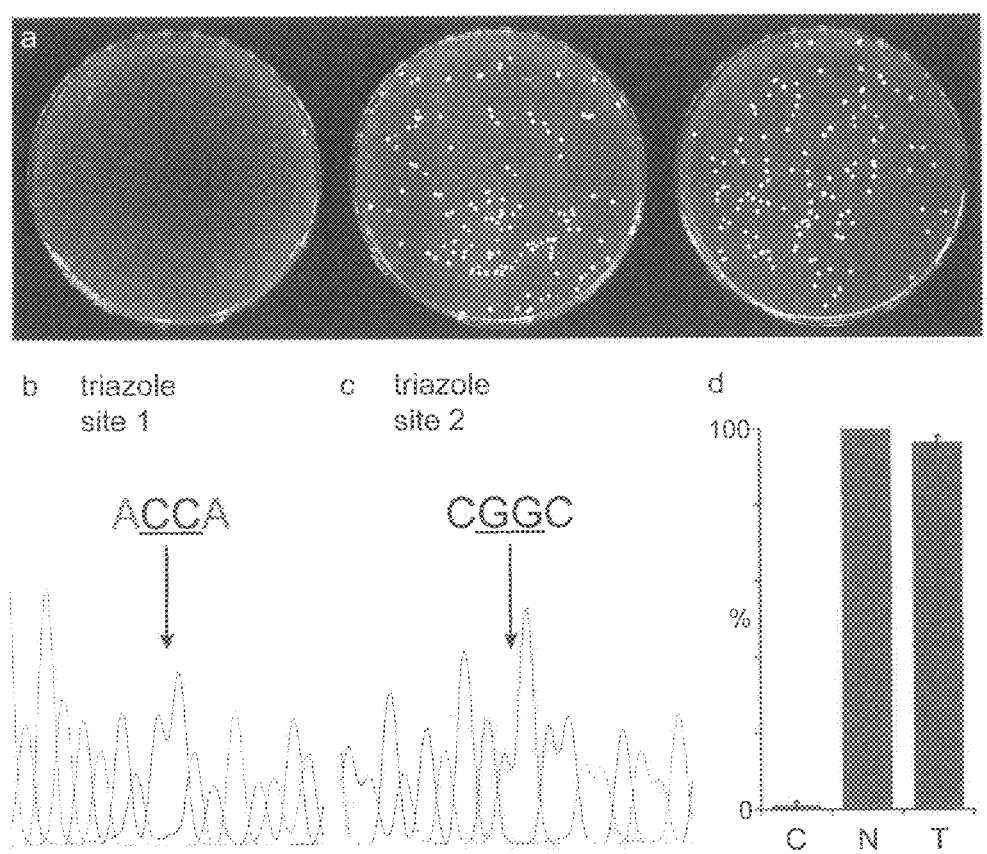
FIG. 6 shows biocompatability of click DNA in E. coli. 6a. The plate on the left is the negative control (no insert), the middle plate contains transformants of plasmids with the triazole DNA insert in its BLA gene (127 colonies), and the plate on the right is the native plasmid (129 colonies). 21 replicates of each plate were performed. 6b, c. Sequencing of the BLA gene from colonies in the triazole DNA plates. In 6c. the $^{Me}C_tC$ is contained on the complementary strand, therefore appearing as GG. 6d. Comparison of colony growth in the control (C), native (N) and triazole (T) plates. Triazole plates contained 96.5% of the colonies in the native plates (S.D.=1.6%) whereas the negative control was 1.1% (S.D.=1.0%).

Following the successful in vitro experiments the biocompatibility of the modified DNA was investigated in vivo within the cellular machinery of E. coli (FIG. 5) by constructing a plasmid containing a triazole linkage in each strand of its antibiotic marker gene. The triazole linkages were introduced via modified PCR primers that amplify a portion of the TEM-1 β-lactamase (BLA) gene between the ScaI and PvuI restriction sites. PCR with these primers yielded a product matching the middle section of BLA, containing $^{Me}C_tC$ near the 3' terminus of each strand. Electrophoresis of the amplicon showed it to be of the expected size and identical in length to that from the control PCR carried out with unmodified primers. The products of both PCR reactions (using unmodified and modified primers) as well as a plasmid containing the BLA gene (T7-Luciferase control, Promega Inc.) were digested with ScaI and PvuI restriction endonucleases. The digested plasmid (now lacking the region between ScaI and PvuI in its BLA gene) was gel-purified to remove the insert and undigested/singly digested plasmid, and treated with shrimp alkaline phosphatase to remove the phosphate monoesters from the 5'-termini to prevent self-ligation. The digested PCR products were then ligated into the linearized plasmid backbone via the matching ScaI and PvuI sites using T4 DNA ligase. A control ligation reaction was also set-up containing water in place of the insert to measure the level of ampicillin resistance arising from the presence of partially digested or undigested backbone. The resulting ligation mixtures were transformed into E. coli (NEB 5α) and grown on LB-agar plates containing 100 μg/mL of ampicillin (21 plates of each type). After overnight incubation at 37° C. the number of colonies from the triazole plasmids was 96.5% of the native, whereas the negative control was only 1.6% (FIG. 6). Plasmid was isolated and the BLA gene was sequenced from 50 of the surviving colonies on both the positive control and the triazole DNA plates. In all cases the base sequence at the $^{Me}C_tC$ linkage was copied correctly.

The survival and growth of colonies containing a triazole-modified antibiotic marker gene suggests that the sequence around the triazole linkage is amplified correctly by the E. coli polymerases. However, viability might also be maintained if the region surrounding the triazole modification was excised by the cellular DNA repair machinery via nucleotide excision repair (NER) and replaced by a phosphodiester linkage. This possibility was investigated using a UvrB-deficient strain of E. coli (JW0762-2). UvrB is a central component of NER, interacting with UvrA, UvrC, UvrD, DNA polymerase I and DNA during excision-repair. If the biocompatibility of the click DNA linker was a consequence of NER, repair-deficient colonies would not survive on selective media when transformed with the triazole plasmid. Transformation of the repair-deficient strain of E. coli with the triazole plasmid gave 93% of the number transformed with the native plasmid, and sequencing the BLA gene from 21 of the colonies revealed that the region around the triazole linkage was copied correctly in all cases. This strongly supports the hypothesis that NER does not make a significant contribution to the biocompatibility of the triazole linkages.

Rationale for Biocompatibility of Triazole Linkage in DNA

Figure 7:
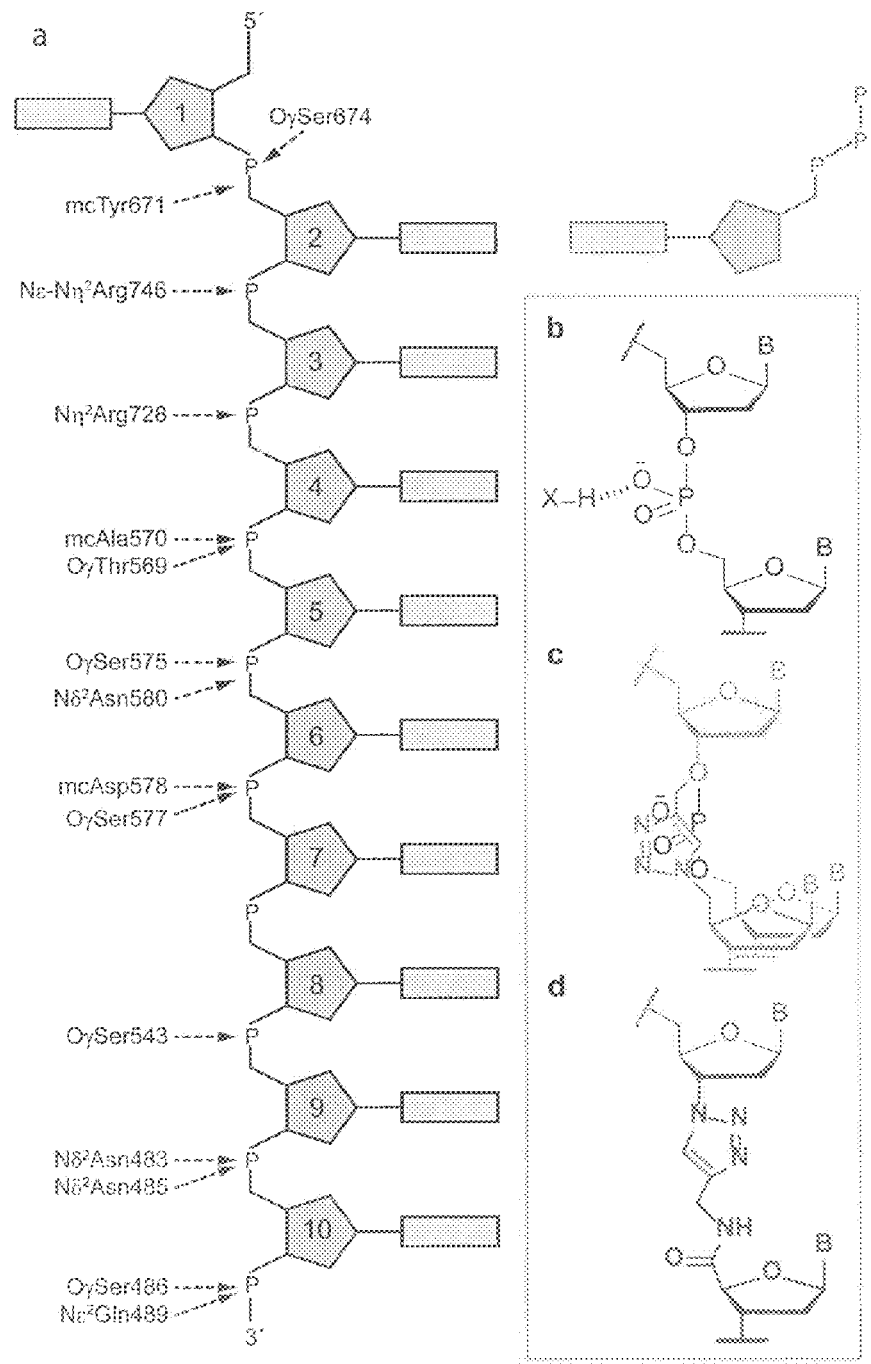
FIG. 7 shows Taq polymerase primer-template dNTP closed complex. 7a. Schematic of interactions between the phosphodiester linkages of the DNA template and amino acids of the enzyme. Only template strand is shown. mc=main chain. 7b. Canonical DNA; the majority of the interactions with the polymerase involve the branched phosphate oxygen atoms, few if any involve bridging oxygen atoms. 7c. Overlay of canonical DNA and triazole linkage 1c. The N2 and N3 atoms of triazoles are good hydrogen bond acceptors and in principle they could substitute for the phosphate oxygen atoms. 7d. Triazole linkage 1b showing the trans-configuration of the amide, with N2 and N3 of the triazole facing into the helix. Linkage 1b is significantly longer than 1a and 1c.
Figure 8:
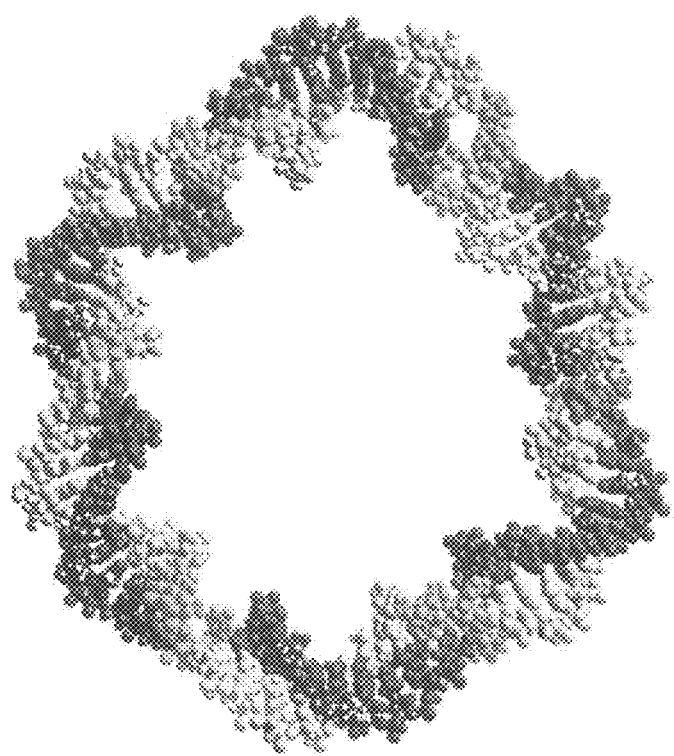
FIG. 8 shows a diagram of a DNA catanane. This is a double stranded closed circle of DNA which is not super-coiled.
Figure 9:
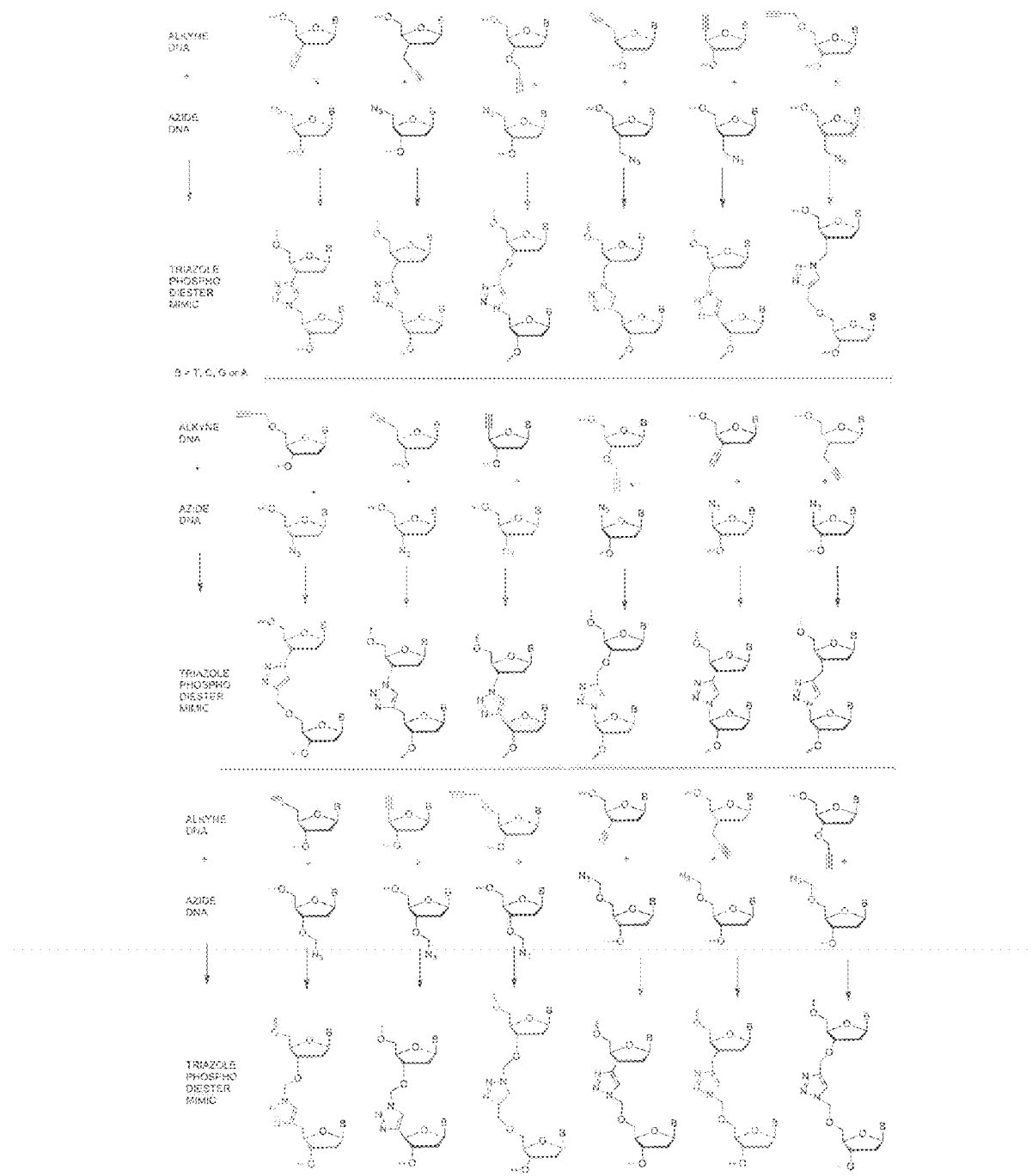
FIG. 9 shows examples of alkyne and azide pairs and the triazole phosphodiester mimics that they can form when reacted with each other. In each case only the deoxyribose that is linked to the alkyne or azide is shown but this deoxyribose may form part of an oligonucleotide. These examples show alkyne and azide pairs linked to deoxyribose but, it is also envisaged that these alkyne and azide groups can be linked to ribose groups of RNA in the same way. In each example B=a base, for example one of the five bases that occur in DNA and RNA (A, G, C, T and U) or a modified base. In the bottom line of each section triazole phosphodiester mimics that can be formed from the alkyne and azide pairs are shown.
Figure 10:
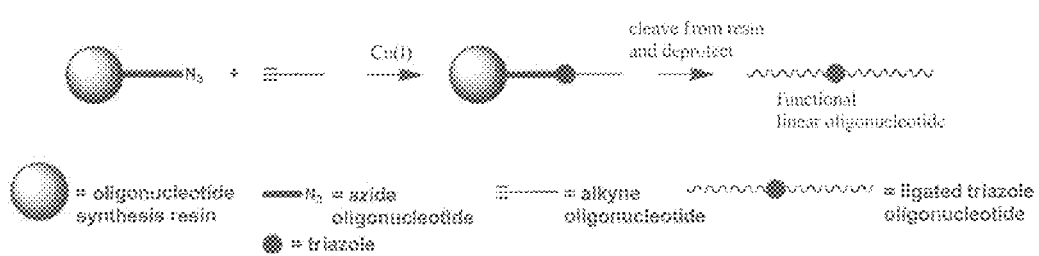
FIG. 10 shows a diagram of the reaction of an azide attached to an oligonucleotide and an alkyne attached to an oligonucleotide where the reaction takes place on a solid phase, in this case a synthesis resin. The azide oligonucleotide can be left on the synthesis resin on the oligonucleotide synthesis column and the alkyne oligonucleotide can be added to the resin in the presence of aqueous Cu(I) so that the reaction occurs on solid-phase in a non-templated mode. This has the advantage that an excess of the alkyne oligonucleotide can be used to make the reaction very efficient. The excess unreacted alkyne oligonucleotide can be washed away leaving the ligated oligonucleotide (containing the triazole linkage) on the resin. This can then be cleaved from the resin and deprotected using standard procedures. Alternatively the same procedure can be carried out with the alkyne oligonucleotide bound to the resin and the azide oligonucleotide in solution. The reaction may be carried out on solid phase in templated mode if modified nucleotide monomers are used that can be de-protected on the resin.
Figure 11:
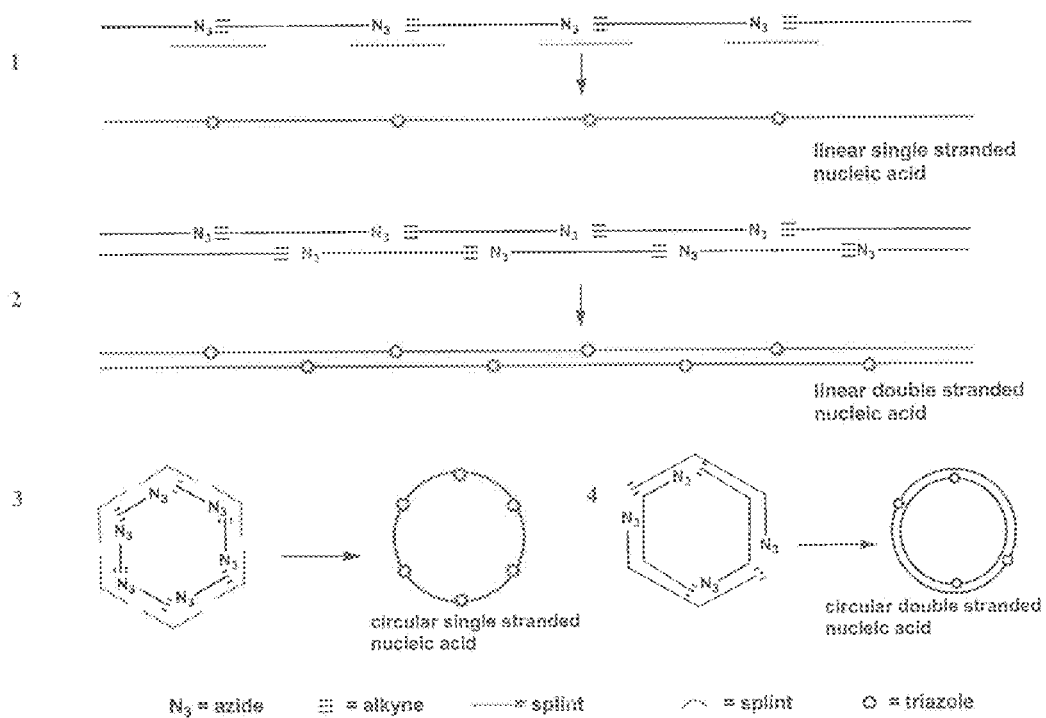
FIG. 11 shows four examples of schemes for making long oligonucleotides from one or more short oligonucleotides by ligating them together using the method of the present invention. In scheme one splints are used. These are short oligonucleotides that are complementary to two ends of oligonucleotides that will be ligated together. The splints ensure that the oligonucleotides are ligated together in the right order and orientation. In scheme 2 oligonucleotides with alkyne and/or azide groups attached are designed to have complementary overlapping ends, for example sticky ends. The overlapping complementary ends ensure that the oligonucleotides ligate to each other in the correct order and orientation. In scheme 3 complementary splints are used to construct a circular single stranded oligonucleotide. In scheme 4 oligonucleotides with overlapping complementary ends are used to construct a circular double stranded oligonucleotide. Several triazole linkages can be formed simultaneously if several alkyne/azide oligonucleotides are allowed to anneal and Cu(I) is added to the instigate the reaction. Alternatively the individual click reaction can be carried out sequentially. An oligonucleotide may have one alkyne or one azide group attached to one end or may have an alkyne group at each end, an azide group at each end or an alkyne group at one end and an azide group at the other end.
Figure 12:
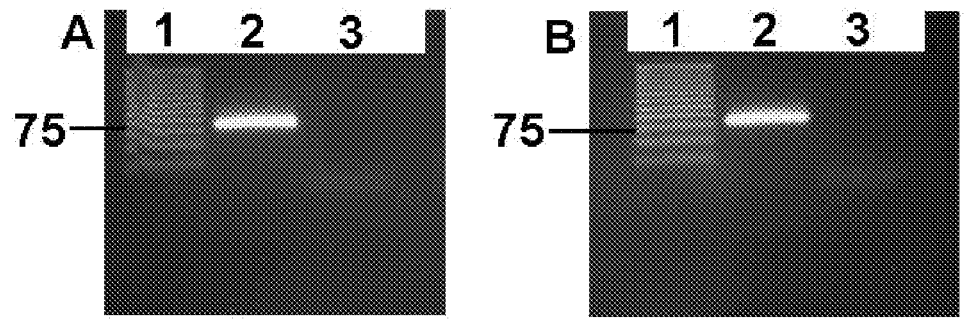
FIG. 12 shows gels with the results of PCR amplification of 81-mer click-ligated triazole DNA templates. A) Lane 1; 25 bp DNA ladder, lane 2; PCR reaction using template (81-mer) ODN-06 (5 ng) and short primers ODN-26 and ODN-27, lane 3; control sample with primers and without the template. B) Lane 1; 25 bp DNA ladder, lane 2; PCR reaction using template (81-mer) ODN-07 (5 ng) and short primers ODN-26 and ODN-27, lane 3; control sample with primers and without the template.
Figure 13:
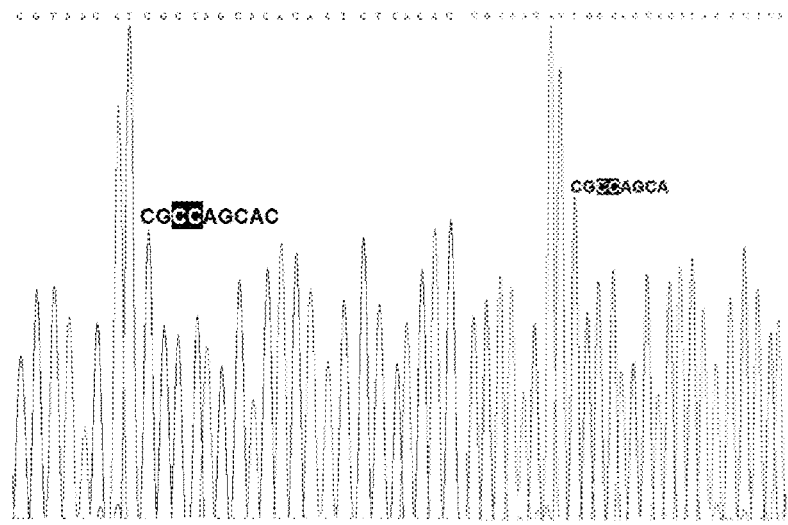
FIG. 13 shows sequencing data from (ODN-08) 81-mer triazole amplicon. Left, amplified using pfu DNA Polymerase. Right, amplified using GoTaq DNA Polymerase. The data shows that the templates were replicated faithfully at the ligation sites using both GoTaq or pfu DNA Polymerase.
Figure 14:
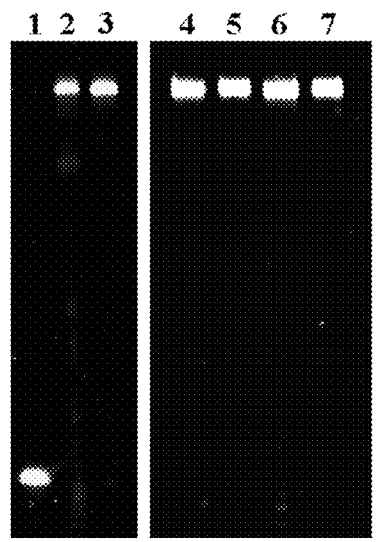
FIG. 14 shows linear copying of 81-mer click-ligated triazole DNA template ODN-08 and unmodified DNA template ODN-46 using DNA polymerase I, large Klenow fragment. Lane 1; 18-mer 5'-fluorescein primer ODN-47, lane 2; linear copying of ODN-08 (3 min), lane 3; linear copy of ODN-46 (3 min), lane 4; linear copy of ODN-08 (5 min), lane 5; linear copy of ODN-46 (5 min), lane 6; linear copy of ODN-08 (15 min), lane7; linear copy of ODN-46 (15 min). In all cases replication was complete within 5 min. 10% polyacrylamide gel, visualised by fluorescence.
Figure 15:
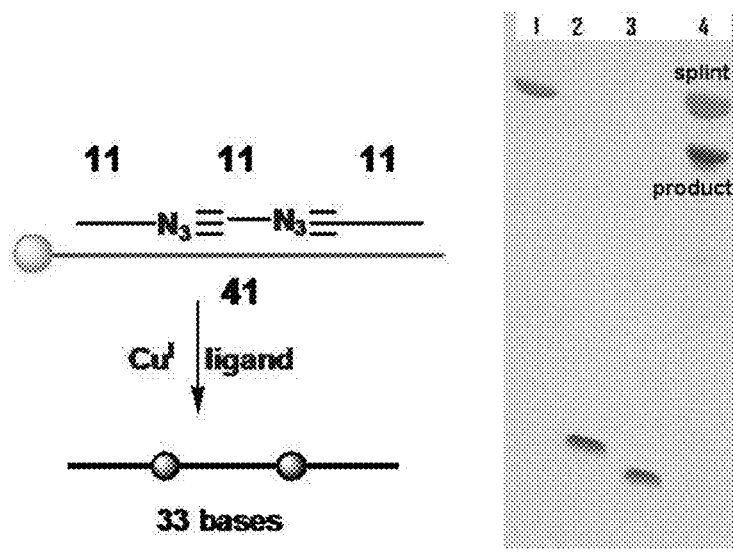
FIG. 15 shows templated double click ligation to synthesize the 33-mer template. 20% polyacrylamide gel for the double click ligation reaction of three short oligonucleotides. Lane 1; splint ODN-13, lane 2; alkyne ODN-09, lane 3; azide ODN-11, lane 4; click reaction mixture.
Figure 16:
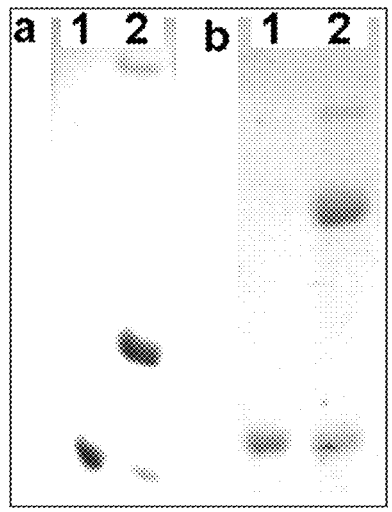
FIG. 16 shows successful non-templated click cyclization of oligonucleotides. 8% polyacrylamide gel. a) Lane 1; linear ODN-14 (70-mer), lane 2; cyclization reaction mixture. b) Lane 1; linear ODN-30 (100-mer), lane 2; cyclization reaction mixture.
Figure 17:
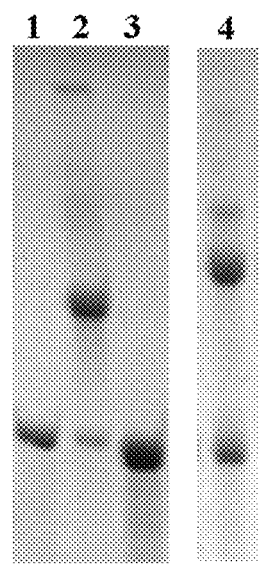
FIG. 17 shows a comparison of enzymatic and click cyclization of 100-mer oligonucleotides. Lane 1; control linear ODN-48, lane 2; successful templated enzymatic cyclization of ODN-48, lane 3; attempted non-templated enzymatic cyclization of ODN-48, lane 4; successful templated click cyclization of ODN-30. In templated reactions ODN-50 was used as the splint.
Figure 18:
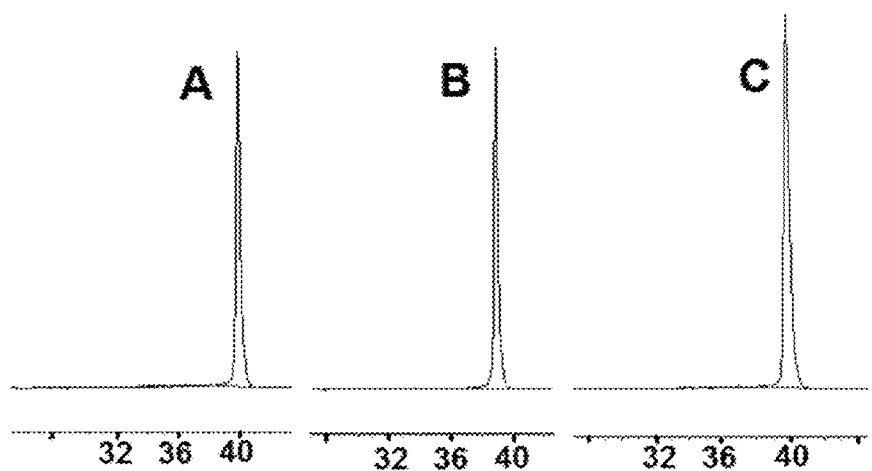
FIG. 18 shows Capillary Electrophoresis (CE) analysis of long oligonucleotides. The purity of the oligonucleotides was confirmed by injection of 0.4 OD/100 ssDNA 100-R Gel, Tris-Borate-7 M Urea (Kit No 477480) on a Beckman Coulter P/ACE™ MDQ Capillary Electrophoresis system using 32 Karat software. UV-254 nm, inject-voltage 10.0 kv and separation-voltage 9.0 kv (45.0 min duration). X-axis is time (min), Y-axis is UV absorbance at 254 nm. Oligonucleotides A) ODN-14, B) ODN-16, C) ODN-15.
Figure 19:
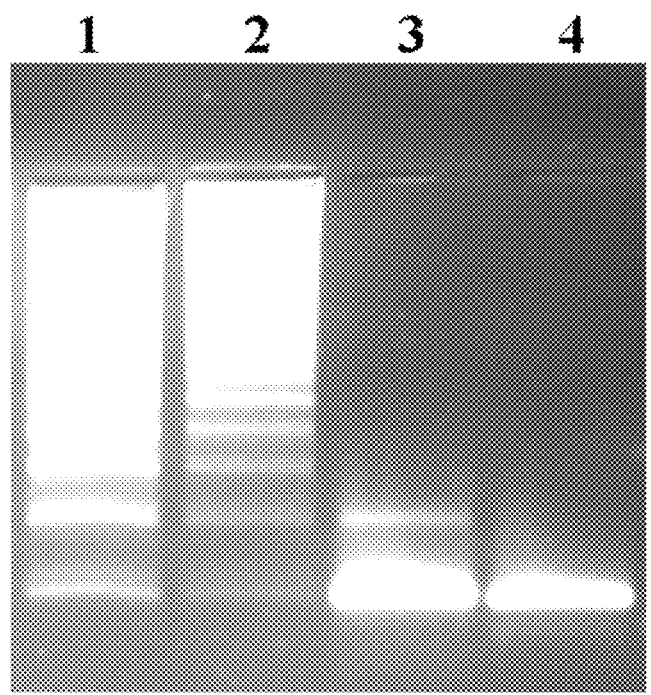
FIG. 19 shows an RCA of cyclic triazole ODN-31 and unmodified cyclic control ODN-49 using GoTaq DNA polymerase. Lane 1; RCA product of cyclic ODN-31, lane 2; RCA product of cyclic ODN-49, lane 3; control product of linear ODN-30, lane 4; control product of linear ODN-48.
Figure 20:
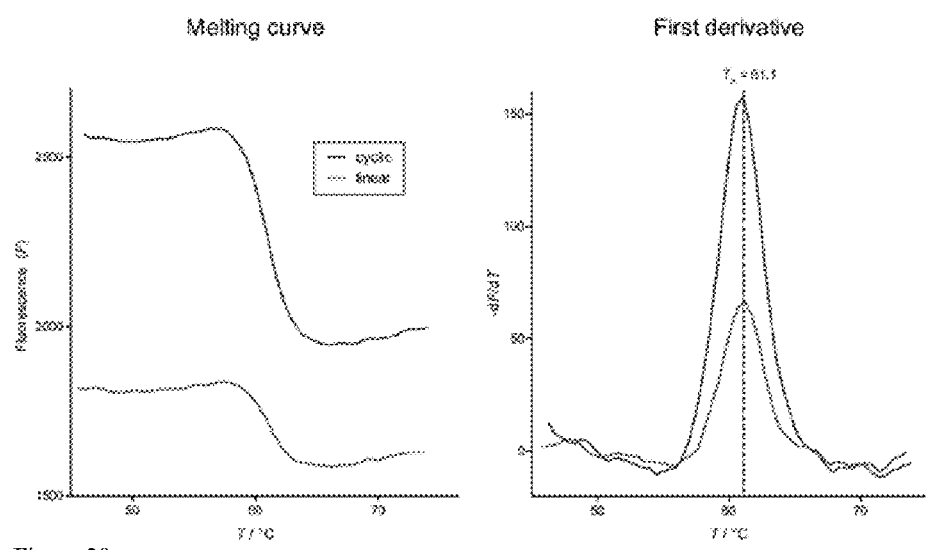
FIG. 20 shows melting curves obtained by probing the rolling cycle amplification product with a HyBeacon. Melting curves and derivatives were obtained by probing the asymmetric PCR products of linear ODN-30 and the GoTaq RCA product of cyclic ODN-31 using HyBeacon ODN-34. Genie I instrument (Optigene, UK). Tm=61.1° C. for both linear and cyclic products.

The ability of DNA polymerases to accurately synthesize a complementary copy of an artificial DNA linkage that bears limited structural resemblance to a natural phosphodiester may seem surprising. However, without wishing to be bound by theory, the X-ray structure of the Klenow fragment of Taq polymerase (Klentaq-1) with double stranded DNA at its active site provides some insight into the underlying mechanism of this phenomenon. In this structure there are several polar interactions between the enzyme and the phosphodiester groups of the DNA template strand that are consistent with hydrogen bonding (FIG. 7a). As the polymerase passes through the chemically modified template-primer complex, only one of the ten template nucleotides bound to the enzyme at any given time can encompass a triazole. Hence a maximum of only two interactions can be disrupted by the modification. In addition, some enzyme binding at the triazole site could still occur, as the triazole moiety has a large dipole moment and well-characterised hydrogen bond acceptor capacity. The requirement for dynamic and non-specific binding between DNA and the enzyme might also explain why the presence of triazole linkage 1c does not compromise fidelity during PCR amplification. A similar picture of enzyme template binding emerges from the structure of DNA bound to Taq polymerase, a version of the enzyme that has 3'-exonuclease activity.

Linkage 1c with its 3'-oxygen, 5'-methylene and greater conformational flexibility may be a closer analogue of a natural phosphodiester than 1b. In contrast to 1c, it is apparent that triazole 1b alters the characteristics of the DNA sufficiently to prevent faithful replication. The thymine base on the 5'-side of the triazole may not be presented at the polymerase domain in a suitable orientation to base pair with the incoming dATP, so the only option is for replication to continue from the next available template base (FIG. 1e). In addition, linkage 1b is by no means an obvious phosphodiester surrogate in terms of H-bonding acceptor capacity, so its binding to the polymerase may be compromised. The normally favoured trans-configuration at the amide bond, and the extended length of this linkage, may not allow the N2 and N3 atoms of the triazole to substitute for phosphodiester oxygen atoms (FIG. 7d).

Regardless of the detailed mechanisms, the results indicate that the artificial DNA linker is remarkably biocompatible. The high-resolution structure of a DNA duplex containing this triazole linkage shows its effects on DNA conformation and dynamics and explains its biocompatibility (Dallmann, A., A. H. El-Sagheer, et al. (2011). "Structure and Dynamics of Triazole-Linked DNA: Biocompatibility Explained." Chemistry-A European Journal 17(52): 14714-14717

Materials and Methods

Experimental

All reagents were purchased from Aldrich, Avocado, Fluka, Proligo, Applied Biosystems or Link Technologies and used without purification with the exception of THF (distilled over sodium wire and benzophenone), DCM, di-isopropylethylamine (DIPEA) and pyridine (distilled over calcium hydride). Chemical transformations were carried out under an atmosphere of argon using oven-dried glassware. NAP gel-filtration columns were purchased from GE Healthcare and used according to the manufacturer's instructions. Column chromatography was carried out under argon pressure using Fisher scientific DAVISIL 60A (35-70 μm) silica. Thin layer chromatography was performed using Merck Kieselgel 60 F24 plates (0.22 mm thickness, aluminum backed). 31P NMR spectra were recorded on a Bruker AV300 spectrometer at 121 MHz and externally referenced to 85% phosphoric acid in deuterated water. Low-resolution mass spectra were recorded using the electrospray technique on a Fisons VG platform instrument mass spectrometer in acetonitrile (HPLC grade). Electrospray MS of oligonucleotides were recorded in water using a Fisons VG platform mass spectrometer or on a Bruker micrOTOF™ II focus ESI-TOF MS instrument in ES– mode. Data were processed using MaxEnt.

3'-Propargyl thymidine-5'-O-(2-cyanoethyl-N,N-diisopropyl)phosphoramidite 2c

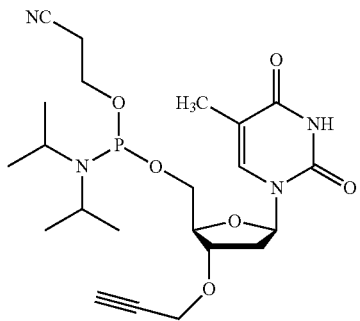

3'-Propargyl thymidine (1, 2) (0.43 g, 1.54 mmol) was dissolved in THF (10 mL) under an atmosphere of argon. DIPEA (0.66 mL, 3.85 mmol) was added followed by 2-cyanoethyl-N,N-diisopropylchlorophosphoramidite (0.41 mL, 1.78 mmol) dropwise. The reaction mixture was left to stir at room temperature for 2 hr and the volume of the solvent was then reduced to 3 mL by flushing argon through the reaction mixture. DCM (40 mL) was added and the mixture was transferred under argon into a separating funnel and washed with degassed saturated aqueous potassium chloride (20 mL). The organic layer was separated, dried over sodium sulfate, filtered and the solvent was removed in vacuo. After purification by silica gel column chromatography under argon (60:40 ethyl acetate:hexane, 0.5% pyridine) the product (2c) was isolated as a white foam (0.65 g, 88%).

$^1$H NMR for the two diastereomers
δH (300 MHz, CD3CN) 9.23 (2H, bs, 2×NH), 7.56, 7.43 (2H, d, J=1.1 Hz, 2×H-6), 6.15 (2H, dd, J=8.0, 5.9 Hz, 2×H'-1), 4.32 (2H, m, 2×H'-3), 4.21 (4H, d, J=2.7 Hz, 2× propargyl-CH2), 4.13 (2H, m, 2×H-4'), 3.83 (8H, m, 2×H'-5 and 2×P—O—CH2), 3.63 (4H, m, 2×[CH(CH3)2] 2) 2.74 (2H, t, J=2.7 Hz, 2× alkyne-H), 2.66 (4H, t, J=6.0 Hz, 2×CH2-CN), 2.35 (2H, m, 2×H'-2), 2.12 (2H, m, 2×H'-2), 1.85, 1.84 (6H, d, J=1.1 Hz, 2× thymidine-CH3), 1.21, 1.20, 1.19, 1.18, 1.16 (24H, s, 8× isopropyl-CH3) δP (121 MHz, CD3CN) 149.9, 149.6; m/z LRMS [ES+, MeCN], 503 (M+Na+, 100%).

General Method for Oligonucleotide Synthesis and Purification

Standard DNA phosphoramidites, solid supports and additional reagents were purchased from Link Technologies and Applied Biosystems. Oligonucleotides were synthesized on an Applied Biosystems 394 automated DNA/RNA synthesizer using a standard 0.2 or 1.0 μmole phosphoramidite cycle of acid-catalyzed detritylation, coupling, capping, and iodine oxidation. Stepwise coupling efficiencies and overall yields were determined by the automated trityl cation conductivity monitoring facility and in all cases were >98.0%. All β-cyanoethyl phosphoramidite monomers were dissolved in anhydrous acetonitrile to a concentration of 0.1 M immediately prior to use. The coupling time for normal A, G, C, and T monomers was 35 sec, whereas the coupling time for the reverse amidites was 180 sec. Alkyne phosphoramidite monomer 2c and other non-standard monomers were coupled for 360 sec. Cleavage of oligonucleotides from the solid support and deprotection was achieved by exposure to concentrated aqueous ammonia solution for 60 min at room temperature followed by heating in a sealed tube for 5 hr at 55° C. The oligonucleotides were purified by reversed-phase HPLC on a Gilson system using an XBridge™ BEH300 Prep C18 10 μM 10×250 mm column (Waters) with a gradient of acetonitrile in ammonium acetate (0% to 50% buffer B over 30 min, flow rate 4 mL/min), buffer A: 0.1 M ammonium acetate, pH 7.0, buffer B: 0.1 M ammonium acetate, pH 7.0, with 50% acetonitrile. Elution was monitored by UV absorption at 305 or 295 nm. After HPLC purification, oligonucleotides were desalted using NAP-10 columns and analyzed by gel electrophoresis.

Synthesis of 3'-alkyne and 5'-azide oligonucleotides i) Synthesis of 3'-alkyne oligonucleotides

3'-Alkyne oligonucleotides were synthesized using the 3'-propargylthymidine phosphoramidite monomer 2c and assembling the required sequence in the 5' to 3'-direction using the 3'-O-(4,4'-dimethoxytrityl)deoxyribonucleoside-5'-phosphoramidites of A, G, C and T (reverse phosphoramidites, Link Technologies) or by the attachment of 5'-O-(4, 4'-dimethoxytrityl)-3'-O-propargyl-5-methyl-deoxycytidine to solid support (33 μmole/g loading, AM polystyrene, Applied Biosystems) according to the published method in A. H. El-Sagheer et al. Proc. Natl. Acad. Sci. USA, 2010, 107 (35):15329-15334. The resin was packed into a twist column (Glen Research) then used to assemble the required sequence in the 3'- to 5'-direction by standard phosphoramidite oligonucleotide synthesis. The oligonucleotides were then cleaved, deprotected and purified as described above.

ii) Synthesis of 5'-azide oligonucleotides

Oligonucleotides were assembled on the 0.2 or 1.0 μmole scale (trityl-off) as described in the general method (above) with normal 5'-HO-dC, 5'-HO-dT (or with 5'-iodo-dT using the commercially available 5'-iodo dT monomer (from Glen Research). To convert the 5'-hydroxyl group to 5'-iodo the protected oligomers attached to the synthesis column were treated with a 0.5 M solution of methyltriphenoxyphosphonium iodide in DMF (1.0° mL) which was periodically passed through the column via two 1 mL syringes over 15 min at room temperature. The column was then washed several times with dry DMF. To convert the 5'-iodo (dT or dC) to 5'-azido (dT or dC), sodium azide (50 mg) was suspended in dry DMF (1 mL), heated for 10 min at 70° C. then cooled down and the supernatant taken up into a 1 mL syringe, passed back and forth through the column then left at room temperature overnight (or for 5 hr at 55° C.). The column was then washed with DMF and acetonitrile and dried by the passage of a stream of argon gas. The resultant 5'-azide oligonucleotide was cleaved from the solid support, deprotected and purified as described above.

iii) Synthesis of 3'-alkyne-5'-azide oligonucleotides

5'-O-(4,4'-Dimethoxytrityl)-3'-O-propargyl-5-methyldeoxycytidine on polystyrene solid support was packed into a twist column (Glen Research) and used to assemble the required sequence in the 3'- to 5'-direction (standard phosphoramidite oligonucleotide synthesis) with 5'-iodo dT, 5'-HO-dT or 5'-HO-dC at the 5'-end. The 5'-hydroxyl or iodo groups were then converted to azide using the conditions described above for the synthesis of the 5'-azide oligonucleotides.

Click DNA Ligation

Non-Templated Click Ligation for the Synthesis of 81-mer DNA Templates

A solution of $Cu^1$ click catalyst was prepared from tris-hydroxypropyltriazole ligand (0.7 µmol in 0.2 M NaCl, 22.0 µL), sodium ascorbate (1.0 µmol in 0.2 M NaCl, 2.0 µL) and CuSO4.5H2O (0.1 µmol in 0.2 M NaCl, 1.0 µL). The resulted $Cu^1$ solution was added to the two oligonucleotides (alkyne and azide) (5.0 nmol of each) in 0.2 M NaCl (25 µL). Reagents were removed using a NAP-10 gel-filtration column (GE Healthcare) and the ligated product was analysed and purified by denaturing 8% polyacrylamide gel electrophoresis.

Templated Double Click Ligation to Synthesize the 33-mer Template

Oligonucleotides (10.0 nmol of each) in 0.2 M NaCl (2.45 mL) were annealed by heating at 90° C. for 5 min, cooled slowly to room temperature and kept overnight at 4° C. A solution of $Cu^1$ click catalyst was prepared from tris-hydroxypropyltriazole ligand (4) (2.8 µmol in 0.2 M NaCl, 38.0 µL), sodium ascorbate (4.0 µmol in 0.2 M NaCl, 8.0 µL) and $CuSO_4.5H_2O$ (0.4 µmol in 0.2 M NaCl, 4.0 µL). This solution was added to the annealed oligonucleotides and the reaction mixture was kept at 0° C. for 1 hr, then at room temperature for a further 1 hr. Reagents were removed using a NAP-25 gel-filtration column and the ligated DNA was analysed and purified by denaturing 20% polyacrylamide gel electrophoresis.

Templated Double Click Ligation to Synthesize the 210-mer and 300-mer Templates

Oligonucleotides (5.0 nmol of each) in 0.2 M NaCl (475 µL) were annealed by heating at 90° C. for 5 min then cooled slowly to room temperature (2 hr) after which the temperature was maintained at 0° C. for 15 min. A solution of $Cu^1$ click catalyst was prepared from tris-hydroxypropyltriazole ligand (1.4 µmol in 0.2 M NaCl, 20.0 µL), sodium ascorbate (2.0 µmol in 0.2 M NaCl, 4.0 µL) and $CuSO_4.5H_2O$ (0.2 µmol in 0.2 M NaCl, 2.0 µL). This solution was added to the annealed oligonucleotides and the reaction mixture was kept at 0° C. for 30 min, then at room temperature for 2 hr. Reagents were removed using NAP-10 gel-filtration column and the ligated DNA was analysed and purified by denaturing 8% polyacrylamide gel electrophoresis.

Synthesis of the Forward and Reverse Triazole BLA Gene PCR Primers

Figure 21:
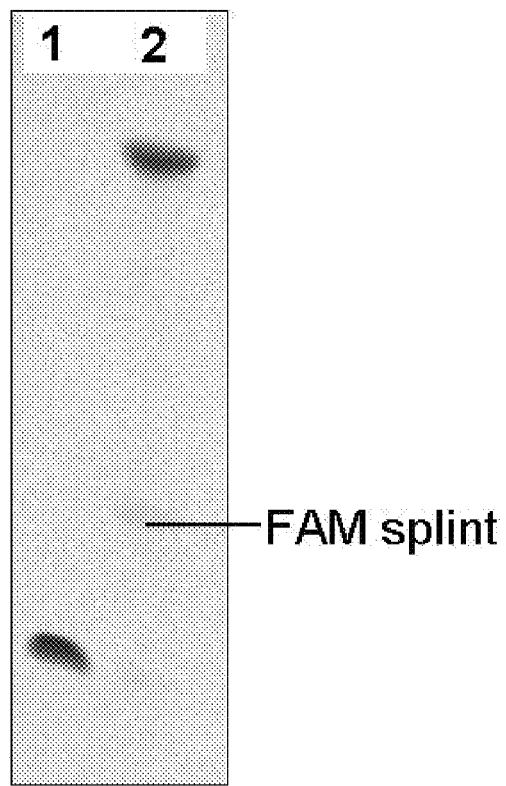
FIG. 21 shows the results of click synthesis of BLA PvuI reverse triazole primer 20% polyacrylamide gel. Lane 1; azide oligonucleotide ODN-38, lane 2; click reaction mixture.
Figure 22:
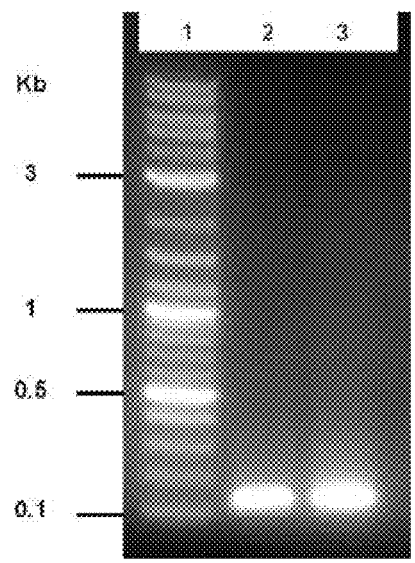
FIG. 22 shows the PCR product of the BLA fragment with triazole and normal oligonucleotides. Lane 1; DNA ladder in Kb; lane 2; amplification of BLA fragment using normal oligonucleotides, lane 3; amplification of BLA fragment using triazole oligonucleotides. 2% agarose gel.
Figure 26:
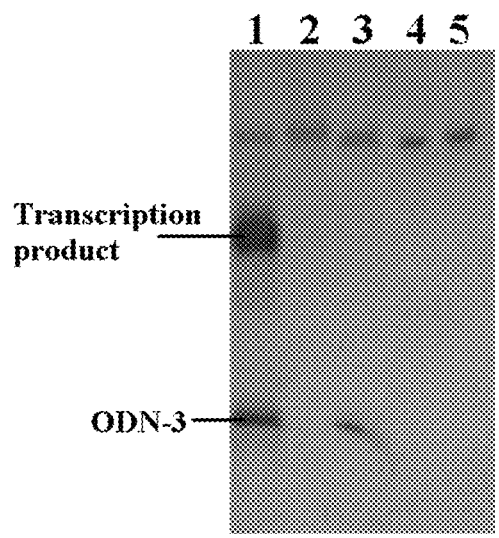
FIG. 26 shows a 10% polyacrylamide gel for transcription of 83-mer unmodified and click templates with the modification in the coding region (ODN-11) or in the promoter region (ODN-12). Lane 1: transcription using 83-mer click template (ODN-11) and 35-mer short coding strand (ODN-3); lane 2: attempted transcription using 83-mer click template (ODN-12) and 83-mer long coding strand (ODN-1); lane 3: attempted transcription using click template (ODN-12) and short coding strand (ODN-3); lane 4: control click template (ODN-11); lane 5: control click template (ODN-12)
Figure 27:
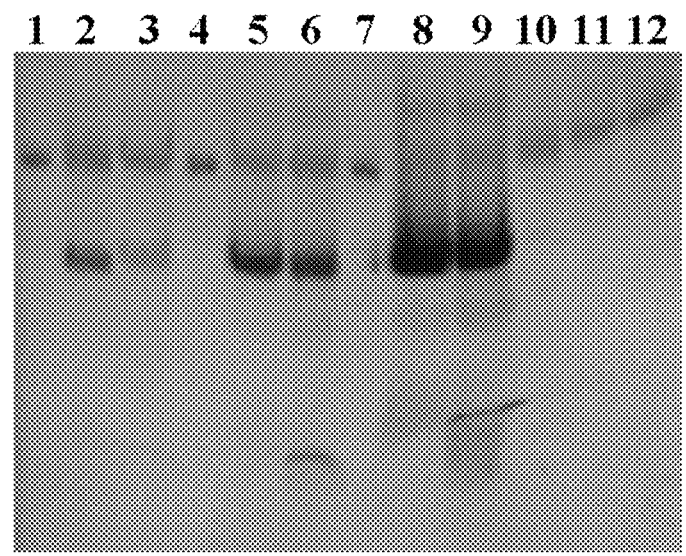
FIG. 27 shows a 10% polyacrylamide gel for transcription of 83-mer unmodified and click templates with coding strand (ODN-1). Lane 1: control coding strand (ODN-1); lane 2: transcription using unmodified template (ODN-2) 15 min; lane 3: transcription using click template (ODN-11) 15 min; lane 4: control coding strand (ODN-1); lane 5: transcription using unmodified template (ODN-2) 1 hr; lane 6: transcription using click template (ODN-11) 1 hr; lane 7: control coding strand (ODN-1); lane 8: transcription using unmodified template (ODN-2) 4 hr, lane 9; transcription using click template (ODN-11) 4 hr; lane 10: attempted transcription using click template (ODN-12) and long coding strand (ODN-1) in presence of $MgCl_2$ (10 mM) 4 hr; lane 11: attempted transcription using click template (ODN-12) and long coding strand (ODN-1) in presence of spermine tetrahydrochloride (0.5 mM) 4 hr; lane 12: attempted transcription using click template (ODN-12) and long coding strand (ODN-1) in presence of $MgCl_2$ (10 mM) and spermine tetrahydrochloride (0.5 mM) 4 hr.

A solution of $Cu^1$ click catalyst was prepared from tris-hydroxypropyltriazole ligand (1.4 µmol in 0.2 M NaCl, 94.0 µL), sodium ascorbate (2.0 µmol in 0.2 M NaCl, 4.0 µL) and $CuSO_4.5H_2O$ (0.2 µmol in 0.2 M NaCl, 2.0 µL). The two oligonucleotides (azide and alkyne), and the complementary splint (5.0 nmol of each) in 0.2 M NaCl (100.0 µL) were annealed by heating at 90° C. for 5 min then cooled slowly to room temperature. The above $Cu^1$ click catalyst was added to the annealed oligonucleotides and the mixture was kept at room temperature for 2 hr. Reagents were removed by NAP-10 gel-filtration and the ligated product was analysed and purified by denaturing 20% polyacrylamide gel electrophoresis. The results are shown in FIG. 21, which shows a 20% polyacrylamide gel. Lane 1; azide oligonucleotide ODN-38, lane 2; click reaction mixture.

Templated Click Cyclization of 100-mer Oligonucleotide (ODN-30)

Linear oligonucleotide (ODN-30) and splint (ODN-50) (0.5 nmol of each) in 0.2 M NaCl (240 µL) were annealed by heating at 90° C. for 5 min then cooled slowly to room temperature (2 hr). A solution of $Cu^1$ click catalyst was prepared from tris-hydroxypropyltriazole ligand (175.0 nmol in 0.2 M NaCl, 5.0 µL), sodium ascorbate (500.0 nmol in 0.2 M NaCl, 4.0 µL) and $CuSO_4.5H_2O$ (25.0 nmol in 0.2 M NaCl, 1.0 µL). The $Cu^1$ solution was added to the annealed oligonucleotides and the reaction mixture was kept at room temperature for 3 hr. Reagents were removed using NAP-10 gel-filtration column and the ligated DNA was analysed and purified by denaturing 8% polyacrylamide gel electrophoresis.

Non Templated Click Cyclization of 100-mer Oligonucleotide (ODN-30)

A solution of the $Cu^1$ click catalyst (0.25 µmol in 0.2 M NaCl, 25.0 µL), prepared as described above, was added to the 5'-azide-3'-propargyl oligonucleotide (5.0 nmol in 0.2 M NaCl, 975 µL). The reaction mixture was kept at RT for 3 hr after which reagents were removed by NAP-10 gel-filtration. The ligated cyclic DNA product was analysed and purified by denaturing 8% polyacrylamide gel electrophoresis.

Templated Enzymatic Cyclization of 100-mer Oligonucleotide (ODN-48)

Linear oligonucleotide (ODN-48) and splint (ODN-50) (0.5 nmol of each) in Tris-HCl ligase Buffer (240 µL, 1×) were annealed by heating at 90° C. for 5 min then cooled slowly to room temperature (2 hr). T4 DNA Ligase (10 µL, 3 u/µL) was added to the annealed oligonucleotide solution and the reaction mixture was left at room temperature for 3 hr. Reagents were removed by NAP-10 gel-filtration and the ligated DNA was analysed and purified by denaturing 8% polyacrylamide gel electrophoresis.

1× Tris-HCl ligase Buffer: 30 mM Tris-HCl (pH 7.8), 10 mM MgCl2, 10 mM DTT and 1 mM ATP. (10× Buffer was supplied with the enzyme).

Attempted Non Templated Enzymatic Cyclization of 100-mer Oligonucleotide (ODN-48)

T4 DNA Ligase (10 µL, 3 u/µL) was added to the linear oligonucleotide (ODN-48) (0.5 nmol) in Tris-HCl ligase Buffer (240 µL, 1×) and the reaction mixture was left at room temperature for 3 hr. Reagents were removed by NAP-10 gel-filtration and the reaction mixture was analysed by denaturing 8% polyacrylamide gel electrophoresis.

In addition to the above 2 µM oligonucleotide concentration used in the non-templated enzymatic cyclization, attempts to cyclize the oligonucleotide at 5 µM concentration also failed to give any cyclic product.

Rolling Circle Amplification (RCA) of the Cyclic 100-mer ODN-31 and ODN-49 Using GoTaq DNA Polymerase RCA products of cyclic 100-mer (ODN-31) or (ODN-49) (5 ng) were generated using GoTaq DNA polymerase and 4 µL of 5× buffer (green buffer)* in a total reaction volume of 20 µL, 0.5 µM of primers ODN-32 and ODN-33, 0.2 mM dNTP and 0.5 unit of GoTaq under the following conditions: 95° C. (initial denaturation) for 2 min then 25 cycles of 95° C. (denaturation) for 15 sec, 54° C. (annealing) for 20 sec and 72° C. (extension) for 30 sec. The reaction mixture was loaded onto a 2% agarose gel in 1×TBE buffer. The same conditions were used for the linear control oligonucleotides (ODN-30) and ODN-48.

*5× Promega green buffer was provided with the enzyme (containing Tris.HCl, KCl, 7.5 mM MgCl$_2$, pH 8.5) to give a final Mg$^{2+}$ concentration of 1.5 mM.

RCA Reaction of Cyclic ODN-31 and ODN-49 Using Phi29 DNA Polymerase

RCA products from cyclic triazole oligo ODN-31 and unmodified cyclic control oligo ODN-49 were generated using phi29 DNA polymerase, 4 µL of 10× buffer* in a total reaction volume of 40 µL with 10 ng of the DNA template, 0.05 µM of each primer (ODN-32a and ODN-33a), 0.25 mM dNTP, 0.8 µL BSA (10 mg/mL) and 0.8 µL of phi29 DNA polymerase (10 u/µL).

*1× phi29 DNA Polymerase Buffer: 50 mM Tris-HCl, 10 mM MgCl$_2$, 10 mM (NH4)$_2$SO$_4$, 4 mM DTT, pH 7.5 at 25° C. (10× Buffer was supplied with the enzyme).

Probing the Rolling Circle Amplification Product of Cyclic ODN-31

4 µL of the GoTaq RCA product of cyclic 100-mer ODN-31 was further amplified by asymmetric PCR and probed in a Genie I PCR/fluorescence instrument (Optigene Ltd, UK) using 8 µL of 5× buffer (green buffer)* in a total reaction volume of 40 µL with, 0.5 µM of primer (ODN-33), 0.05 µM of primer (ODN-32), HyBeacon probe (ODN-34, 0.15 µM), 0.2 mM dNTP's and 1.0 unit of GoTaq DNA polymerase. An initial denaturation (95° C.) for 2 min was followed by 25 cycles of 95° C. for 15 sec, 54° C. for 20 sec and 72° C. for 30 sec, then a fluorescence melting curve (35° C.-95° C. at 1° C./min). The asymmetric PCR product from linear ODN-30 was probed under the same conditions and gave the same melting temperature as the RCA product (61.1° C.).

*5× Promega green buffer was provided with the enzyme (containing Tris.HCl, KCl, 7.5 mM MgCl$_2$, pH 8.5) to give a final Mg$^{2+}$ concentration of 1.5 mM.

Linear Copying of Triazole (ODN-08) and Normal (ODN-46) 81-mer Templates Using DNA Polymerase I, Large (Klenow) Fragment 6 µL of 10× buffer in a total reaction volume of 60 µL with (template ODN-8+ primer ODN-45) or (template ODN-46+ primer ODN-47) (66 µmol of each), 0.2 mM dNTP and 0.6 µL of DNA Polymerase I, Large (Klenow) Fragment (5 u/µL). The reaction mixture was left at 37° C. then 18 µL aliquot was taken after each time point, mixed with 2 µL EDTA (100 µM) and 20 µL of formamide then kept on the freezer until reached the last time point. The reaction mixture was then loaded onto a 10% polyacrylamide gel.

1× NEBuffer 2: 50 mM NaCl, 10 mM Tris-HCl, 10 mM MgCl$_2$, 1 mM DTT (pH 7.9 at 25° C.). (10× Buffer was supplied with the enzyme).

TABLE S1

Oligonucleotides used in this study

| Code | Oligonucleotide sequences (5'-3') |
| --- | --- |
| ODN-01 | $^z$TACCACACAATCTCACACTCTGGAATTCACACTGACAATACTGCCGACACACATAACC |
| ODN-02 | $^z$CAGCACACAATCTCACACTCTGGAATTCACACTGACAATACTGCCGACACACATAACC |
| ODN-03 | GCATTCGAGCAACGTAAGATCG$^{Me}$C$^k$ |
| ODN-04 | gcattcgagcaacgtaagatcct$^k$ |
| ODN-05 | gcattcgagcaacgtaagatcgt$^k$ |
| ODN-06 81-mer | GCATTCGAGCAACGTAAGATCCT,TACCACACAATCTCACACTCTGGAATTCACACTGACAATACTGCCGACACACATAACC |
| ODN-07 81-mer | GCATTCGAGCAACGTAAGATCGT,CAGCACACAATCTCACACTCTGGAATTCACACTGACAATACTGCCGACACACATAACC |
| ODN-08 81-mer | GCATTCGAGCAACGTAAGATCG$^{Me}$C,CAGCACACAATCTCACACTCTGGAATTCACACTGACAATACTGCCGACACACATAACC |
| ODN-09 | GCATTCATGT$^{Me}$C$^k$ |
| ODN-10 | $^z$CTGGTCCGTG$^{Me}$C$^k$ |
| ODN-11 | $^z$CGCGTCTAACC |
| ODN-12 33-mer | GCATTCATGT$^{Me}$C,CTGGTCCGTG$^{Me}$C,CGCGTCTAACC |
| ODN-13 | 5TTTTGGTTAGACGCGGCACGGACCAGGACATGAATGCTTTT |
| ODN-14 | $^z$TCGGTCGTCGAATTCTAGTAGATGTCTACATGTACAACATACGCGCAGACGTATAGACTATCGCTCGTG$^{Me}$C$^k$ |
| ODN-14a Cyclic | Same sequence as linear ODN-14 with $^{Me}$C,T in the cyclic construct |
| ODN-15 | GCATTCGAGCAACGTAAGATCCTGAACTGGCATGACGGTATGACACTGGCATGCTGTGAGAGCATATGT$^{Me}$C$^k$ |
| ODN-16 | $^z$TGCGTCGTCTGAGCAGTCTGATCGTGTCTGAGTACGGCATTACCAGACAATACTGCCGACACACATAACC |

TABLE S1-continued

Oligonucleotides used in this study

| Code | Oligonucleotide sequences (5'-3') |
| --- | --- |
| ODN-17 splint | TACTAGAATTCGACGACCGAGACATATGCTCTCACAGCAT |
| ODN-18 splint | CAGACTGCTCAGACGACGCAGCACGAGCGATAGTCTATAC |
| ODN-19 210-mer | GCATTCGAGCAACGTAAGATCCTGAACTGGCATGACGGTATGACACT GGCATGCTGTGAGAGCATATGT$^{Me}$C$_t$TCGGTCGTCGAATTCTAGTAGAT GTCTACATGTACAACATACGCGCAGACGTATAGACTATCGCTCGTG$^{Me}$C$_t$TGCGTCGTCTGAGCAGTCTGATCGTGTCTGAGTACGGCATTACCAG ACAATACTGCCGACACACATAACC |
| ODN-20 | $^z$CTGGTCGTCGAATTCTAGTAGATGTCTACATGTACAGATGTCGATAC GCCAGTACGCGCTAGGATCACATACGCGCAGACGTATAGACTATCGC TCGTG$^{Me}$C$^k$ |
| ODN-21 | $^z$CGCGTCGTCTGAGCAGTCTGATCGTGTCTGAGTACGCATGATCTGGA TGTGTGATGTAGATCGTCAGCATTACCAGACAATACTGCCGACACAC ATAACC |
| ODN-22 | GCATTCGAGCAACGTAAGATCCTGAACTGGCATGACAGTGAGCTATG CCTCGCACTCTATCTACCTGGTATGACACTGGCATGCTGTGAGAGCAT ATGT$^{Me}$C$^k$ |
| ODN-23 splint | CTGCTCAGACGACGCGGCACGAGCGATAGTCT |
| ODN-24 splint | AGAATTCGACGACCAGGACATATGCTCTCACA |
| ODN-25 300-mer | GCATTCGAGCAACGTAAGATCCTGAACTGGCATGACAGTGAGCTATG CCTCGCACTCTATCTACCTGGTATGACACTGGCATGCTGTGAGAGCAT ATGT$^{Me}$C$_t$CTGGTCGTCGAATTCTAGTAGATGTCTACATGTACAGATGT CGATACGCCAGTACGCGCTAGGATCACATACGCGCAGACGTATAGAC TATCGCTCGTG$^{Me}$C$_t$CGCGTCGTCTGAGCAGTCTGATCGTGTCTGAGTA CGCATGATCTGGATGTGTGATGTAGATCGTCAGCATTACCAGACAAT ACTGCCGACACACATAACC |
| ODN-26 (P) | GCATTCGAGCAACGTAAG short primer 1 |
| ODN-27 (P) | GGTTATGTGTGTCGGCAG short primer 2 |
| ODN-28 (P) | CGCGCCATGGGCATTCGAGCAACGTAAG long primer 1 |
| ODN-29 (P) | CGCGCTCGAGGGTTATGTGTGTCGGCAG long primer 2 |
| ODN-30 | $^z$TCGGTCGTCGAATTCTAGTAGATGTCFACATGTACAGATGTCGATAC GCCAGTACGCGCTAGGATCACATACGCGCAGACGTATAGACTATCGC TCGTG$^{Me}$C$^k$ |
| ODN-31 | Cyclic oligonucleotide, same sequence as linear ODN-30 with $^{Me}$C$_t$T triazole linkage |
| ODN-32 (P) | GAGCGATAGTCTATACGT |
| ODN-33 (P) | TCGTCGAATTCTAGTAGA |
| ODN-32a (P) | GAGCGATAGTCTATACxGxT |
| ODN-33a (P) | TCGTCGAATTCTAGTAxGxA |
| ODN-34 (HyBe) | tmsGCGCGTACFGGCGFATCGP |
| ODN-35 | GTTGTTAGTACTCA$^{Me}$C$^k$ |
| ODN-36 | $^z$CAGTCACAGAAAAGC |
| ODN-37 | GTTGTTCGATCGTTGTCAGAAGTAAGTTGG$^{Me}$C$^k$ |
| ODN-38 | $^z$CGCAGTGTTATCACT |
| ODN-39 (P) | GTTGTT<u>AGTACT</u>CA$^{Me}$C$_t$CAGTCACAGAAAAGC<br>BLA ScaI forward tz |
| ODN-40 (P) | GTTGTT<u>AGTACT</u>CACCAGTCACAGAAAAGC<br>BLA ScaI forward |
| ODN-41 (P) | GTTGTT<u>CGATCG</u>TTGTCAGAAGTAAGTTGG$^{Me}$C$_t$CGCAGTGTTATCACT<br>BLA PvuI reverse tz |

TABLE S1-continued

Oligonucleotides used in this study

| Code | Oligonucleotide sequences (5'-3') |
|---|---|
| ODN-42 (P) | GTTGTTCGATCGTTGTCAGAAGTAAGTTGGCCGCAGTGTTATCACT<br>BLA PvuI reverse |
| ODN-43 splint | CTGTGACTGGTGAGTACT3 |
| ODN-44 splint | AACACTGCGGCCAACTTA3 |
| ODN-45 (P) | 5GGTTATGTGTGTCGGCAG |
| ODN-46 | GCATTCGAGCAACGTAAGATCGCCAGCACACAATCTCACACTCTGGA<br>ATTCACACTGACAATACCAATACACACAGCCGTC<br>Linear unmodified 81-mer |
| ODN-47 (P) | 5GACGGCTGTGTGTATTGG |
| ODN-48 linear | PhTCGGTCGTCGAATTCTAGTAGATGTCTACATGTACAGATGTCGATA<br>CGCCAGTACGCGCTAGGATCACATACGCGCAGACGTATAGACTATCG<br>CTCGTGC |
| ODN-49 cyclic | Same sequence as ODN-48 but cyclic with<br>phosphate linkage |
| ODN-50 splint | GAATTCGACGACCGAGCACGAGCGATAGTC |

$^z$ = 5'-azide, $^k$ = 3'-propargyl, ᴧ = triazole linkage, F = fluorescein dT, 3 = 3'-fluorescein C7, 5 = 5'-fluorescein C6, P = propanol, Ph = 5'-phosphate (Link Technologies), x = phosphothioate, Tms = trimethoxystilbene. HyBe = HyBeacon. Lower case sequences are oligonucleotides made from 5' to 3' using reverse phosphoramidite monomers

TABLE S2

Oligonucleotide mass spectra

| Code | Oligonucleotide sequence | Calc. | Found |
|---|---|---|---|
| ODN-04 | gcattcgagcaacgtaagatcct$^k$ | 7111 | 7112 |
| ODN-05 | gcattcgagcaacgtaagatcgt$^k$ | 7071 | 7071 |
| ODN-09 | GCATTCATGT$^{Me}$C$^k$ | 3360 | 3360 |
| ODN-10 | $^z$CTGGTCCGTG$^{Me}$C$^k$ | 3402 | 3404 |
| ODN-11 | $^z$CGCGTCTAACC | 3302 | 3303 |
| ODN-12 | GCATTCATGT$^{Me}$C$_t$CTGGTCCGTG$^{Me}$C$_t$CGCGTCTAACC | 10064 | 10064 |
| ODN-14 | $^z$TCGGTCGTCGAATTCTAGTAGATGTCTACATGTACA<br>ACATACGCGCAGACGTATAGACTATCGCTCGTG$^{Me}$C$^k$ | 21616 | 21616 |
| ODN-14a Cyclic | Same sequence as linear ODN-14 with $^{Me}$C$_t$T in the cyclic construct | 21616 | 21616 |
| ODN-15 | GCATTCGAGCAACGTAAGATCCTGAACTGGCATGAC<br>GGTATGACACTGGCATGCTGTGAGAGCATATGT$^{Me}$C$^k$ | 21730 | 21728 |
| ODN-16 | $^z$TGCGTCGTCTGAGCAGTCTGATCGTGTCTGAGTACG<br>GCATTACCAGACAATACTGCCGACACACATAACC | 21518 | 21516 |
| ODN-30 | $^z$TCGGTCGTCGAATTCTAGTAGATGTCFACATGTACA<br>GATGTCGATACGCCAGTACGCGCTAGGATCACATAC<br>GCGCAGACGTATAGACTATCGCTCGTG$^{Me}$C$^k$ | 31423 | 31422 |
| ODN-31 Cyclic | Same sequence as linear ODN-30 with $^{Me}$C$_t$T in the cyclic construct | 31423 | 31422 |
| ODN-48 linear | PhTCGGTCGTCGAATTCTAGTAGATGTCTACATGTAC<br>AGATGTCGATACGCCAGTACGCGCTAGGATCACATA<br>CGCGCAGACGTATAGACTATCGCTCGTGC | 30910 | 30910 |

TABLE S2-continued

Oligonucleotide mass spectra

| Code | Oligonucleotide sequence | Calc. | Found |
|---|---|---|---|
| ODN-49 cyclic | Same sequence as ODN-48 but cyclic with phosphate linkage | 30892 | 30892 |

$^z$ = 5'-azide, $^k$ = 3'-propargyl, $_t$ = triazole linkage, F = fluorescein dT, Ph = 5'-phosphate (Link Technologies). Lower case sequences are oligonucleotides made in 5' to 3' direction using reverse phosphoramidite monomers. Mass spectra were recorded on a Bruker microTOF™ II focus ESI-TOF MS instrument in ES− mode.

PCR and Sequencing of Triazole DNA Templates
PCR Using GoTaq DNA Polymerase

PCR products from 81-mer, 210-mer and 300-mer templates were generated using GoTaq DNA polymerase (available from Promega) with 4 µL of 5× buffer (green buffer) in a total reaction volume of 20 µL with 5 ng of the DNA template, 0.5 µM of each primer, 0.2 mM dNTP and 0.5 unit of GoTaq. The reaction mixture was loaded onto a 2% agarose gel in 1× TBE buffer. PCR cycling conditions: 95° C. (initial denaturation) for 2 min then 25 cycles of 95° C. (denaturation) for 15 sec, 54° C. (annealing) for 20 sec and 72° C. (extension) for 30 sec. 5× Promega green PCR buffer was provided with the enzyme (containing Tris.HCl, KCl, 7.5 mM $MgCl_2$, pH 8.5) to give a final $Mg^{2+}$ concentration of 1.5 mM.

PCR Using Pfu DNA Polymerase

PCR product from ODN-08 (81-mer CC template) was generated using 2 µL of 10× buffer in a total reaction volume of 20 µL with 5 ng of the DNA template, 0.5 µM of each primer, 0.2 mM dNTP and 1.0 unit of Pfu DNA polymerase. (10× reaction buffer=200 mM Tris-HCl (pH 8.8), 100 mM KCl, 100 mM $(NH_4)_2SO_4$, 20 mM $MgSO_4$, 1.0% Triton® X-100 and 1 mg/ml nuclease-free BSA). PCR cycling conditions: 95° C. (initial denaturation) for 2 min then 25 cycles of 95° C. for 15 sec, 54° C. for 20 sec and 72° C. for 30 sec. This was followed by one cycle of 72° C. for 2 min.

Sequencing of Clones from the PCR Product of 81-mer, 210-mer and 300-mer Triazole Templates.

The PCR products were prepared as above using GoTaq or Pfu DNA polymerase and purified on a 2% agarose gel followed by extraction using QIAquick Gel Extraction kit Cat. No. 28704. The purified PCR products were then cloned and sequenced by the automated fluorescent Sanger method: 10 clones for ODN-25 (300-mer with two $^{Me}C_tC$ linkages), 50 clones for ODN-19 (210-mer with two $^{Me}C_tT$ linkages), 40 clones for ODN-08 (81-mer with $^{Me}C_tC$ linkage), 17 clones for ODN-07 (81-mer with $T_tC$ linkage) and 17 clones for ODN-06 (81-mer with $T_tT$ linkage). ODN-08 (81-mer with $^{Me}C_tC$) was amplified using both GoTaq and Pfu DNA polymerases, and 20 clones of each were sequenced. The polymerases read the sequence around the triazole linkages correctly for all 134 sequences.

PCR of BLA Fragment with Click Primers

The region between the ScaI and PvuI sites of BLA was amplified by PCR with GoTaq DNA polymerase using the click-linked oligonucleotides ODN-39 and ODN-41, 10 µL of 5× buffer in a total reaction volume of 50 µL with 1 ng of the DNA template, 1 µM of each primer, 0.2 mM dNTP and 1 unit of GoTaq. The reaction was repeated with normal oligonucleotides (no triazole linker). The reaction mixtures were loaded onto a 2% agarose gel in 1×TAE buffer; both reactions gave products of identical size. PCR cycling conditions were: 94° C. (initial denaturation) for 1.5 min then 35 cycles of 94° C. (denaturation) for 30 sec, 46.5° C. (annealing) for 30 sec and 72° C. (extension) for 30 sec. The reaction was held at 72° C. for 5 minutes after the 35 cycles.

Restriction Digestion of PCR Product and Vector

The PCR products were digested with ScaI HF and PvuI restriction endonucleases (NEB, Cat. No. R3122 and R0150) according to the manufacturer's protocol and was purified using QIAquick PCR purification kit (QIAGEN, Cat. No. 28106). The Luciferase T7 control plasmid (Promega, Cat. No. L4821) was also digested with ScaI HF and PvuI, and treated with thermosensitive alkaline phosphatase (Promega, Cat. No. M9910) to remove the 5'-phosphate groups from the linearized plasmid DNA, thus preventing recircularisation during ligation. The linear plasmid was gel-purified using QIAquick gel extraction kit (QIAGEN Cat. No. 28706) to remove the undigested plasmid and the excised fragment.

Ligation Reactions and Transformation into E. coli

The digested PCR products (triazole and normal) and linearized plasmid were ligated for 16 hr at 15° C. (total volume 10 µL, 1:3 vector:insert ratio) using T4 DNA ligase (Promega, Cat. No. M1801). Negative control ligations were set up as above, using water instead of insert. 5 µL of each ligation mixture was transformed into chemically competent E. coli (NEB 5α, NEB, Cat. No. C2992H) using the standard protocol. Transformants were recovered in 895 µL of SOC at 37° C. with shaking for one hour. 100 µL of each recovery solution was spread onto LB agar plates and incubated at 37° C. overnight. Colonies were counted using a Gel Doc XR+ system and Quantity One Software (both from Bio-Rad Laboratories). The above procedure was repeated for the UvrB deficient E. coli strain (JW0762-2, CGSC, Cat. No. 8819) which was supplied by the Coli Genetic Stock Center (CGSC) at Yale University.

Sequencing of the BLA Gene

50 Colonies were picked from plates containing the plasmids with the triazole DNA insert in its BLA gene and 50 were picked from the positive control plates (normal BLA gene). The colonies were grown overnight in LB and the plasmids from each culture were isolated using QIAprep Spin miniprep kit (QIAGEN, Cat. No. 27106). They were then sequenced by the automated fluorescent Sanger method. Mutations were not observed in the region between the ScaI and PvuI sites in any of the plasmids. For the experiment on DNA repair, 21 colonies were sequenced from repair-deficient E. coli strain JW0762-2 and all sequences were found to be correct.

Efficient RNA Synthesis by In Vitro Transcription of a Triazole-Modified DNA Template A DNA strand containing a triazole phosphodiester mimic is an efficient template for in vitro transcription. Transcription through a heavily modified DNA backbone linkage was demonstrated and it was shown that click-ligated DNA could be useful for the direct synthesis of biologically active RNA and proteins.

General Method for Oligonucleotide Synthesis and Purification

Standard DNA phosphoramidites, solid supports and additional reagents were purchased from Link Technologies and Applied Biosystems. Oligonucleotides were synthesized on an Applied Biosystems 394 automated DNA/RNA synthesizer using a standard 0.2 or 1.0 μmole phosphoramidite cycle of acid-catalyzed detritylation, coupling, capping, and iodine oxidation. Stepwise coupling efficiencies and overall yields were determined by the automated trityl cation conductivity monitoring facility and in all cases were >98.0%. All β-cyanoethyl phosphoramidite monomers were dissolved in anhydrous acetonitrile to a concentration of 0.1 M immediately prior to use. The coupling time for normal A, G, C, and T monomers was 35 s, whereas the coupling time for the 5'-iodo dT phosphoramidite monomer was extended to 6 min. Cleavage of oligonucleotides from the solid support and deprotection was achieved by exposure to concentrated aqueous ammonia solution for 60 min at room temperature followed by heating in a sealed tube for 5 hr at 55° C. The oligonucleotides were purified by reversed-phase HPLC on a Gilson system using an XBridge™ BEH300 Prep C18 10 μM 10×250 mm column (Waters) with a gradient of acetonitrile in ammonium acetate (0% to 50% buffer B over 30 min, flow rate 4 mL/min), buffer A: 0.1 M ammonium acetate, pH 7.0, buffer B: 0.1 M ammonium acetate, pH 7.0, with 50% acetonitrile. Elution was monitored by UV absorption at 305 or 295 nm. After HPLC purification, oligonucleotides were desalted using NAP-10 columns and analyzed by gel electrophoresis.

Synthesis of the 3'-alkyne oligonucleotides

3'-Alkyne oligonucleotides were synthesized on the 1.0 μmole scale by the attachment of 5'-O-(4,4'-dimethoxytrityl)-3'-O-propargyl-5-methyldeoxycytidine to a solid support (33 μmole/g loading, AM polystyrene, Applied Biosystems) according to the published method in A. H. El-Sagheer et al. 2011, Proc. Natl. Acad. Sci. U.S.A., 108, 11338-11343. The resin was packed into a twist column (Glen Research) then used to assemble the required sequence in the 3'- to 5'-direction by standard phosphoramidite oligonucleotide synthesis. The oligonucleotides were then cleaved and deprotected by exposure to concentrated aqueous ammonia for 60 min at room temperature followed by heating in a sealed tube for 5 h at 55° C. before purification as outlined above in the general method.

ii) Synthesis of the 5'-azide oligonucleotides

Oligonucleotides were assembled on the 1.0 μmole scale (trityl-off) as described above in the general method with 5'-iodo-dT using the commercially available 5'-iodo dT phosphoramidite monomer (Glen Research). To convert the 5'-iodo dT to 5'-azido dT, sodium azide (50 mg) was suspended in dry DMF (1 mL), heated for 10 min at 70° C. then cooled down and the supernatant taken up into a 1 mL syringe, passed back and forth through the column and left for 5 h at 55° C. The column was then washed with DMF and acetonitrile and dried by the passage of a stream of argon gas. The resultant 5'-azide oligonucleotides were cleaved from the solid support and deprotected by exposure to concentrated aqueous ammonia solution for 60 min at room temperature followed by heating in a sealed tube for 6 h at 55° C. and purified by HPLC as described above in the general method: Synthesis of the triazole Templates (ODN-11) and (ODN-12) (83-mer) for Transcription A solution of $Cu^1$ click catalyst was prepared from tris-hydroxypropyltriazole ligand (2.8 μmole in 0.2 M NaCl, 88.0 μL), sodium ascorbate (4.0 μmole in 0.2 M NaCl, 8.0 μL) and $CuSO_4.5H_2O$ (0.4 μmole in 0.2 M NaCl, 4.0 μL). The two oligonucleotides (azide and alkyne), and the complementary splint (20.0 nmole of each) in 0.2 M NaCl (150.0 μL) were annealed by heating at 90° C. for 5 min then cooled down slowly to room temperature. The above $Cu^1$ click catalyst was added to the annealed oligonucleotides and the mixture was kept at room temperature for 2 hr. Reagents were removed by NAP-10 gel-filtration and the ligated product was analysed and purified by denaturing 12% polyacrylamide gel electrophoresis.

Transcription of the Triazole (Triazole Linkage in the Coding Region) and Unmodified Templates with Long and Short Coding Strands The DNA template (triazole ODN-11) or (unmodified ODN-2) and the coding strand (long ODN-1) or (short ODN-3) (39.0 pmole of each in 8.0 μL water) was added to a solution of the buffer* (5×, 4.0 μL) and rNTP (25.0 mM of each rNTP, 6.0 4). The mixtures were vortexed and the RiboMAX large scale RNA production system-T7 (2.0 μL) was added. The reactions were then heated at 37° C. for the desired time (3 reactions were conducted at 4 hr, 1 hr and 15 min, and timed to finish simultaneously then mixed with formamide and loaded immediately onto 10% polyacrylamide gel.

*5× buffer (was provided with the enzyme): 400 mM HEPES-KOH (pH 7.5), 120 mM $MgCl_2$, 10 mM spermidine and 200 mM DTT.

Attempted Transcription of the Triazole Template (Triazole Linkage on the Promoter Region) with Long and Short Coding Strands Attempts to transcribe the triazole template (ODN-12) with the triazole in the promoter region, using both long (ODN-1) and short (ODN-3) coding strands under the previous conditions failed to give any product. The reactions were also attempted in presence of additional $MgCl_2$ (10 mM or 1 mM), spermine tetrachloride (0.5 mM) or a mixture of both, and also failed to give any product.

Transcription of the Triazole and Unmodified Templates with the Long Coding Strand for mass spectrometry A solution of the DNA template (triazole ODN-11) or (unmodified ODN-2) and the long coding strand (ODN-1) (0.195 nmole, (3.8 μg) of each in 40.0 μL water) was added to a solution of the buffer* (5×, 20.0 μL) and rNTP (25.0 mM of each rNTP, 30.0 μL). The mixtures were vortexed and the RiboMAX large scale RNA production system-T7 (10.0 4) was added. The reactions were then heated at 37° C. for 4 hrs followed by heating at 65° C. for 10 min to denature the enzyme. 2×NAP-25 gel-filtration columns were used, for each reaction product, to desalt and remove the excess rNTP. After gel-filtration, the absorbance was measured at 260 to quantify the transcription product. 373.0 μg (19.0 nmole) of RNA transcript was formed from the native template (ODN-2) whereas 288.0 μg (14.7 nmole) was formed from the triazole template (ODN-11).

*5× buffer (was provided with the enzyme): 400 mM HEPES-KOH (pH 7.5), 120 mM $MgCl_2$, 10 mM spermidine and 200 mM DTT.

Quantification of the RNA transcribed from the triazole template (ODN-11) using the gel-image analysis (Gene-Tools, SynGene) was done for 12 different reactions on separate gels and gave 75%±5% for 3 hr incubation and 81%±5% for 4 hr incubation relative to the amount of RNA obtained from the unmodified template (ODN-2).

A total of 8 reactions were carried out using the long coding strand ODN-1 and 4 reactions were performed using the short coding strand ODN-3.

TABLE S3

Oligonucleotides used in this study

| Code | Oligonucleotide sequences (5'-3') |
|---|---|
| ODN-01 | GCAACC<u>TAATACGACTCACTATAg</u>GGAGAATTTCTGGTGACG<br>TTTGGCGGTATCAGTTTTACTCCGTGACTGCTCTGCCGCCC<br>native coding strand Transcription<br>start (+1) lower case, promoter region<br>underlined |
| ODN-02 | *GGGCGGCAGAGCAGTCACGGAGTA*AAACTGATACCGCCAAA<br>CGTCACCAGAAATTCTCCC*TATAGTGAGTCGTATTAGG*TTGC<br>native template in which underlined<br>region is transcribed, promoter in<br>italics |
| ODN-03 | GCAACC<u>TAATACGACTCACTATAg</u>GGAGAATTTCT<br>native short coding strand Transcription<br>start (+1) in lower case, promoter<br>region underlined |
| ODN-04 | pppGGGAGAAUUUCUGGUGACGUUUGGCGGUAUCAGUUUUA<br>CUCCGUGACUGCUCGCCGCCCc expected<br>transcribed RNA |
| ODN-05 | GGGCGGCAGAGCAGTCACGGAGTAAAA$^{Me}$C$^k$ |
| ODN-06 | GGGCGGCAGAGCAGTCACGGAGTAAAACTGATACCGCCAAA<br>CGTCACCAGAAATT$^{Me}$C$^k$ |
| ODN-07 | $^z$TGATACCGCCAAACGTCACCAGAAATTCTCCCTATAGTGAGT<br>CGTATTAGGTTGC |
| ODN-08 | $^z$TCCCTATAGTGAGTCGTATTAGGTTGC |
| ODN-09 | GGTGACGTTTGCGGTATCAGTTTTACTCCGTGACTGCT<br>splint |
| ODN-10 | ATACGACTCACTATAGGGAGAATTTCTGGTGACGTTTGG<br>splint |
| ODN-11 | <u>GGGCGGCAGAGCAGTCACGGAGTAAAA$^{Me}$C$_f$TGATACCGCCAA<br>ACGTCACCAGAAATTCTCCC</u>*TATAGTGAGTCGTATTAGGTTGC*<br>template with triazole downstream in<br>which underlined region is<br>transcribed, promoter in italics |
| ODN-12 | <u>GGGCGGCAGAGCAGTCACGGAGTAAAACTGATACCGCCAAA<br>CGTCACCAGAAATT$^{Me}$C$_f$TCCC</u>*TATAGTGAGTCGTATTAGGTTG*<br>C template with triazole in promoter,<br>in which underlined region should be<br>transcribed, promoter in italics |

$^z$= 5'-azide, $^k$= 3'-propargyl, $_f$= -triazole linkage, p = phosphate.

TABLE S4

Mass spectrometry of oligonucleotides used in this study

| Code | Calc. Mass | Found. Mass |
|---|---|---|
| ODN-01 | 25509 | 25508 |
| ODN-02 | 25652 | 25650 |
| ODN-03 | 10723 | 10723 |
| ODN-04 | 19726 | 19724 (N), 19726 (T) |
| ODN-05 | 8774 | 8771 |
| ODN-06 | 17347 | 17344 |
| ODN-07 | 16894 | 16891 |
| ODN-08 | 8321 | 8319 |
| ODN-09 | 12026 | 12025 |
| ODN-10 | 12076 | 12074 |
| ODN-11 | 25668 | 25666 |
| ODN-12 | 25668 | 25665 |

N = mass of the transcribed RNA formed from the unmodified template (ODN-2).
T = mass of transcribed RNA formed from the triazole template (ODN-11), Mass spectra were recorded on a Bruker micrOTOF ™ II focus ESI-TOF MS instrument in ES$^-$ mode.

The triazole linker formed by this method (FIG. 28) is correctly read-through by DNA polymerases and is functional in bacteria. In order to investigate the molecular basis of this discovery the high-resolution NMR structure of a DNA duplex containing this modification was determined and compared to a fully natural phosphodiester backbone. Although some structural and dynamic perturbations were observed around the triazole (FIG. 28b) the duplex adopted the normal B-conformation.

The triazole N2 and N3 nitrogen atoms are located close to the position of the phosphodiester oxygens of normal DNA and it is proposed that they can substitute as hydrogen-bond acceptors in interactions with polymerases. It has been shown that the triazole linkage is a plausible phosphodiester surrogate, but for an artificial DNA backbone linkage to be truly biocompatible it must also be functional in other fundamental biological processes, particularly DNA-templated RNA synthesis. This may enable long, fully synthetic, click-ligated DNA constructs to be used directly for the synthesis of biologically active RNA and proteins, and constitutes a significant advance.

Figure 28:
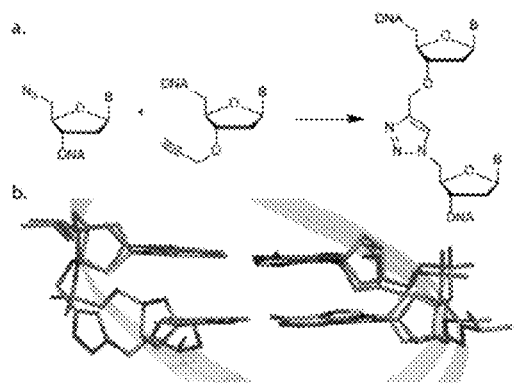
FIG. 28 shows an illustration of Click DNA ligation and chemical structure of the resultant triazole linkage. The reaction is catalysed by $Cu^1$ and a tris-triazole ligand. 1b The triazole linkage in B-DNA is compared to canonical DNA.

The triazole linkage in FIG. 28 allows the DNA duplex to adopt a normal B-conformation in which the Watson-Crick bases are paired and stacked within the helix. However, there is some distortion in the backbone at the site of the triazole. This causes displacement of the deoxyribose sugar to accommodate the longer linkage so that base stacking is preserved. It also leads to a small increase in the distance between the bases on either side of the triazole. These perturbations, along with the presence of the rigid triazole ring and lack of negative charge at the backbone, do not disrupt interactions with the RNA polymerase sufficiently to prevent transcription. Replication is not inhibited by the triazole linkage and neither is transcription. Unlike replication, transcription does not require an oligonucleotide primer; it is initiated by a 5'-nucleotide triphosphate and is a fundamentally different process.

The RiboMAX large scale RNA production system (Promega) containing the commonly used T7 RNA polymerase (T7-RNAP) which transcribes DNA downstream of a specific promoter sequence was used. T7-RNAP is an important enzyme for DNA-templated RNA synthesis; it is commonly used in biotechnology for the synthesis of small RNAs and to direct the expression of cloned genes. It does not require auxiliary proteins, and is structurally distinct from multi-subunit RNA polymerases of the bacterial and eukaryotic sub-families, but shares many common functional features with these more complex enzymes. The RNA transcript selected for this study contains the 54-mer DicF sequence which inhibits growth of *E. coli*. It was chosen because it is sufficiently short to be analysed at high resolution by polyacrylamide gel-electrophoresis and mass spectrometry. Two triazole-containing DNA template strands were synthesized, one with the triazole linkage inside the coding sequence and a second with the modification within the essential T7 RNA promoter region at the +4/5 position (Table S3). These oligonucleotides were designed to evaluate the efficiency of transcription through the modified template and to independently investigate whether T7-RNAP can interact with a triazole-modified promoter to initiate.

Figure 29:
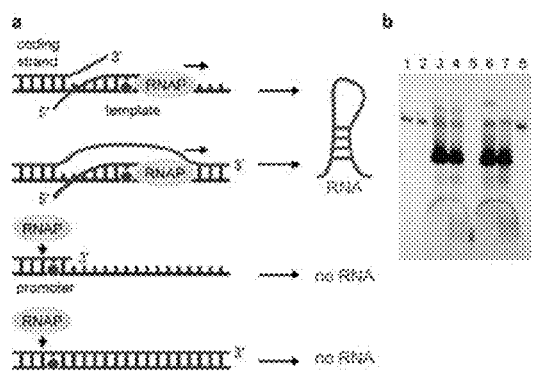
FIG. 29 shows a schematic of transcription using T7-RNAP with short and long DNA constructs with triazole linkages (pentagons). Transcription of 83-mer unmodified and triazole DNA templates. Lane 1: control unmodified 83-mer template (ODN-2); lane 2: control long coding strand (83-mer ODN-1); lane 3: reaction using unmodified template (ODN-2) and long coding strand (ODN-1); lane 4: reaction using 83-mer triazole template (ODN-11) and long coding strand (ODN-1); lane 5: control 35-mer short coding strand (ODN-3); lane 6: reaction using unmodified template (ODN-2) and short coding strand (ODN-3); lane 7: reaction using click template (ODN-11) and short coding strand (ODN-3); lane 8: control click template (ODN-11). 10% polyacrylamide gel.

Downstream transcription. Each of these oligonucleotides was hybridized to a full-length complementary strand and a shorter sequence. All four resultant constructs (FIG. 29a) contained the double stranded T7 promoter region. DNA templates with short and long coding strands are known to support efficient transcription of canonical DNA so it was thought prudent to evaluate the triazole-modified versions of both. Transcription reactions were carried out using T7-RNAP under standard conditions for varying periods of time and the results were compared to those obtained from the equivalent normal DNA templates (FIG. 29b).

Figure 30:
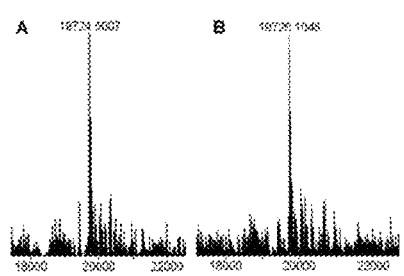
FIG. 30 shows ES– Mass spectra of the RNA transcripts from (A): the normal template (ODN-2) and (B): the triazole template (ODN-11); both with the long coding strand (ODN-1). The transcripts have the expected 5'-triphosphate and an additional 3'-cytidine. Required mass=19726.

When the triazole linkage was placed in the coding region of the template and combined with the long coding strand (ODN-1), the transcription reaction produced 77% of the quantity of RNA obtained from the native control under identical conditions (4 hr incubation). The triazole DNA produced 288 μg (14.7 nmole) of RNA from 3.8 μg (0.195 nmole) of the template, whereas the equivalent reaction with native DNA gave 373 μg (19 nmole) as determined by UV absorbance at 260 nm. Quantification by gel-image analysis gave 75%±5% for 3 hr incubation and 81%±5% after 4 hr (four replicates of each). The transcripts were characterised by ES– mass spectrometry (FIG. 30), and as expected contained a triphosphate group at the 5'-end and an additional cytidine at the 3'-terminus. When the reactions were repeated with the triazole in the promoter region at the +4/5 position there was no RNA product, even when transcription was stimulated by additional $MgCl_2$ or spermine. (ESI). Although it is known that the +4/5 position in the promoter is not highly sensitive to base sequence, the triazole linkage may be sufficiently disruptive at the local level to inhibit DNA-protein binding.

In summary, click chemistry is an efficient method for producing large DNA strands containing triazole linkages which are functional in bacteria: T7-RNAP can transcribe through such modified DNA strands to synthesize RNA in good yield, and is a further demonstration of the surprising biocompatibility of triazole DNA. This is the first example of transcription through a purely synthetic analogue of a DNA backbone. It has now surprisingly been shown that long DNA constructs made by solid-phase synthesis/click ligation (i.e. without the use of enzymes) can in principle be used directly to synthesize biologically active RNA constructs and proteins, even in vivo.

All publications and patents mentioned in the above specification are herein incorporated by reference. Various modifications and variations of the described methods, systems and products of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, chemistry or related fields are intended to be within the scope of the following claims.

---

What is claimed is:

1. A method for ligating one or more oligonucleotides, said method comprising reacting at least one alkyne group with at least one azide group to form at least one triazole phosphodiester mimic, wherein said reaction is selected from the following reaction schemes or an RNA or nucleic acid analogue equivalent thereof:

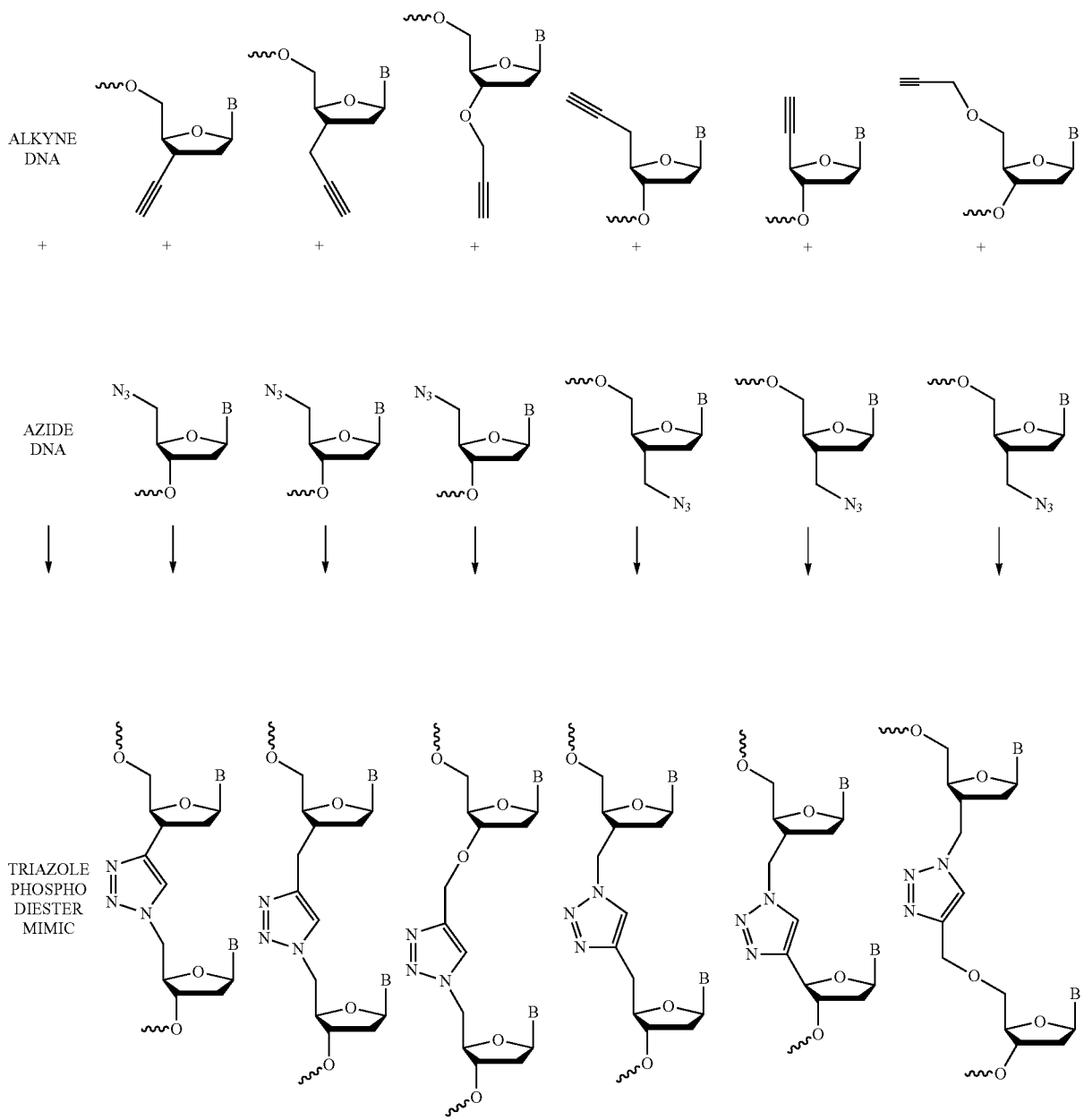

-continued
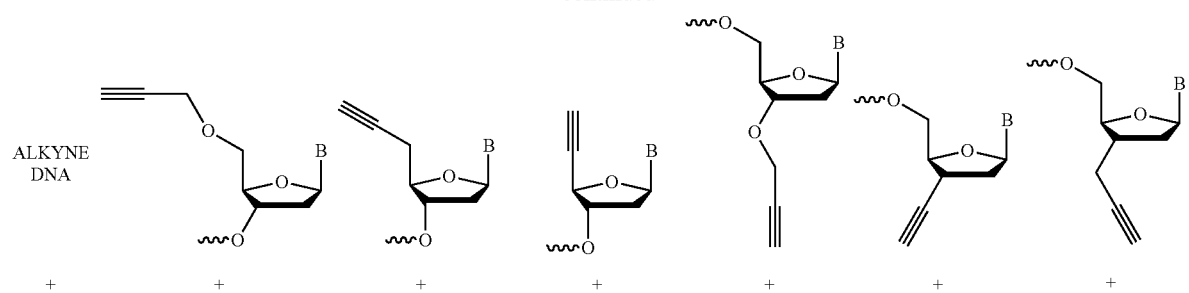
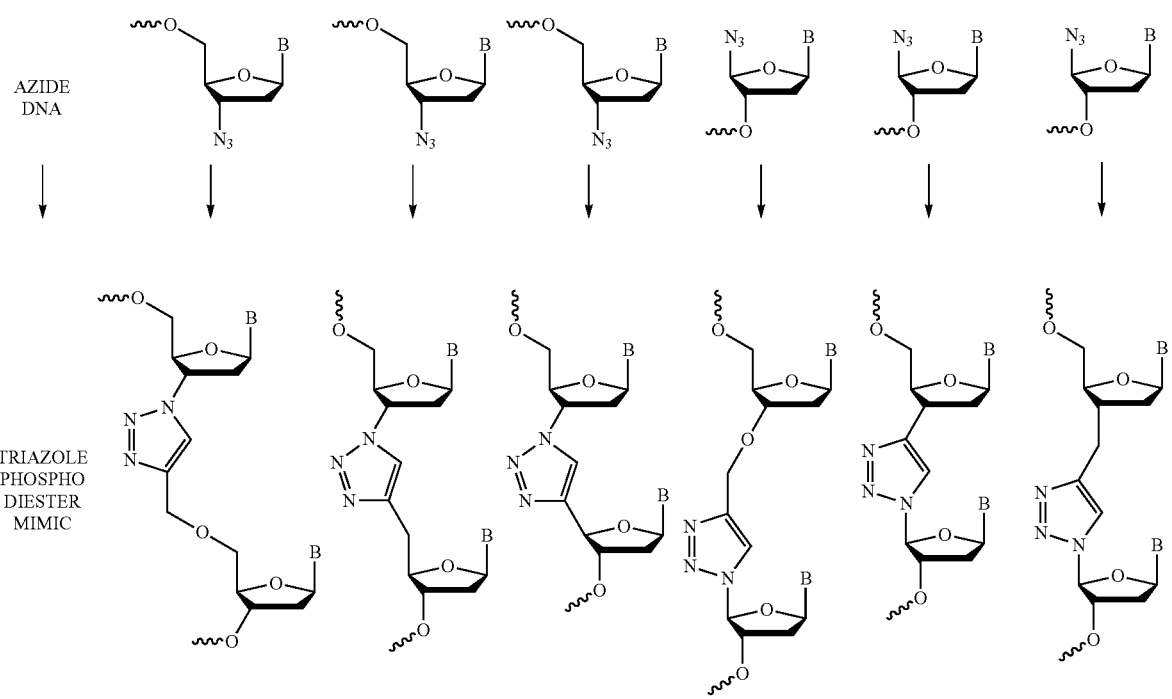
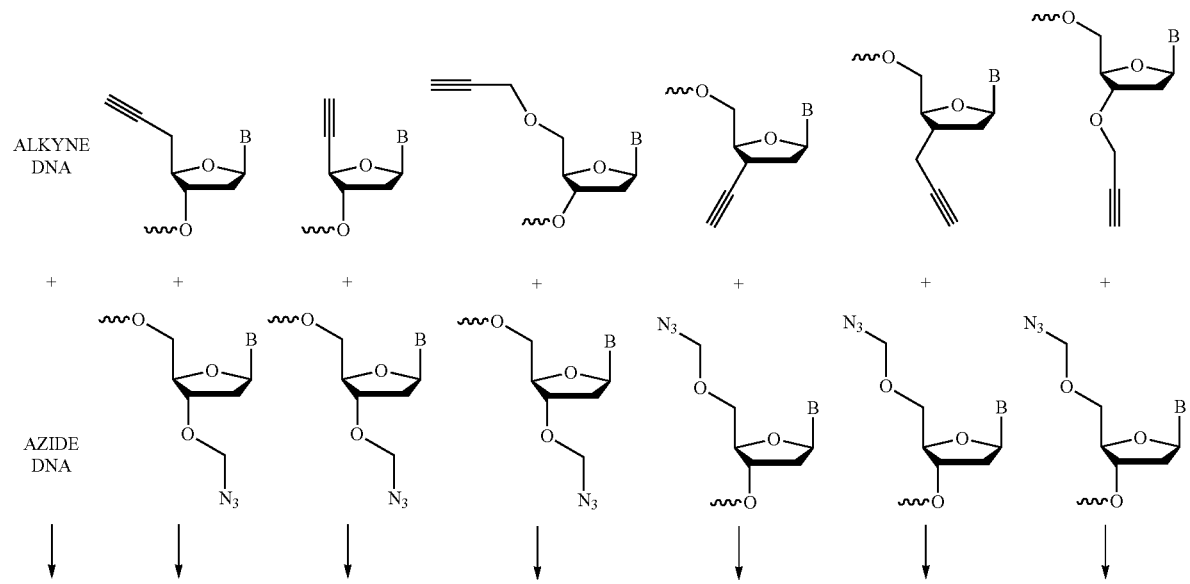

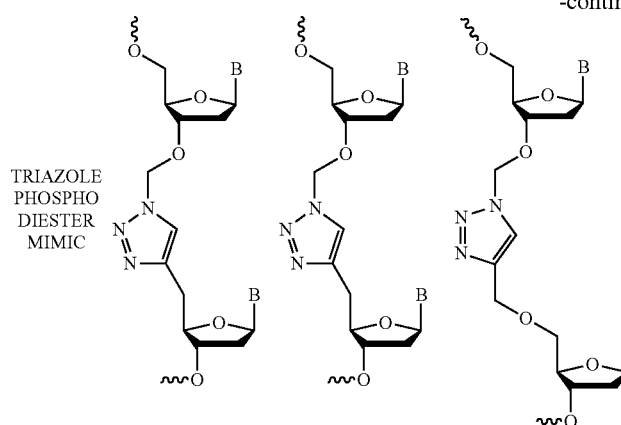
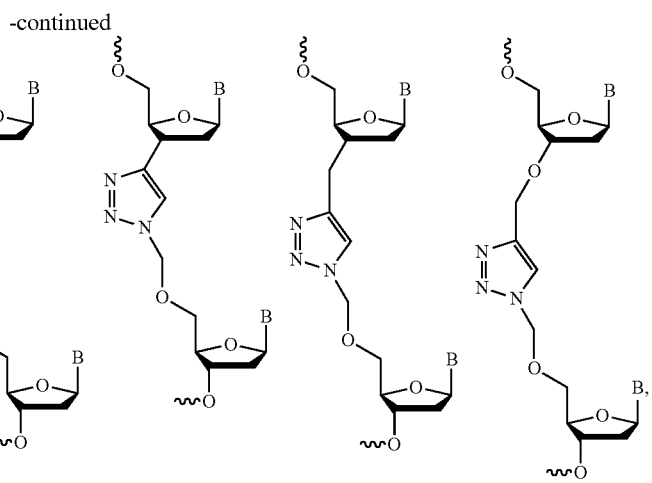

TRIAZOLE PHOSPHO DIESTER MIMIC

B = T, C, G or A and
  wherein each of the one or more oligonucleotides being ligated includes at least one conventional phosphodiester linkage.

2. A method according to claim 1 wherein two or more oligonucleotides are ligated together to form one or more triazole phosphodiester mimics.

3. A method according to claim 1 wherein said at least one triazole phosphodiester mimic can be read through accurately by a DNA polymerase and/or an RNA polymerase.

4. A method according to claim 1 wherein said reaction follows the reaction scheme below or an RNA or nucleic acid analogue equivalent thereof:

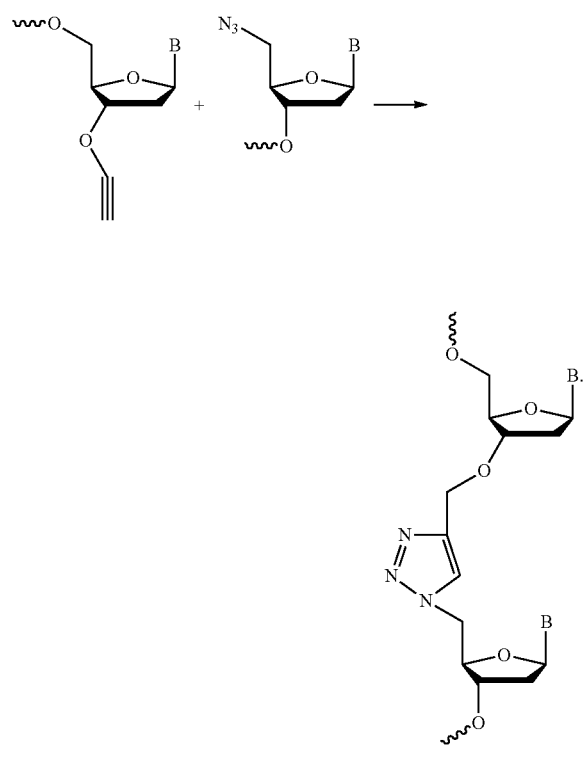

5. A method according to claim 1 wherein an alkyne group at the 5' or 3' end of one oligonucleotide is reacted with an azide group is at the 5' or 3' end of a second oligonucleotide to form at least one triazole phosphodiester mimic.

6. A method according to claim 1 wherein an alkyne group at the 3' end of one oligonucleotide is reacted with an azide group is at the 5' end of a second oligonucleotide to form at least one triazole phosphodiester mimic.

7. A method according to claim 1 wherein a double stranded oligonucleotide is ligated to a second double stranded oligonucleotide to form a double stranded oligonucleotide with at least one triazole phosphodiester mimic in each ligated strand.

8. A method according to claim 1 wherein a single or double stranded oligonucleotide is circularized by reacting at least one alkyne group at one end of the oligonucleotide with at least one azide group at the other end of the oligonucleotide to form at least one triazole phosphodiester mimic in each cyclized strand.

9. A method according to claim 1 wherein the reaction of at least one alkyne group with at least one azide group is carried out on a solid phase.

10. A method according to claim 1 wherein the reaction of at least one alkyne group with at least one azide group is carried out under templated conditions.

11. A method according to claim 1 wherein the reaction of at least one alkyne group with at least one azide group is carried out under templated conditions using a template, and wherein the template is obtained or obtainable by:
  reacting at least one alkyne group with at least one azide group to form at least one triazole phosphodiester mimic, wherein said reaction is selected from the following reaction schemes or an RNA or nucleic acid analogue equivalent thereof:

67
68
ALKYNE DNA
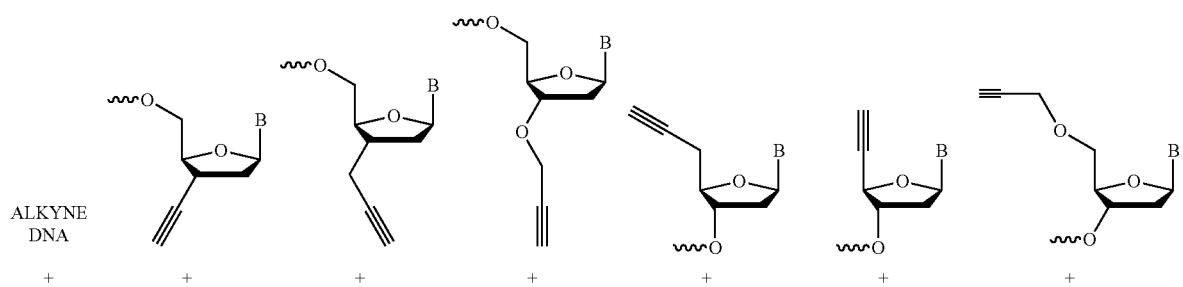
AZIDE DNA
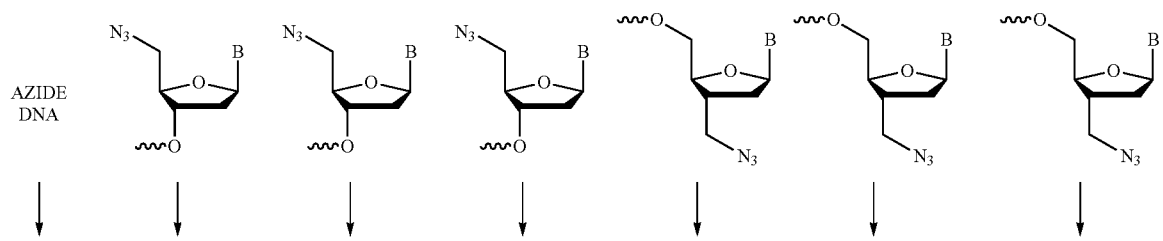
TRIAZOLE PHOSPHO DIESTER MIMIC
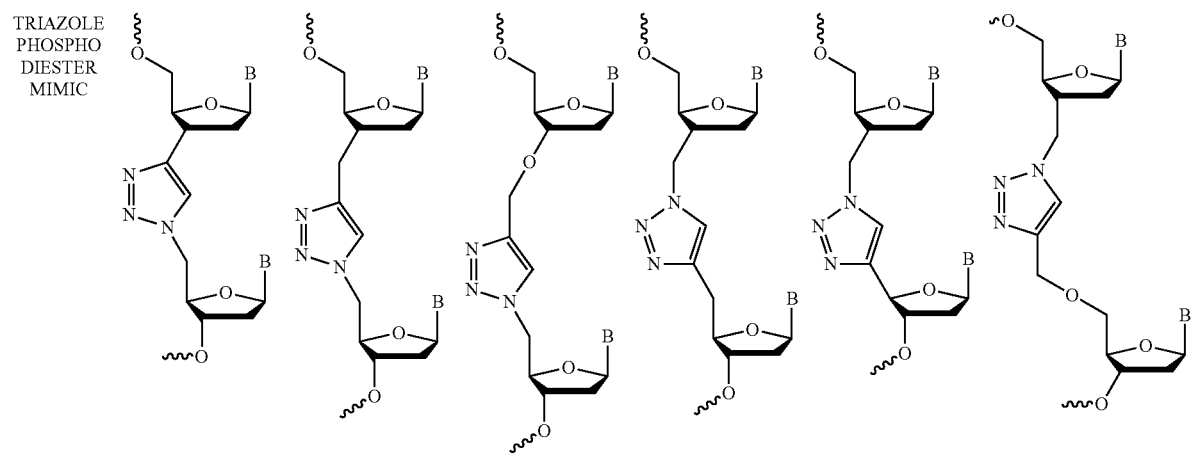
ALKYNE DNA
AZIDE DNA
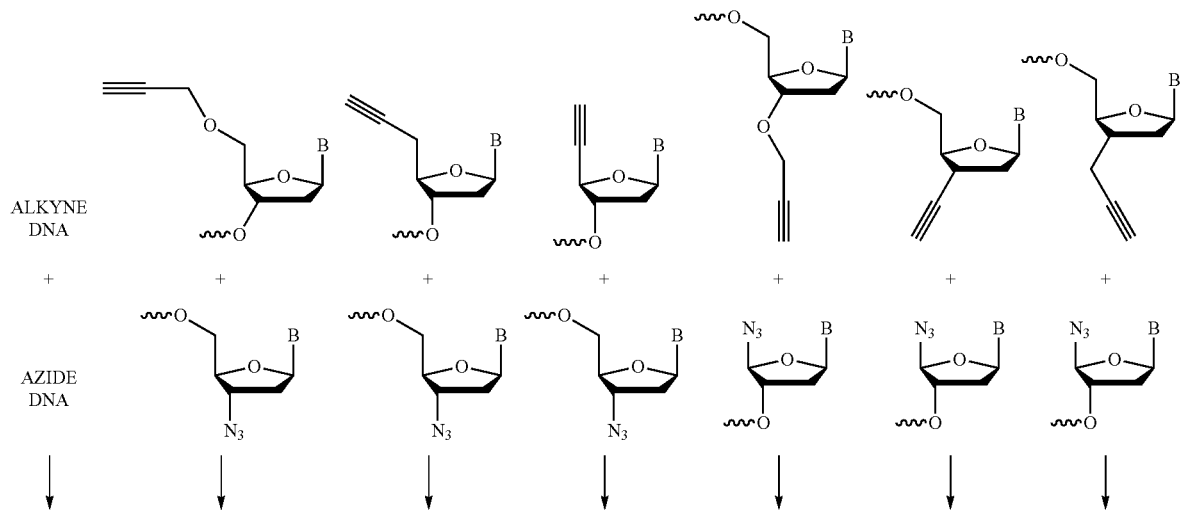

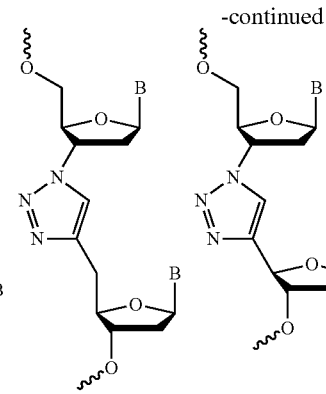
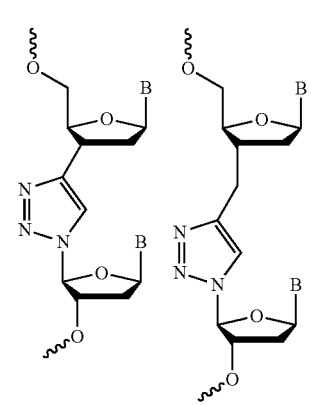

-continued

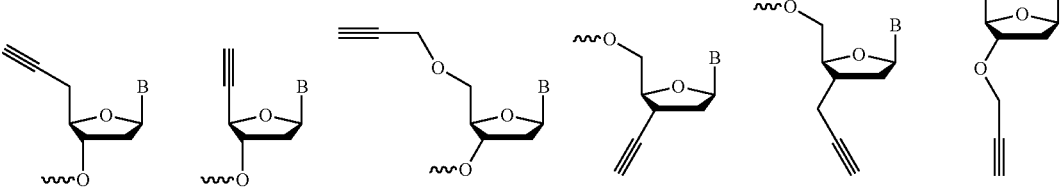

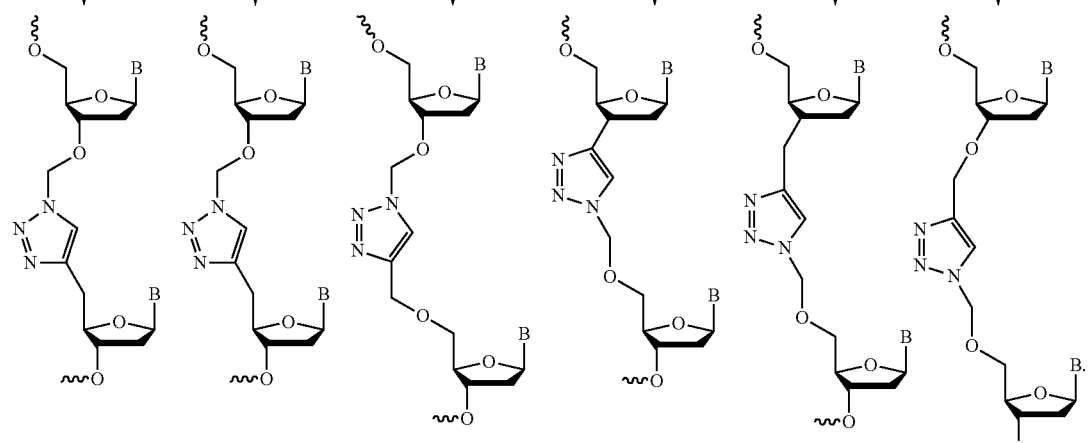

B = T, C, G or A

12. A method according to claim 1 wherein the reaction of at least one alkyne group with at least one azide group is carried out under templated conditions and the template is a cyclic single-stranded oligonucleotide and wherein a double-stranded helical oligonucleotide catenane is prepared.

13. A method according to claim 1 wherein the reaction of at least one alkyne group with at least one azide group is carried out under templated conditions using a single stranded circularized oligonucleotide as a template for the cyclization of a second linear complementary oligonucleotide by reacting an alkyne group at one end of the linear oligonucleotide with an azide group at the other end of the linear oligonucleotide and wherein a double stranded DNA catenane which contains at least one triazole backbone linkage that can be read through correctly by DNA and/or RNA polymerases is produced.

14. A method according to claim 1 wherein the reaction of at least one alkyne group with at least one azide group is carried out under untemplated conditions to circularize a single oligonucleotide strand or to join two or more single oligonucleotide strands.

15. A method according to claim 1 wherein the step of reacting at least one alkyne group with at least one azide group to form at least one triazole phosphodiester mimic is carried out more than once to form an oligonucleotide comprising more than one triazole phosphodiester mimic.

16. A method according to claim 1 for ligating more than one oligonucleotide wherein at least one oligonucleotide is DNA and at least one oligonucleotide is RNA or nucleic acid analogue.

17. A method according to claim 1 wherein at least one oligonucleotide comprises at least one DNA analogue and/or at least one RNA analogue and/or at least one modified nucleotide and/or at least one labeled oligonucleotide.

18. A method according to claim 1 wherein the reaction is catalyzed by Cu (I).

19. An oligonucleotide construct obtainable or obtained by a method according to claim 1.

20. An oligonucleotide construct comprising at least one triazole phosphodiester mimic having a structure selected from the following or an RNA equivalent thereof:

TRIAZOLE PHOSPHO DIESTER MIMICS

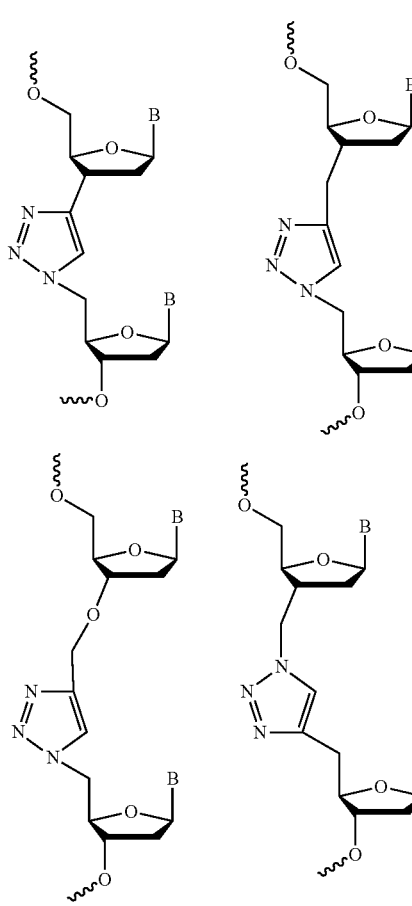

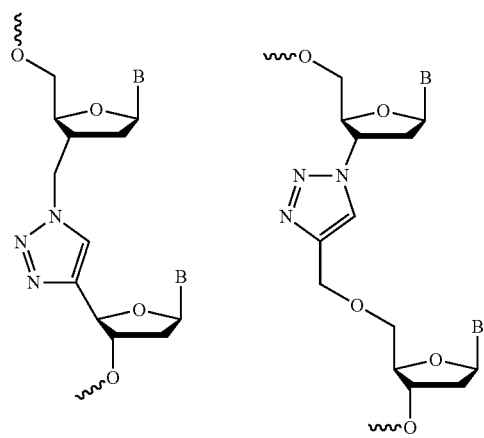

-continued

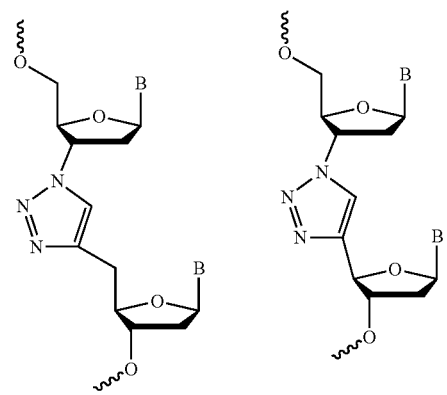

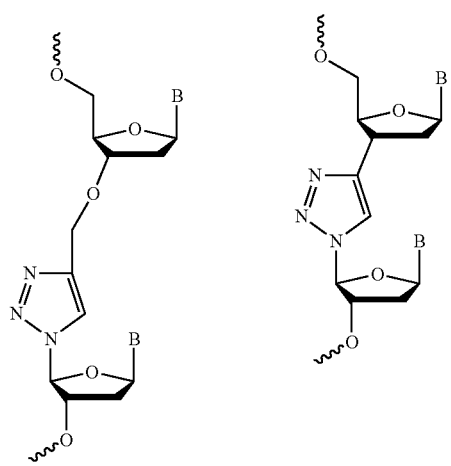

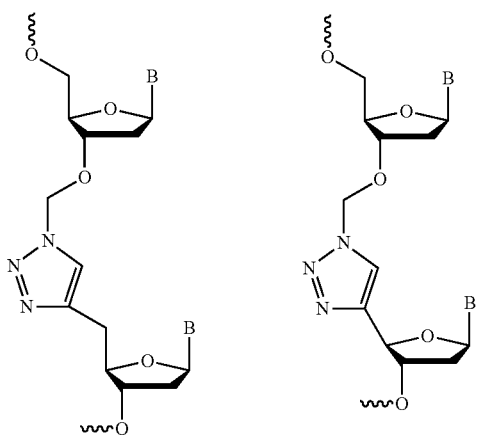

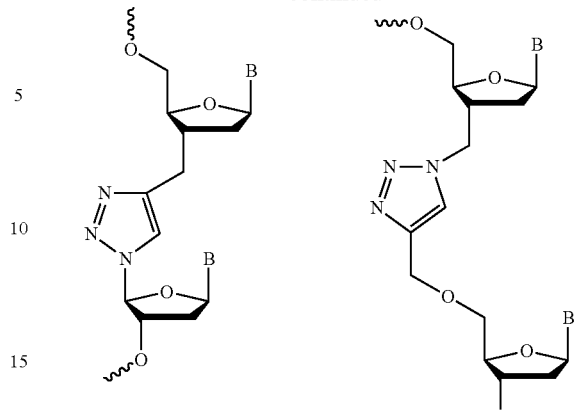

B = T, C, G or A wherein each of one or more oligonucleotides forming the oligonucleotide construct includes at least one conventional phosphodiester linkage.

21. An oligonucleotide construct according to claim 19 comprising at least two triazole phosphodiester mimics each having a structure selected from the structures described in claim 19 or an RNA equivalent thereof.

22. An oligonucleotide construct according to claim 19 comprising at least one triazole phosphodiester mimic having the following structure or an RNA equivalent thereof:

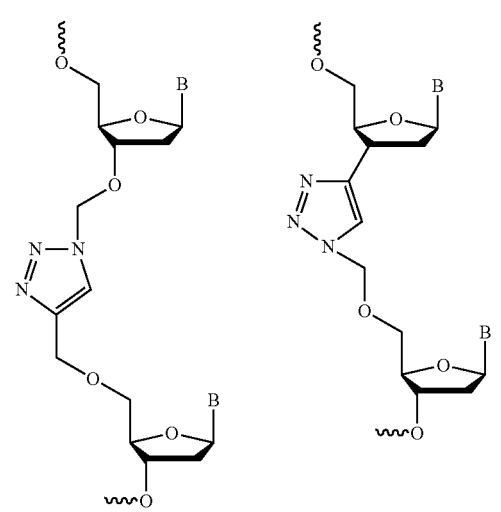

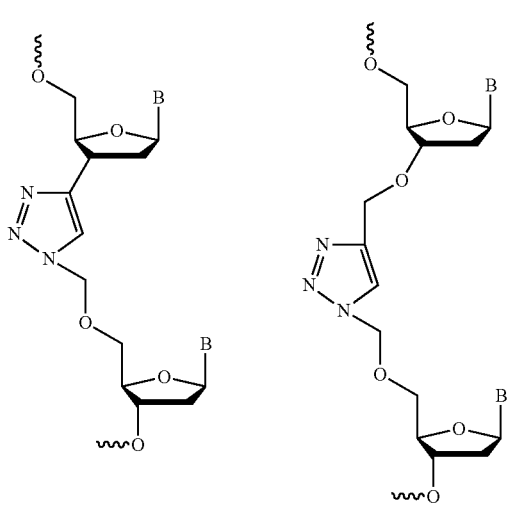

23. An oligonucleotide construct according to claim 19 wherein said at least one triazole phosphodiester mimic can be read through accurately by a DNA polymerase and/or an RNA polymerase.

24. An oligonucleotide construct according to claim 19 comprising a double stranded oligonucleotide.

25. An oligonucleotide construct according to claim 19 comprising a single stranded oligonucleotide.

26. An oligonucleotide construct according to claim 19 comprising a circularized oligonucleotide.

27. An oligonucleotide comprising one or more alkyne groups and/or one or more azide groups for use in a method according to claim 1.

* * * * *

SEQUENCE LISTING

<160> NUMBER OF SEQ ID NOS: 53

<210> SEQ ID NO 1
<211> LENGTH: 58
<212> TYPE: DNA
<213> ORGANISM: Artificial Sequence
<220> FEATURE:
<223> OTHER INFORMATION: Oligonucleotide-1 beginning with a (^z)T base
      unit, wherein z is a 5'-azide terminal group

<400> SEQUENCE: 1
taccacacaa tctcacactc tggaattcac actgacaata ctgccgacac acataacc        58

<210> SEQ ID NO 2
<211> LENGTH: 58
<212> TYPE: DNA
<213> ORGANISM: Artificial Sequence
<220> FEATURE:
<223> OTHER INFORMATION: Oligonucleotide-2 beginning with a (^z)C base
      unit, wherein z is a 5'-azide terminal group

<400> SEQUENCE: 2
cagcacacaa tctcacactc tggaattcac actgacaata ctgccgacac acataacc        58

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide-3 with (^Me)C(^k) base unit
      after nucelotide number 22, wherein k is a 3'-propargyl terminal
      group

<400> SEQUENCE: 3
gcattcgagc aacgtaagat cgc                                              23

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide-4 ending with a t(^k) base
      unit, wherein k is a 3'-propargyl terminal group

<400> SEQUENCE: 4
gcattcgagc aacgtaagat cct                                          23

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide-5 ending with a t(^k) base
      unit, wherein k is a 3'-propargyl terminal group

<400> SEQUENCE: 5
gcattcgagc aacgtaagat cgt                                          23

<210> SEQ ID NO 6
<211> LENGTH: 81
<212> TYPE: DNA
<213> ORGANISM: Artificial Sequence
<220> FEATURE:
<223> OTHER INFORMATION: Oligonucleotide-6 is a 81-mer with T(^t)T base
      unit after nucleotide number 22

<400> SEQUENCE: 6
gcattcgagc aacgtaagat ccttaccaca caatctcaca ctctggaatt cacactgaca   60
atactgccga cacacataac c                                            81

<210> SEQ ID NO 7
<211> LENGTH: 81
<212> TYPE: DNA
<213> ORGANISM: Artificial Sequence
<220> FEATURE:
<223> OTHER INFORMATION: Oligonucleotide-7 is a 81-mer with T(^t)C base
      unit after nucleotide number 22

<400> SEQUENCE: 7
gcattcgagc aacgtaagat cgtcagcaca caatctcaca ctctggaatt cacactgaca   60
atactgccga cacacataac c                                            81

<210> SEQ ID NO 8
<211> LENGTH: 81
<212> TYPE: DNA
<213> ORGANISM: Artificial Sequence
<220> FEATURE:
<223> OTHER INFORMATION: Oligonucleotide-8 is a 81-mer with (^Me)C(^t)C
      base unit after nucleotide number 22

<400> SEQUENCE: 8
gcattcgagc aacgtaagat cgccagcaca caatctcaca ctctggaatt cacactgaca   60
atactgccga cacacataac c                                            81

<210> SEQ ID NO 9
<211> LENGTH: 11
<212> TYPE: DNA
<213> ORGANISM: Artificial Sequence
<220> FEATURE:
<223> OTHER INFORMATION: Oligonucleotide-9 with (^Me)C(^k) base unit after nucelotide number 10, wherein k is a 3'-propargyl terminal group

<400> SEQUENCE: 9
gcattcatgt c        11

<210> SEQ ID NO 10
<211> LENGTH: 11
<212> TYPE: DNA
<213> ORGANISM: Artificial Sequence
<220> FEATURE:
<223> OTHER INFORMATION: Oligonucleotide-10 beginning with a (^z)C base unit, wherein z is a 5'-azide terminal group; and having a (^Me)C(^k) base unit after nucelotide number 10, wherein k is a 3'-propargyl terminal group

<400> SEQUENCE: 10
ctggtccgtg c        11

<210> SEQ ID NO 11
<211> LENGTH: 11
<212> TYPE: DNA
<213> ORGANISM: Artificial Sequence
<220> FEATURE:
<223> OTHER INFORMATION: Oligonucleotide-11 beginning with a (^z)C base unit, wherein z is a 5'-azide terminal group

<400> SEQUENCE: 11
cgcgtctaac c        11

<210> SEQ ID NO 12
<211> LENGTH: 33
<212> TYPE: DNA
<213> ORGANISM: Artificial Sequence
<220> FEATURE:
<223> OTHER INFORMATION: Oligonucleotide-12 is a 33-mer with (^Me)C(^t)C base units after nucleotide numbers 10, 21

<400> SEQUENCE: 12
gcattcatgt cctggtccgt gccgcgtcta acc        33

<210> SEQ ID NO 13
<211> LENGTH: 41
<212> TYPE: DNA
<213> ORGANISM: Artificial Sequence
<220> FEATURE:
<223> OTHER INFORMATION: Oligonucleotide-13 begnning with 5T base unit, wherein 5 is a 5'-fluorescein C6 terminal group

<400> SEQUENCE: 13
ttttggttag acgcggcacg gaccaggaca tgaatgcttt t        41

<210> SEQ ID NO 14
<211> LENGTH: 70
<212> TYPE: DNA
<213> ORGANISM: Artificial Sequence
<220> FEATURE:
<223> OTHER INFORMATION: Oligonucleotide-14 beginning with a (^z)C group, wherein z is a 5'-azide terminal group; and having a (^Me)C(^k) base unit after nucelotide number 69, wherein k is a 3'-propargyl terminal group

<400> SEQUENCE: 14
tcggtcgtcg aattctagta gatgtctaca tgtacaacat acgcgcagac gtatagacta        60
tcgctcgtgc        70

-continued

<210> SEQ ID NO 15
<211> LENGTH: 70
<212> TYPE: DNA
<213> ORGANISM: Artificial Sequence
<220> FEATURE:
<223> OTHER INFORMATION: Oligonucleotide-14a is a cyclic construct of
      Oligonucleotide-14 with (^Me)C(^t)T linkage

<400> SEQUENCE: 15
tcggtcgtcg aattctagta gatgtctaca tgtacaacat acgcgcagac gtatagacta    60
tcgctcgtgc                                                           70

<210> SEQ ID NO 16
<211> LENGTH: 70
<212> TYPE: DNA
<213> ORGANISM: Artificial Sequence
<220> FEATURE:
<223> OTHER INFORMATION: Oligonucleotide-14a is a cyclic construct of
      Oligonucleotide-14 with (^Me)C(^t)T linkage

<400> SEQUENCE: 16
gcattcgagc aacgtaagat cctgaactgg catgacggta tgacactggc atgctgtgag    60
agcatatgtc                                                           70

<210> SEQ ID NO 17
<211> LENGTH: 70
<212> TYPE: DNA
<213> ORGANISM: Artificial Sequence
<220> FEATURE:
<223> OTHER INFORMATION: Oligonucleotide-16 with (^Me)C(^k) base unit
      after nucelotide number 69, wherein k is a 3'-propargyl terminal
      group

<400> SEQUENCE: 17
tgcgtcgtct gagcagtctg atcgtgtctg agtacggcat taccagacaa tactgccgac    60
acacataacc                                                           70

<210> SEQ ID NO 18
<211> LENGTH: 40
<212> TYPE: DNA
<213> ORGANISM: Artificial Sequence
<220> FEATURE:
<223> OTHER INFORMATION: Oligonucleotide-17 is a splint oligonuceotide
      complimentary to the ends of two oligonuceotide to be ligated

<400> SEQUENCE: 18
tactagaatt cgacgaccga gacatatgct ctcacagcat                          40

<210> SEQ ID NO 19
<211> LENGTH: 40
<212> TYPE: DNA
<213> ORGANISM: Artificial Sequence
<220> FEATURE:
<223> OTHER INFORMATION: Oligonucleotide-18 is a splint oligonuceotide
      complimentary to the ends of two oligonuceotide to be ligated

<400> SEQUENCE: 19
cagactgctc agacgacgca gcacgagcga tagtctatac                          40

<210> SEQ ID NO 20
<211> LENGTH: 206
<212> TYPE: DNA
<213> ORGANISM: Artificial Sequence
<220> FEATURE:
<223> OTHER INFORMATION: Oligonucleotide-19 is a 210-mer with
      (^Me)C(^t)C base units after nucleotide numbers 69, 139

<400> SEQUENCE: 20
gcattcgagc aacgtaagat cctgaactgg catgacggta tgacactggc atgctgtgag      60
agcatatgtc ggtcgtcgaa ttctagtaga tgtctacatg tacaacatac gcgcagacgt     120
atagactatc gctcgtggcg tcgtctgagc agtctgatcg tgtctgagta cggcattacc     180
agacaatact gccgacacac ataacc                                          206

<210> SEQ ID NO 21
<211> LENGTH: 100
<212> TYPE: DNA
<213> ORGANISM: Artificial Sequence
<220> FEATURE:
<223> OTHER INFORMATION: Oligonucleotide-20 beginning with a (^z)C base
      unit, wherein z is a 5'-azide terminal group; and having a
      (^Me)C(^k) base unit after nucelotide number 99, wherein k is a
      3'-propargyl terminal group

<400> SEQUENCE: 21
ctggtcgtcg aattctagta gatgtctaca tgtacagatg tcgatacgcc agtacgcgct      60
aggatcacat acgcgcagac gtatagacta tcgctcgtgc                           100

<210> SEQ ID NO 22
<211> LENGTH: 100
<212> TYPE: DNA
<213> ORGANISM: Artificial Sequence
<220> FEATURE:
<223> OTHER INFORMATION: Oligonucleotide-21 beginning with a (^z)C
      group, wherein z is a 5'-azide terminal group

<400> SEQUENCE: 22
cgcgtcgtct gagcagtctg atcgtgtctg agtacgcatg atctggatgt gtgatgtaga      60
tcgtcagcat taccagacaa tactgccgac acacataacc                           100

<210> SEQ ID NO 23
<211> LENGTH: 100
<212> TYPE: DNA
<213> ORGANISM: Artificial Sequence
<220> FEATURE:
<223> OTHER INFORMATION: Oligonucleotide-22 with (^Me)C(^k) base unit
      after nucelotide number 99, wherein k is a 3'-propargyl terminal
      group

<400> SEQUENCE: 23
gcattcgagc aacgtaagat cctgaactgg catgacagtg agctatgcct cgcactctat      60
ctacctggta tgacactggc atgctgtgag agcatatgtc                           100

<210> SEQ ID NO 24
<211> LENGTH: 32
<212> TYPE: DNA
<213> ORGANISM: Artificial Sequence
<220> FEATURE:
<223> OTHER INFORMATION: Oligonucleotide-23 is a splint oligonuceotide
      complimentary to the ends of two oligonuceotide to be ligated

<400> SEQUENCE: 24
ctgctcagac gacgcggcac gagcgatagt ct                                    32

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide-24 is a splint oligonuceotide complimentary to the ends of two oligonuceotide to be ligated

<400> SEQUENCE: 25
agaattcgac gaccaggaca tatgctctca ca                                         32

<210> SEQ ID NO 26
<211> LENGTH: 300
<212> TYPE: DNA
<213> ORGANISM: Artificial Sequence
<220> FEATURE:
<223> OTHER INFORMATION: Oligonucleotide-25 is a 300-mer with
      (^Me)C(^t)C base units after nucleotide numbers 99, 199

<400> SEQUENCE: 26
gcattcgagc aacgtaagat cctgaactgg catgacagtg agctatgcct cgcactctat         60
ctacctggta tgacactggc atgctgtgag agcatatgtc ctggtcgtcg aattctagta        120
gatgtctaca tgtacagatg tcgatacgcc agtacgcgct aggatcacat acgcgcagac        180
gtatagacta tcgctcgtgc cgcgtcgtct gagcagtctg atcgtgtctg agtacgcatg        240
atctggatgt gtgatgtaga tcgtcagcat taccagacaa tactgccgac acacataacc        300

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide-26 is short primer for PCR
      amplification for 210-mer and 300-mer click ligated triazole DNA
      templates

<400> SEQUENCE: 27
gcattcgagc aacgtaag                                                         18

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide-27 is short primer for PCR
      amplification for 210-mer and 300-mer click ligated triazole DNA
      templates

<400> SEQUENCE: 28
ggttatgtgt gtcggcag                                                         18

<210> SEQ ID NO 29
<211> LENGTH: 28
<212> TYPE: DNA
<213> ORGANISM: Artificial Sequence
<220> FEATURE:
<223> OTHER INFORMATION: Oligonucleotide-28 is long primer for PCR
      amplification for 210-mer and 300-mer click ligated triazole DNA
      templates

<400> SEQUENCE: 29
cgcgccatgg gcattcgagc aacgtaag                                              28

<210> SEQ ID NO 30
<211> LENGTH: 28
<212> TYPE: DNA
<213> ORGANISM: Artificial Sequence
<220> FEATURE:
<223> OTHER INFORMATION: Oligonucleotide-29 is long primer for PCR
      amplification for 210-mer and 300-mer click ligated triazole DNA
      templates

```
<400> SEQUENCE: 30
cgcgctcgag ggttatgtgt gtcggcag                                          28

<210> SEQ ID NO 31
<211> LENGTH: 99
<212> TYPE: DNA
<213> ORGANISM: Artificial Sequence
<220> FEATURE:
<223> OTHER INFORMATION: Oligonucleotide-30 beginning with a (^z)T base
      unit, wherein z is a 5'-azide terminal group; and having a
      (^Me)C(^k) base unit after nucelotide number 99, wherein k is a
      3'-propargyl terminal

<400> SEQUENCE: 31
tcggtcgtcg aattctagta gatgtcacat gtacagatgt cgatacgcca gtacgcgcta      60
ggatcacata cgcgcagacg tatagactat cgctcgtgc                             99

<210> SEQ ID NO 32
<211> LENGTH: 98
<212> TYPE: DNA
<213> ORGANISM: Artificial Sequence
<220> FEATURE:
<223> OTHER INFORMATION: Oligonucleotide-31 is a cyclic oligonucleotide
      of Oligonucleotide-30 with (^Me)C(^t)T triazole linkage

<400> SEQUENCE: 32
tcggtcgtcg aattctagta gatgtcacat gtacagatgt cgatacgcca gtacgcgcta      60
ggatcacata cgcgcagacg tatagactat cgctcgtg                              98

<210> SEQ ID NO 33
<211> LENGTH: 18
<212> TYPE: DNA
<213> ORGANISM: Artificial Sequence
<220> FEATURE:
<223> OTHER INFORMATION: Oligonucleotide-32 is a primer for PCR
      amplification

<400> SEQUENCE: 33
gagcgatagt ctatacgt                                                    18

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide-33 is a primer for PCR
      amplification

<400> SEQUENCE: 34
tcgtcgaatt ctagtaga                                                    18

<210> SEQ ID NO 35
<211> LENGTH: 18
<212> TYPE: DNA
<213> ORGANISM: Artificial Sequence
<220> FEATURE:
<223> OTHER INFORMATION: Oligonucleotide-32a is a primer for PCR
      amplification having phosphothioate groups after nucleotide
      numbers 16, 17

<400> SEQUENCE: 35
gagcgatagt ctatacgt                                                    18

<210> SEQ ID NO 36
<211> LENGTH: 18
```

```
<212> TYPE: DNA
<213> ORGANISM: Artificial Sequence
<220> FEATURE:
<223> OTHER INFORMATION: Oligonucleotide-33a is a primer for PCR
      amplification having phosphothioate groups after nucleotide
      numbers 16, 17

<400> SEQUENCE: 36
tcgtcgaatt ctagtaga                                                   18

<210> SEQ ID NO 37
<211> LENGTH: 16
<212> TYPE: DNA
<213> ORGANISM: Artificial Sequence
<220> FEATURE:
<223> OTHER INFORMATION: Oligonucleotide-34 beginning with a
      5'-trimethoxystilbene terminal group and ending with a 3'-propanol
      terminal group; and having fluorescein dT groups after nucleotide
      numbers 8, 12

<400> SEQUENCE: 37
gcgcgtacgg cgatcg                                                     16

<210> SEQ ID NO 38
<211> LENGTH: 15
<212> TYPE: DNA
<213> ORGANISM: Artificial Sequence
<220> FEATURE:
<223> OTHER INFORMATION: Oligonucleotide-35 with (^Me)C(^k) base unit
      after nucelotide number 14, wherein k is a 3'-propargyl terminal
      group

<400> SEQUENCE: 38
gttgttagta ctcac                                                      15

<210> SEQ ID NO 39
<211> LENGTH: 15
<212> TYPE: DNA
<213> ORGANISM: Artificial Sequence
<220> FEATURE:
<223> OTHER INFORMATION: Oligonucleotide-36 beginning with a (^z)C base
      unit, wherein z is a 5'-azide terminal group

<400> SEQUENCE: 39
cagtcacaga aaagc                                                      15

<210> SEQ ID NO 40
<211> LENGTH: 31
<212> TYPE: DNA
<213> ORGANISM: Artificial Sequence
<220> FEATURE:
<223> OTHER INFORMATION: Oligonucleotide-37 with (^Me)C(^k) base unit
      after nucelotide number 30, wherein k is a 3'-propargyl terminal
      group

<400> SEQUENCE: 40
gttgttcgat cgttgtcaga agtaagttgg c                                    31

<210> SEQ ID NO 41
<211> LENGTH: 15
<212> TYPE: DNA
<213> ORGANISM: Artificial Sequence
<220> FEATURE:
<223> OTHER INFORMATION: Oligonucleotide-38 beginning with a (^z)C base
      unit, wherein z is a 5'-azide terminal group

<400> SEQUENCE: 41
cgcagtgtta tcact                                                      15
```

<210> SEQ ID NO 42
<211> LENGTH: 30
<212> TYPE: DNA
<213> ORGANISM: Artificial Sequence
<220> FEATURE:
<223> OTHER INFORMATION: Oligonucleotide-39 is a primer for PCR
      amplification with a (^Me)C(^t)C base unit after nucleotide number
      14

<400> SEQUENCE: 42
gttgttagta ctcaccagtc acagaaaagc                                      30

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide-40 is a primer for PCR
      amplification

<400> SEQUENCE: 43
gttgttagta ctcaccagtc acagaaaagc                                      30

<210> SEQ ID NO 44
<211> LENGTH: 46
<212> TYPE: DNA
<213> ORGANISM: Artificial Sequence
<220> FEATURE:
<223> OTHER INFORMATION: Oligonucleotide-41 is a primer for PCR
      amplification with a (^Me)C(^t)C base unit after nucleotide number
      30

<400> SEQUENCE: 44
gttgttcgat cgttgtcaga agtaagttgg ccgcagtgtt atcact                    46

<210> SEQ ID NO 45
<211> LENGTH: 46
<212> TYPE: DNA
<213> ORGANISM: Artificial Sequence
<220> FEATURE:
<223> OTHER INFORMATION: Oligonucleotide-42 is a primer for PCR
      amplification

<400> SEQUENCE: 45
gttgttcgat cgttgtcaga agtaagttgg ccgcagtgtt atcact                    46

<210> SEQ ID NO 46
<211> LENGTH: 18
<212> TYPE: DNA
<213> ORGANISM: Artificial Sequence
<220> FEATURE:
<223> OTHER INFORMATION: Oligonucleotide-43 is a splint oligonucleotide
      having a 3'-fluorescein C7 terminal group and completementary to
      two ends of the oligonucleotides to be ligated together

<400> SEQUENCE: 46
ctgtgactgg tgagtact                                                   18

<210> SEQ ID NO 47
<211> LENGTH: 18
<212> TYPE: DNA
<213> ORGANISM: Artificial Sequence
<220> FEATURE:
<223> OTHER INFORMATION: Oligonucleotide-44 is a splint oligonucleotide
      having a 3'-fluorescein C7 terminal group and completementary to
      two ends of the oligonucleotides to be ligated together

<400> SEQUENCE: 47
aacactgcgg ccaactta					18

<210> SEQ ID NO 48
<211> LENGTH: 18
<212> TYPE: DNA
<213> ORGANISM: Artificial Sequence
<220> FEATURE:
<223> OTHER INFORMATION: Oligonucleotide-45 beginning with
      5'-fluorescein C6 terminal group

<400> SEQUENCE: 48
ggttatgtgt gtcggcag					18

<210> SEQ ID NO 49
<211> LENGTH: 81
<212> TYPE: DNA
<213> ORGANISM: Artificial Sequence
<220> FEATURE:
<223> OTHER INFORMATION: Oligonucleotide-46 is a linear unmodified
      81-mer

<400> SEQUENCE: 49
gcattcgagc aacgtaagat cgccagcaca caatctcaca ctctggaatt cacactgaca		60 ataccaatac acacagccgt c					81

<210> SEQ ID NO 50
<211> LENGTH: 18
<212> TYPE: DNA
<213> ORGANISM: Artificial Sequence
<220> FEATURE:
<223> OTHER INFORMATION: Oligonucleotide-47 beginning with
      5'-fluorescein C6 terminal group

<400> SEQUENCE: 50
gacggctgtg tgtattgg					18

<210> SEQ ID NO 51
<211> LENGTH: 100
<212> TYPE: DNA
<213> ORGANISM: Artificial Sequence
<220> FEATURE:
<223> OTHER INFORMATION: Oligonucleotide-48 beginning with a
      5'-phosphate terminal group

<400> SEQUENCE: 51
tcggtcgtcg aattctagta gatgtctaca tgtacagatg tcgatacgcc agtacgcgct		60 aggatcacat acgcgcagac gtatagacta tcgctcgtgc				100

<210> SEQ ID NO 52
<211> LENGTH: 100
<212> TYPE: DNA
<213> ORGANISM: Artificial Sequence
<220> FEATURE:
<223> OTHER INFORMATION: Oligonucleotide-49 is a cyclic oligonucleotide
      of oligonucleotide-48 with phosphate linkage

<400> SEQUENCE: 52
tcggtcgtcg aattctagta gatgtctaca tgtacagatg tcgatacgcc agtacgcgct		60 aggatcacat acgcgcagac gtatagacta tcgctcgtgc				100

<210> SEQ ID NO 53
<211> LENGTH: 30
<212> TYPE: DNA

```
<213> ORGANISM: Artificial Sequence
<220> FEATURE:
<223> OTHER INFORMATION: Oligonucleotide-50 is a splint oligonuceotide
      complimentary to the ends of two oligonuceotide to be ligated

<400> SEQUENCE: 53
gaattcgacg accgagcacg agcgatagtc                                        30
```